United States Patent
Nakayama et al.

(10) Patent No.: US 10,072,033 B2
(45) Date of Patent: Sep. 11, 2018

(54) N-(PHOSPHINOALKYL)-N-(THIOALKYL)AMINE DERIVATIVE, METHOD FOR PRODUCING SAME, AND METAL COMPLEX THEREOF

(71) Applicant: TAKASAGO INTERNATIONAL CORPORATION, Tokyo (JP)

(72) Inventors: Yuji Nakayama, Kamakura (JP); Osamu Ogata, Chigasaki (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 12 days.

(21) Appl. No.: 15/502,813

(22) PCT Filed: Aug. 26, 2015

(86) PCT No.: PCT/JP2015/074069
§ 371 (c)(1),
(2) Date: Feb. 9, 2017

(87) PCT Pub. No.: WO2016/031874
PCT Pub. Date: Mar. 3, 2016

(65) Prior Publication Data
US 2017/0233418 A1 Aug. 17, 2017

(30) Foreign Application Priority Data
Aug. 26, 2014 (JP) .................... 2014-172100

(51) Int. Cl.
*C07F 15/00* (2006.01)
*C07F 9/50* (2006.01)

(52) U.S. Cl.
CPC .......... *C07F 9/5022* (2013.01); *C07F 9/5077* (2013.01); *C07F 15/0053* (2013.01)

(58) Field of Classification Search
CPC .............. C07F 15/0046; C07F 15/0053; C07F 9/5018; C07F 9/5022; C07F 9/5077; C07F 9/653

See application file for complete search history.

(56) References Cited

U.S. PATENT DOCUMENTS

2011/0237814 A1 9/2011 Kuriyama et al.
2016/0326199 A1 11/2016 Geisser et al.

FOREIGN PATENT DOCUMENTS

WO 2011/048727 A1 4/2011
WO 2015/110515 A1 7/2015

OTHER PUBLICATIONS

Bluhm et al., "Chromium imine and amine complexes as homogeneous catalysts for hte trimerisation and polymerisation of ethylene," Journal of Organometallic Chemistry 690 (2005) 713-721 (Year: 2005).*
Denis Spasyuk et al., "Replacing Phosphorus with Sulfur for the Efficient Hydrogenation of Esters", Angew. Chem. Int. Ed., 2013, pp. 2538-2542, vol. 52.
Moti Gargir et al., "PNS-Type Ruthenium Pincer Complexes", Organometallics, 2012, pp. 6207-6214, vol. 31.
International Searching Authority, International Search Report of PCT/JP2015/074069 dated Nov. 24, 2015 [PCT/ISA/210].

* cited by examiner

Primary Examiner — Pancham Bakshi
Assistant Examiner — Mark R Luderer
(74) Attorney, Agent, or Firm — Sughrue Mion, PLLC

(57) ABSTRACT

The purpose of the present invention is to provide: a ligand that is useful in a catalytic organic synthetic reaction; a method for producing said ligand; and a metal complex that is useful as a catalyst in an organic synthetic reaction. The present invention provides a compound represented by general formula ($1^4$), a method for producing said compound, and a metal complex including said compound as a ligand. (In the formula, H, N, P, S, L, $R^1$, $R^2$, $R^3$, $Q^1$, and $Q^2$ have the meaning as defined in the Description.)

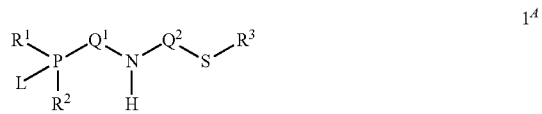

9 Claims, 19 Drawing Sheets

N-(PHOSPHINOALKYL)-N-(THIOALKYL)AMINE DERIVATIVE, METHOD FOR PRODUCING SAME, AND METAL COMPLEX THEREOF

CROSS REFERENCE TO RELATED APPLICATIONS

This application is a National Stage of International Application No. PCT/JP2015/074069, filed Aug. 26, 2015, claiming priority based on Japanese Patent Application No. 2014-172100, filed Aug. 26, 2014, the contents of all of which are incorporated herein by reference in their entirety.

TECHNICAL FIELD

The present invention relates to a novel N-(phosphino-alkyl)-N-(thioalkyl)amine derivative, a method for producing the same, and a metal complex having the compound as a ligand.

BACKGROUND ART

Nowadays, various metal complexes comprising metal species and ligands are used as catalysts for organic synthesis reactions. It is known that factors for expression of the performance and activity of such a catalyst include not only the metal species but also the ligand in the metal complex, in other words, it is known that an organic compound having a group (coordination group) having lone pair electrons capable of coordinating to the metal species plays an extremely important role. Of such ligands, an organic compound (tridentate ligand) having three coordination groups has such a characteristic that the tridentate ligand binds to a metal species in a facial or meridional fashion to form a metal complex having two chelate rings. Moreover, a "Hemilabile" tridentate ligand, which has electrically inequivalent coordination groups, is known to be capable of functioning also as a monodentate ligand or a bidentate ligand in a catalyst cycle in a catalytic reaction. For this reason, changing the structures and the combination of the three coordination groups in a tridentate ligand in various manners makes it possible to adjust the structure, the physical properties, the catalytic activities, and the like of the corresponding metal complex at will. Accordingly, tridentate ligands and metal complexes thereof occupy important positions in the fields of synthetic organic chemistry, complex chemistry, catalyst chemistry, and the like, and are still being actively researched and developed. Especially, metal complexes of tridentate ligands having an imino group as a coordination group in each molecule are known to exhibit high catalytic activities in, for example, hydrogenation reactions of carbonyl compounds, dehydrogenation reactions of alcohols, and the like, and also the hydrogen atom on the imino group is known to exert great influences on the expression of activities in these catalytic organic synthesis reactions. Known examples of such a tridentate ligand include N,N-bis(2-phosphinoethyl)amine and N,N-bis(2-thioethyl)amine, which are symmetrical, and it is reported that ruthenium complexes thereof function as excellent catalysts in hydrogenation reactions of esters (Patent Literature 1 and Non Patent Literature 1). Here, these tridentate ligands having an imino group can be synthesized easily by simultaneously introducing phosphino groups or thio groups serving as the coordination groups to N,N-bis(2-chloroethyl)amine serving as a substrate. However, because of the chemically equivalent two chloro groups on the substrate, it is extremely difficult to successively and selectively introduce different coordination groups, which are important from the viewpoint of "Hemilability," although the same coordination groups can be introduced. Therefore, there has been no report so far on any example of synthesis of N-(2-phosphinoethyl)-N-(2-thioethyl)amine, which would be obtained if successive introduction of a phosphino group and a thio group is conducted successfully. On the other hand, 2-phosphinomethyl-6-thiomethylpyridine derivatives, which are asymmetric tridentate ligands each having a phosphino group and a thio group and also having a pyridyl group instead of an imino group, and ruthenium complexes thereof are already known (Non Patent Literature 2). However, since the nitrogen atom is contained not in an imino group but in the pyridine ring, such a ruthenium complex is easily dimerized under a basic condition, while forming ruthenium-carbon bonds. This dimer is an inactive species in catalytic reactions, and hence causes problems of narrow scope of the reaction and poor activity.

CITATION LIST

Patent Literature 1: International Publication No. WO2011/048727

NON PATENT LITERATURES

Non Patent Literature 1: Denys Spasyuk, Samantha Smith, and Dmitry G. Gusev, Angew. Chem. Int. Ed. Ingl., 2013, 52, 2538.

Non Patent Literature 2: Moti Gargir, Yehosyua Ben-David, Gregory Leitus, Yael Diskin-Posner, Linda J. W. Shimon, and David Milstein, Organometallics, 2012, 31, 6207.

SUMMARY OF INVENTION

The present invention has been made in view of the above-described circumstances. Specifically, the structures and the combination of the three coordination groups on a tridentate ligand and further the presence or absence of "Hemilability" are important in research and development of the tridentate ligand, a metal complex thereof, and an organic synthesis reaction using the metal complex as a catalyst. Hence, increasing the varieties thereof will contribute to improvement of efficiencies of known organic synthesis reactions and to discovery of novel useful reactions. From such a viewpoint, an object of the present invention is to provide a simple method for producing an asymmetric tridentate ligand based on successive introduction of different coordination groups, for example, a phosphino group and a thio group to a skeleton having an imino group, a novel asymmetric tridentate ligand obtained by this approach, a metal complex thereof, and a catalytic organic synthesis reaction using the metal complex. The present inventors have conducted intensive study to achieve the above-described object, and consequently have succeeded in synthesizing an asymmetric N-(2-phosphinoethyl)-N-(2-thioethyl)amine derivative (a simplified outline is shown in Eq. 1 below, but the present invention is not limited to the outline at all), which is unreported so far, by deriving 3-(2-chloroethyl)-2-oxazolidinone from N,N-bis(2-chloroethyl)amine, which is a raw material of a conventional symmetrical tridentate ligand, by a reaction with carbon dioxide, and then successively introducing a phosphino group and a thio group to this compound.

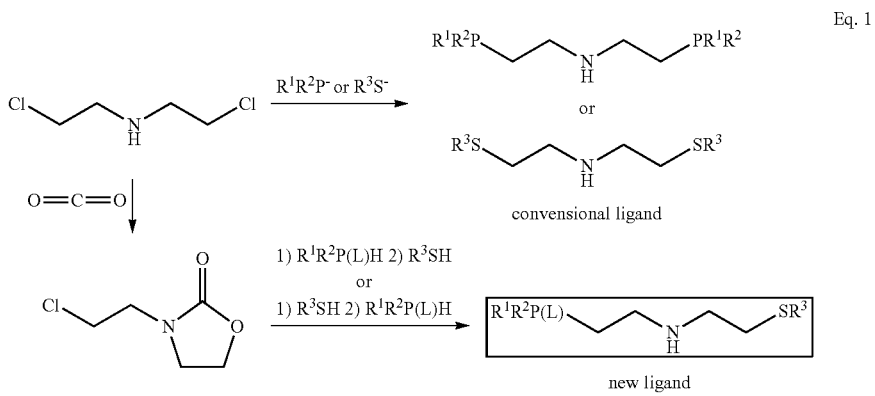

Eq. 1

This novel compound acts as an asymmetric tridentate ligand, and metal complexes having excellent catalytic activities can be obtained by coordinating the compound to various metal species. For example, it has been found that a ruthenium complex of this compound has better catalytic activities in hydrogenation reactions of esters than ruthenium complexes of N,N-bis(2-phosphinoethyl)amine and N,N-bis(2-thioethyl)amine, which are conventional symmetrical tridentate ligands. On the basis of these findings, the present invention has been completed.

Specifically, the present invention includes the following [1] to [13]:

[1] A compound represented by the following general formula ($1^A$):

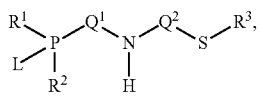

$1^A$ wherein H represents a hydrogen atom, N represents a nitrogen atom, P represents a phosphorus atom, and S represents a sulfur atom; L represents lone pair electrons or boron trihydride; $R^1$, $R^2$, and $R^3$ each independently represent a group selected from the group consisting of alkyl groups, optionally substituted alkenyl groups, optionally substituted aryl groups, optionally substituted heteroaryl groups, and optionally substituted aralkyl groups; $R^1$ and $R^2$ may be bonded to each other to form an optionally substituted ring; $Q^1$ and $Q^2$ each independently represent an alkanediyl group selected from the group consisting of a 1,2-ethanediyl group, a 1,3-propanediyl group, and a 1,4-butanediyl group; and $Q^1$ and $Q^2$ may be substituted with groups selected from the group consisting of alkyl groups, optionally substituted alkenyl groups, optionally substituted aryl groups, and optionally substituted aralkyl groups, provided that these groups may be bonded to each other to form an optionally substituted ring.

[2] The compound according to the above-described [1], wherein
$Q^1$ is a 1,2-ethanediyl group.

[3] The compound according to the above-described [1], wherein
$Q^2$ is a 1,2-ethanediyl group.

[4] The compound according to the above-described [1], wherein
each of $Q^1$ and $Q^2$ is a 1,2-ethanediyl group.

[5] The compound according to any one of the above-described [1] to [4], wherein the compound is an optically active compound.

[6] A Bronsted acid salt of the compound according to any one of the above-described [1] to [5], wherein
the Bronsted acid salt is formed from the compound according to any one of the above-described [1] to [5] and a Bronsted acid selected from the group consisting of hydrohalic acids, perchloric acid, nitric acid, sulfuric acid, sulfonic acids, carboxylic acids, phenols, phosphoric acid, hexafluorophosphoric acid, boric acid, and tetrafluoroboric acid.

[7] A method for producing the compound according to any one of the above-described [1] to [6], the method comprising reacting
a compound represented by the following general formula ($2^A$):

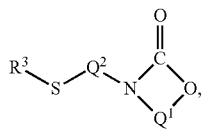

$2^A$ wherein C represents a carbon atom, N represents a nitrogen atom, O represents an oxygen atom, and S represents a sulfur atom; and $R^3$, $Q^1$, and $Q^2$ represent the same groups as $R^3$, $Q^1$, and $Q^2$ defined in the above-described [1], with
a compound represented by the following general formula (4):

4 wherein H represents a hydrogen atom and P represents a phosphorus atom; L represents lone pair electrons or boron trihydride; and $R^1$ and $R^2$ represent the same groups as $R^1$ and $R^2$ defined in the above-described [1].

[8] A method for producing a compound according to any one of the above-described [1] to [6], the method comprising reacting a compound represented by the following general formula (3$^A$):

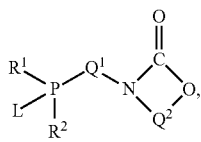

wherein C represents a carbon atom, N represents a nitrogen atom, O represents an oxygen atom, and P represents a phosphorus atom; L represents lone pair electrons or boron trihydride; and $R^1$, $R^2$, $Q^1$ and $Q^2$ represent the same groups as $R^1$, $R^2$, $Q^1$ and $Q^2$ defined in the above-described [1], with a compound represented by the following general formula (5):

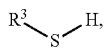

wherein H represents a hydrogen atom and S represents a sulfur atom; and $R^3$ represents the same group as $R^3$ defined in the above-described [1].

[9] A metal complex comprising the compound according to any one of the above-described [1] to [5] as a ligand.
[10] The metal complex according to the above-described [9], wherein
the metal species is selected from the group consisting of group 5 transition metals, group 6 transition metals, group 7 transition metals, group 8 transition metals, group 9 transition metals, group 10 transition metals, and group 11 transition metals.
[11] The metal complex according to the above-described [10], wherein
the metal species is selected from the group consisting of group 8 transition metals, group 9 transition metals, and group 10 transition metals.
[12] The metal complex according to the above-described [11], wherein
the metal complex is represented by compositional formula (8$^A$): $[M^8X^1X^2(L^1)_k(L^2)_l(L^3)_m(PNS)]_n$,
wherein $M^8$ represents a divalent group 8 transition metal ion selected from the group consisting of a divalent iron ion, a divalent ruthenium ion, and a divalent osmium ion; $X^1$ and $X^2$ each independently represent a monoanionic monodentate ligand, and L, $L^2$, and $L^3$ each independently represent a neutral monodentate ligand; k, l, and m, which respectively represent the coordination numbers of $L^1$, $L^2$, and $L^3$, each independently represent an integer of 0 or 1; PNS represents the compound according to any one of the above-described [1] to [5]; and n, which represents the degree of multimerization of the compositional formula: $[M^8X^1X^2(L^1)_k(L^2)_l(L^3)_m(PNS)]$, represents an integer of 1 or 2, provided that n represents 1 when the total of k, l, and m is an integer of 1 to 3, and represents 1 or 2 when the total is 0.
[13] The metal complex according to the above-described [11], wherein the metal complex is represented by compositional formula (9$^A$): $M^9X^1X^2X^3(L^1)_k(L^2)_l(L^3)_m(PNS)$,
wherein $M^9$ represents a trivalent group 9 transition metal ion selected from the group consisting of a trivalent cobalt ion, a trivalent rhodium ion, and a trivalent iridium ion; XL, $X^2$, and $X^3$ each independently represent a monoanionic monodentate ligand, and $L^1$, $L^2$, and $L^3$ each independently represent a neutral monodentate ligand; k, l, and m, which respectively represent the coordination numbers of $L^1$, $L^2$, and $L^3$, each independently represent an integer of 0 or 1; and PNS represents the compound according to any one of the above-described [1] to [5].
[14] The metal complex according to the above-described [11], wherein
the metal complex is represented by compositional formula (10$^A$): $M^{10}X^1X^2(L^1)_k(PNS)$,
wherein $M^{10}$ represents a divalent group 10 transition metal ion selected from the group consisting of a divalent nickel ion, a divalent palladium ion, and a divalent platinum ion; $X^1$ and $X^2$ each independently represent a monoanionic monodentate ligand, and $L^1$ represents a neutral monodentate ligand; k, which represents the coordination number of $L^1$, represents an integer of 0 or 1; and PNS represents the compound according to any one of the above-described [1] to [5].

The previously unknown compound represented by general formula (1$^A$) (hereinafter, referred to as the compound of the present invention; note that this compound is abbreviated as PNS in compositional formulae) is first successfully synthesized by establishing a method for successively introducing a phosphino group and a thio group into a cyclic carbamate derivative such as 3-(2-chloroethyl)-2-oxazolidinone. The compound of the present invention has electrically inequivalent three coordination groups, namely, a phosphino group, an imino group, and a thio group, and hence is expected to act as a "Hemilabile" tridentate ligand. Actually, it has been revealed that the compound of the present invention is coordinated to various metal species to form the corresponding metal complexes (hereinafter, referred to as metal complexes of the present invention), and the thus obtained metal complexes of the present invention exhibit excellent catalytic activities in catalytic organic synthesis reactions. For example, a ruthenium complex of the compound of the present invention exhibits better catalytic activities in hydrogenation reactions of esters than ruthenium complexes of N,N-bis(2-phosphinoethyl)amine and N,N-bis(2-thioethyl)amine, which are conventional symmetrical tridentate ligands, and these reactions make it possible to produce alcohols more efficiently.

DESCRIPTION OF EMBODIMENTS

Figure 1:
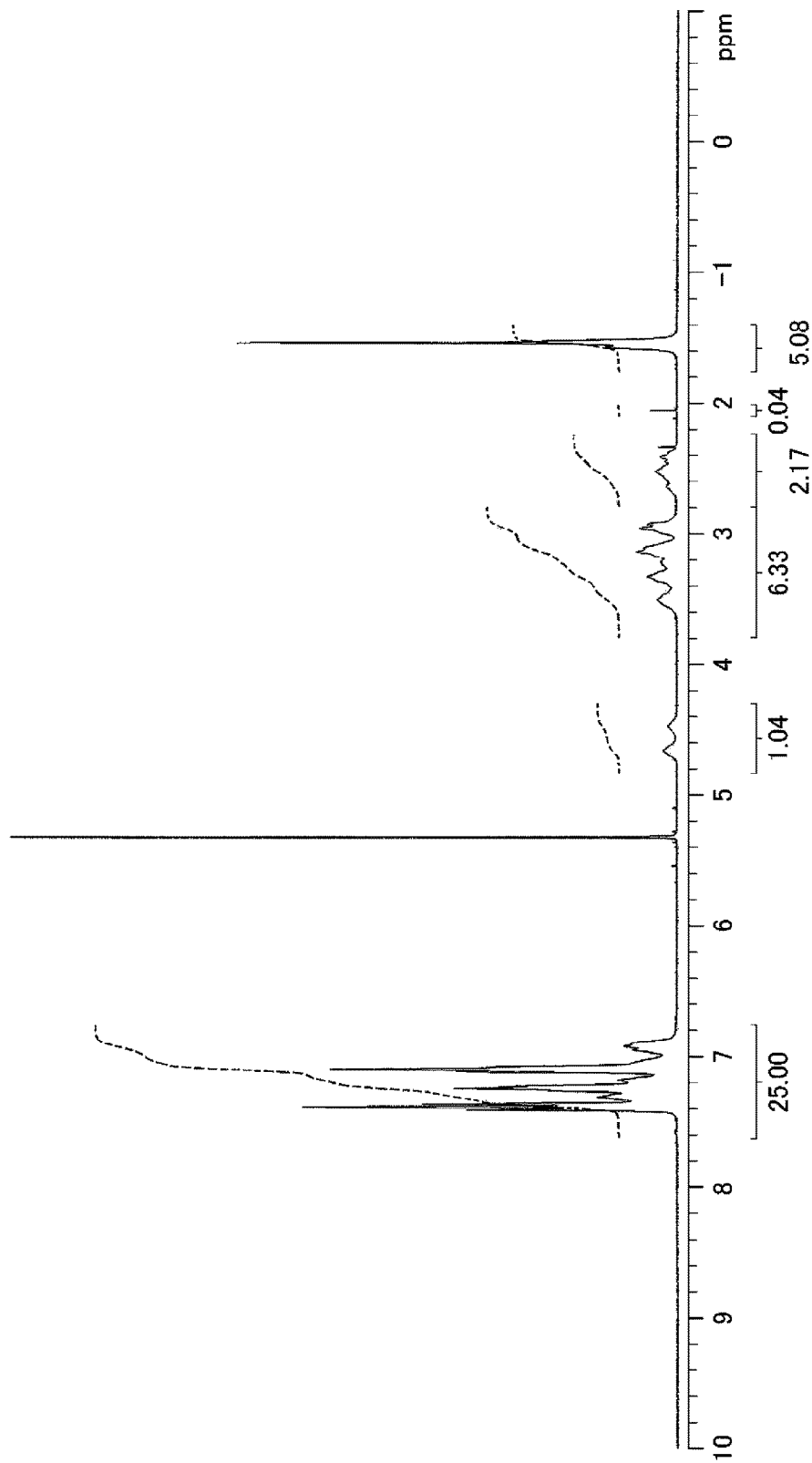
FIG. 1 is a $^1$H NMR chart of dichloro(triphenylphosphine){2-diphenylphosphino-N-[2-(methylthio)ethyl]ethylamine}ruthenium(II) (8$^S$-1) (Example 11).

Hereinafter, compound ($1^A$) of the present invention and a compound represented by general formula ($2^A$) shown above, a compound represented by general formula ($3^A$) shown above, a compound represented by general formula (4) shown above, and a compound represented by general formula (5) shown above, which are raw material compounds of compound ($1^A$), are described in detail.

In general formulae ($1^A$), ($2^A$), ($3^A$), (4), and (5) shown above, C represents a carbon atom, H represents a hydrogen atom, N represents a nitrogen atom, O represents an oxygen atom, P represents a phosphorus atom, and S represents a sulfur atom. L represents lone pair electrons or boron trihydride. $R^1$, $R^2$, and $R^3$ each independently represent a group selected from the group consisting of alkyl groups, optionally substituted alkenyl groups, optionally substituted aryl groups, optionally substituted heteroaryl groups, and optionally substituted aralkyl groups, and preferably represent a group selected from the group consisting of alkyl groups and optionally substituted aryl groups. $Q^1$ and $Q^2$ each independently represent an alkanediyl group selected from the group consisting of a 1,2-ethanediyl group, a 1,3-propanediyl group, and a 1,4-butanediyl group, and preferably represent a 1,2-ethanediyl group. $Q^1$ may be substituted with a group(s) selected from the group consisting of alkyl groups, optionally substituted alkenyl groups, optionally substituted aryl groups, and optionally substituted aralkyl groups (hereinafter, referred to as groups on $Q^1$). Meanwhile, $Q^2$ may also be substituted with a group(s) selected from the group consisting of alkyl groups, optionally substituted alkenyl groups, optionally substituted aryl groups, and optionally substituted aralkyl groups (hereinafter, referred to as groups on $Q^2$).

The alkyl groups may be linear, branched, or cyclic, and are, for example, alkyl groups having 1 to 30 carbon atoms, preferably alkyl groups having 1 to 20 carbon atoms, and more preferably alkyl groups having 1 to 10 carbon atoms. Specifically, the alkyl groups include a methyl group, an ethyl group, a n-propyl group, a 2-propyl group, a cyclopropyl group, a n-butyl group, a 2-butyl group, an isobutyl group, a tert-butyl group, a cyclobutyl group, a n-pentyl group, a 2-pentyl group, a 3-pentyl group, a tert-pentyl group, a 2-methylbutyl group, a 3-methylbutyl group, a 2-methylbutan-3-yl group, a 2,2-dimethylpropyl group, a cyclopentyl group, a n-hexyl group, a 2-hexyl group, a 3-hexyl group, a tert-hexyl group, a 2-methylpentyl group, a 3-methylpentyl group, a 4-methylpentyl group, a 2-methylpentan-3-yl group, a 2-methylpentan-4-yl group, a 3-methylpentan-2-yl group, a 3-methylpentan-3-yl group, a 2,2-dimethylbutyl group, a 3,3-dimethylbutyl group, a 2,2-dimethylbutan-3-yl group, a cyclohexyl group, a n-heptyl group, a n-octyl group, a n-nonyl group, a n-decyl group, a 1-adamantyl group, a 2-adamantyl group, and the like, and preferred specific examples thereof include a methyl group, an ethyl group, a tert-butyl group, a cyclohexyl group, and a 1-adamantyl group.

The alkenyl groups may be linear, branched, or cyclic, and are, for example, alkenyl groups having 2 to 20 carbon atoms, preferably alkenyl groups having 2 to 14 carbon atoms, and more preferably alkenyl groups having 2 to 8 carbon atoms. Specifically, the alkenyl groups include a vinyl group, a 1-propenyl group, a 2-propenyl group, an allyl group, a 1-cyclohexenyl group, a 1-styryl group, a 2-styryl group, and the like.

The aryl groups are, for example, aryl groups having 6 to 18 carbon atoms, preferably aryl groups having 6 to 14 carbon atoms, and more preferably aryl groups having 6 to 10 carbon atoms. Specifically, the aryl groups include a phenyl group, a 1-naphthyl group, a 2-naphthyl group, and the like, and a preferred specific example is a phenyl group.

The heteroaryl groups include heteroaryl groups derived from aromatic heterocycles having a 5 to 6-membered ring and containing 1 to 4 heteroatoms selected from the group consisting of nitrogen atoms, oxygen atoms, and sulfur atoms, and heteroaryl groups derived from polycyclic aromatic heterocycles which are formed by fusion of the above-described aromatic heterocycles with the above-described aryl groups. Specifically, the heteroaryl groups include a 2-furyl group, a 3-furyl group, a 2-thienyl group, a 3-thienyl group, a 2-benzofuryl group, a 3-benzofuryl group, a 2-benzothienyl group, a 3-benzothienyl group, and the like.

The aralkyl groups include aralkyl groups in each of which at least one hydrogen atom of one of the above-described alkyl groups is substituted with one of the above-described aryl groups, and polycyclic aralkyl groups each of which is formed by fusion of one of the above-described cyclic alkyl groups with one of the above-described aryl groups. Specifically, the aralkyl groups include a benzyl group, a 1-phenylethyl group, a 2-phenylethyl group, a 1-phenylpropyl group, a 2-phenylpropyl group, a 3-phenylpropyl group, a 1-phenyl-2-propyl group, a 2-phenyl-2- propyl group, a 1-indanyl group, a 2-indanyl group, a 9-fluorenyl group, and the like.

$R^1$ and $R^2$ may be bonded to each other to form an optionally substituted ring. Specific examples of the ring include a phospholane ring, a phosphole ring, a phosphinane ring, a phosphinine ring, and the like. Moreover, each of a pair of groups on $Q^1$, a pair of a group on $Q^1$ and a group on $Q^2$, and a pair of groups on $Q^2$ in each of general formulae ($1^A$), ($2^A$), and ($3^A$) may be bonded to each other to form an optionally substituted ring.

Substituents which may be present on the alkenyl groups, the aryl groups, the heteroaryl groups, and the aralkyl group serving as $R^1$ to $R^3$, the alkenyl groups, the aryl groups, and the aralkyl groups serving as the groups on $Q^1$ and the groups on $Q^2$, the ring formed when $R^1$ and $R^2$ are bonded to each other, the ring formed when any ones of the groups on $Q^1$ are bonded to each other, the ring formed when any one of the groups on $Q^1$ and any one of the groups on $Q^2$ are bonded to each other, and the ring formed when any ones of the groups on $Q^2$ are bonded to each other include alkyl groups, halogenoalkyl groups, alkenyl groups, aryl groups, heteroaryl groups, aralkyl groups, alkoxy groups, halogeno groups, and the like. Of these substituents, the alkyl groups, the alkenyl groups, the aryl groups, the heteroaryl groups, and the aralkyl groups are the same as those described in detail above.

The halogenoalkyl groups include groups which are the same as the above-described alkyl groups, except that at least one hydrogen atom is replaced with a halogen atom, and specifically include a trifluoromethyl group, a n-nonafluorobutyl group, and the like.

The alkoxy groups are, for example, alkoxy groups having 1 to 10 carbon atoms, and preferably alkoxy groups having 1 to 4 carbon atoms. Specifically, the alkoxy groups include a methoxy group, an ethoxy group, a 1-propoxy group, a 2-propoxy group, a 1-butoxy group, a 2-butoxy group, a tert-butoxy group, and the like.

Specifically, the halogeno groups include a fluoro group, a chloro group, a bromo group, and an iodo group, and are preferably a fluoro group and a chloro group.

In a preferred mode, the compound of the present invention may be specifically a compound represented by general formula ($1^A$) shown above, in which $Q^1$ is a 1,2-ethanediyl group, i.e., a compound represented by the following general formula ($1^B$):

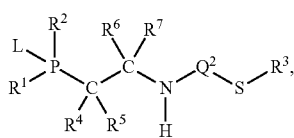

wherein H, N, P, S, L, $R^1$, $R^2$, $R^3$, and $Q^2$ are the same as those defined in general formula ($1^A$); C represents a carbon atom; $R^4$, $R^5$, $R^6$, and $R^7$ each independently represent a group selected from the group consisting of a hydrogen atom, alkyl groups, optionally substituted alkenyl groups, optionally substituted aryl groups, and optionally substituted aralkyl groups; and any ones of $R^4$ to $R^7$ may be bonded to each other to form an optionally substituted ring, or any one of $R^4$ to $R^7$ may be bonded to a group on $Q^2$ to form an optionally substituted ring, or a compound represented by general formula ($1^A$) shown above, in which $Q^2$ is a 1,2-ethanediyl group, i.e., a compound represented by the following general formula ($1^C$):

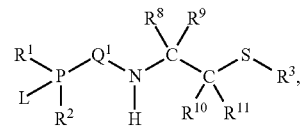

wherein H, N, P, S, L, $R^1$, $R^2$, $R^3$, and $Q^1$ are the same as those defined in general formula ($1^A$); C represents a carbon atom; $R^8$, $R^9$, $R^{10}$, and $R^{11}$ each independently represent a group selected from the group consisting of a hydrogen atom, alkyl groups, optionally substituted alkenyl groups, optionally substituted aryl groups, and optionally substituted aralkyl groups; any ones of $R^8$ to $R^{11}$ may be bonded to each other to form an optionally substituted ring, or any one of $R^8$ to $R^{11}$ may be bonded to a group on $Q^1$ to form an optionally substituted ring. In a more preferred mode, the compound of the present invention specifically may be a compound represented by general formula ($1^A$) shown above, in which each of $Q^1$ and $Q^2$ is a 1,2-ethanediyl group, i.e., a compound represented by the following general formula ($1^D$)

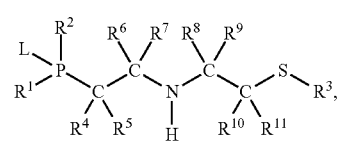

wherein H, N, P, S, L, $R^1$, $R^2$, and $R^3$ are the same as those defined in general formula ($1^A$) shown above; C represents a carbon atom; $R^4$, $R^5$, $R^6$, $R^7$, $R^8$, $R^9$, $R^{10}$, and $R^{11}$ each independently represent a group selected from the group consisting of a hydrogen atom, alkyl groups, optionally substituted alkenyl groups, optionally substituted aryl groups, and optionally substituted aralkyl groups; and any ones of $R^4$ to $R^{11}$ may be bonded to each other to form an optionally substituted ring.

In each of general formulae ($1^B$), ($1^C$), and ($1^D$), $R^4$, $R^5$, $R^6$, $R^7$, $R^8$, $R^9$, $R^{10}$, and $R^{11}$ each independently represent a group selected from the group consisting of a hydrogen atom, alkyl groups, optionally substituted alkenyl groups, optionally substituted aryl groups, and optionally substituted aralkyl groups, and preferably represent a hydrogen atom. The alkyl groups, the alkenyl groups, the aryl groups, and the aralkyl groups serving as $R^4$ to $R^{11}$ are the same as the groups serving as the groups on $Q^1$ and the groups on $Q^2$.

In addition, substituents which may be present on the alkenyl groups, the aryl groups, and the aralkyl groups serving as $R^4$ to $R^{11}$, the ring formed when any ones of $R^4$ to $R^7$ are bonded to each other, the ring formed when any one of $R^4$ to $R^7$ is bonded to a group on $Q^2$, the ring formed when any ones of $R^8$ to $R^{11}$ are bonded to each other, the ring formed when any one of $R^8$ to $R^{11}$ is bonded to a group on $Q^1$, and the ring formed when any ones of $R^4$ to $R^{11}$ are bonded to each other include alkyl groups, halogenoalkyl groups, alkenyl groups, aryl groups, heteroaryl groups, aralkyl groups, alkoxy groups, halogeno groups, and the like. These substituents are the same as those described in detail above.

Some of compounds ($1^A$) to ($1^D$) are difficult to purify or weigh, because some substances are unstable in air, or are liquid with high viscosity. To facilitate the handling, such a compound may be reacted with a Bronsted acid, for example, a hydrohalic acid, perchloric acid, nitric acid, sulfuric acid, a sulfonic acid, a carboxylic acid, a phenol, phosphoric acid, hexafluorophosphoric acid, boric acid, tetrafluoroboric acid, or the like to form the corresponding Bronsted acid salt. Specifically, the hydrohalic acid may be hydrofluoric acid, hydrochloric acid, hydrobromic acid, hydroiodic acid, or the like, and is preferably hydrochloric acid. Specifically, the sulfonic acid may be methanesulfonic acid, trifluoromethanesulfonic acid, p-toluenesulfonic acid, 10-camphorsulfonic acid, or the like. Specifically, the carboxylic acid may be formic acid, acetic acid, trifluoroaceticacid, benzoic acid, salicylic acid, oxalic acid, tartaric acid, or the like. Specifically, the phenol may be phenol, p-cresol, p-nitrophenol, pentafluorophenol, or the like.

When the Bronsted acid salt of the compound of the present invention is used for producing a metal complex of the present invention, the compound may be used for the reaction in the form of the Bronsted acid salt, as it is. Alternatively, the compound of the present invention may be used for the reaction after being liberated by a treatment with a base outside the reaction system, or may be used for the reaction while being liberated by a treatment with a base in the reaction system.

Moreover, when the compound of the present invention in which L is boron trihydride is used for producing a metal complex of the present invention, the compound of the present invention may be used for the reaction, as it is. Alternatively, the compound of the present invention may be used for the reaction after the boron trihydride is dissociated outside the reaction system, or the compound of the present invention may be used for the reaction while the boron trihydride is being dissociated in the reaction system. For the dissociation of boron trihydride, it is preferable to use a dissociation agent in combination, and examples of the dissociation agent for boron trihydride include amines such as diethylamine, triethylamine, and 1,4-diazabicyclo[2,2,2]octane.

In a particularly preferred mode, specific examples of the compound of the present invention include the following compounds ($1^D$-1) to ($1^D$-7) and Bronsted acid salts thereof:

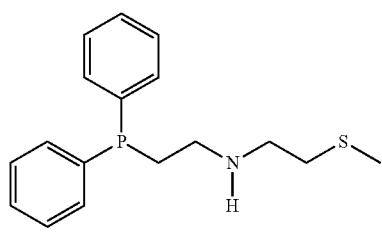

$1^D$-1

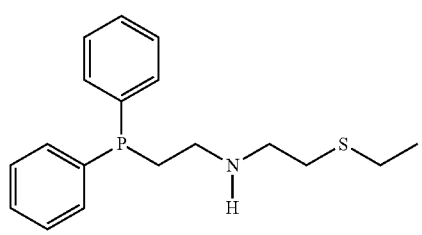

$1^D$-2

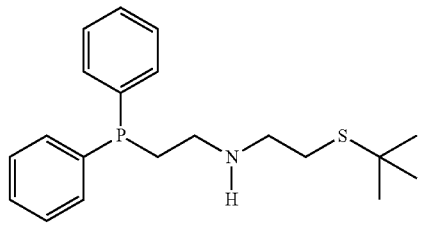

$1^D$-3

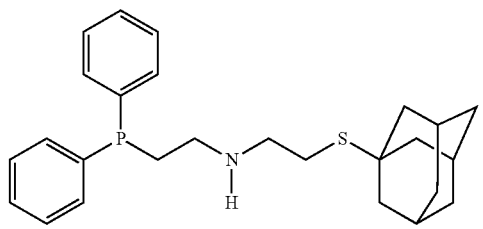

$1^D$-4

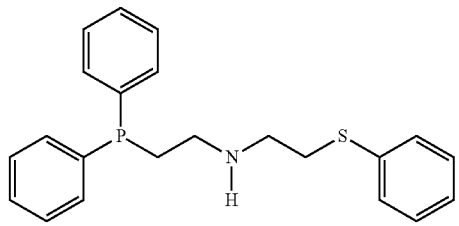

$1^D$-5

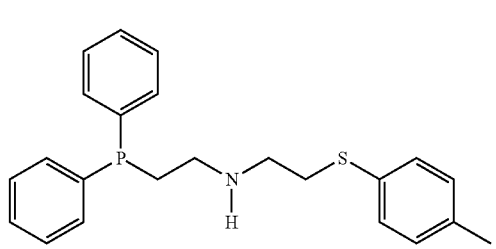

$1^D$-6

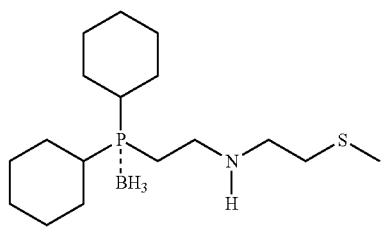

$1^D$-7

Next, the compound represented by general formula ($2^A$) and the compound represented by general formula ($3^A$), which are raw material compounds of the compound of the present invention, are described in further detail. First, the compound represented by general formula ($2^A$) can be obtained easily by reacting a compound represented by the following general formula (6):

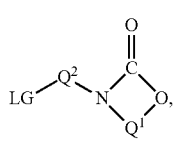

6 wherein C, N, O, Q¹ and Q² are the same as those defined in general formula (2) shown above; and LG represents a leaving group, with a compound represented by general formula (5) under a basic condition. Note that, in a preferred mode, the compound represented by general formula (2^A) specifically may be a compound represented by general formula (2^A) shown above, in which Q¹ is a 1,2-ethanediyl group, i.e., a compound represented by the following general formula (2^B):

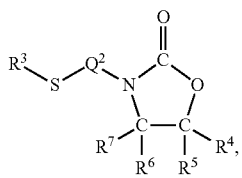

wherein C, N, O, S, R³, and Q² are the same as those defined in general formula (2^A) shown above; and R⁴, R⁵, R⁶, and R⁷ are the same as those defined in general formula (1^B) shown above. Meanwhile, in a more preferred mode, the compound represented by general formula (2^A) specifically may be a compound represented by general formula (2^A) shown above, in which each of Q¹ and Q² is a 1,2-ethanediyl group, i.e., a compound represented by the following general formula (2^C):

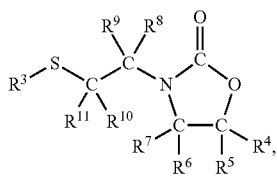

wherein C, N, O, S, R³, and Q² are the same as those defined in general formula (2^A) shown above; and R⁴, R⁵, R⁶, R⁷, R⁸, R⁹, R¹⁰, and R¹¹ are the same as those defined in general formula (1^D) shown above.

In addition, the compound represented by general formula (3^A) can be obtained easily by reacting a compound represented by the following general formula (7):

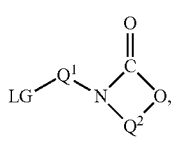

wherein C, N, O, Q¹ and Q² are the same as those defined in general formula (3^A) shown above; and LG represents a leaving group, with the compound represented by general formula (4) under a basic condition. Note that, in a preferred mode, the compound represented by general formula (3^A) specifically may be a compound represented by general formula (3^A) shown above, in which Q² is a 1,2-ethanediyl group, i.e., a compound represented by the following general formula (3^B)

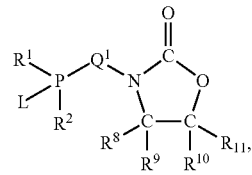

wherein C, N, O, P, L, R¹, R², and Q¹ are the same as those defined in general formula (3^A) shown above; and R³, R⁹, R¹⁰, and R¹¹ are the same as those defined in general formula (1^C) shown above. In addition, in a more preferred mode, the compound represented by general formula (3^A) specifically may be a compound represented by general formula (3^A) shown above, in which each of Q¹ and Q² is a 1,2-ethanediyl group, i.e., a compound represented by the following general formula (3^C):

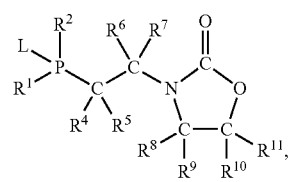

wherein C, N, O, P, L, R¹ and R² are the same as those defined in general formula (3^A) shown above; and R⁴, R⁵, R⁶, R⁷, R⁸, R⁹, R¹⁰, and R¹¹ are the same as those defined in general formula (1^D) shown above.

LG in each of general formula (6) and general formula (7) represents a leaving group, and preferably represents a halogeno group or a pseudohalogeno group. Specifically, the halogeno group may be a fluoro group, a chloro group, a bromo group, or an iodo group, and a preferred specific example is a chloro group. Specifically, the pseudohalogeno group may be a methanesulfonyloxy group, a p-toluenesulfonyloxy group, a trifluoromethanesulfonyloxy group, a n-nonafluorobutanesulfonyloxy group, or the like.

Next, a method for producing the compound of the present invention is described in detail. The compound of the present invention can be produced easily by reacting the compound represented by general formula (2^A) with the compound represented by general formula (4) or by reacting the compound represented by general formula (3^A) with the compound represented by general formula (5). First, the reaction of the compound represented by general formula (2^A) with the compound represented by general formula (4) is described in further detail (Eq. 2):

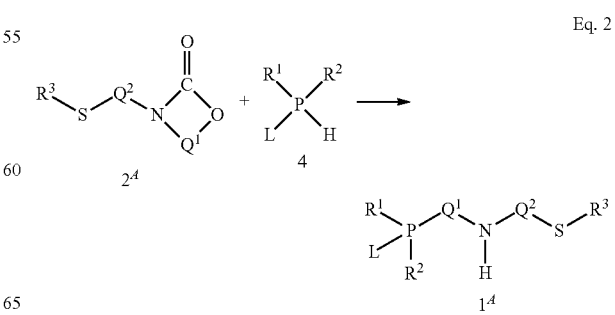

Eq. 2

The compound represented by general formula (4) is described in further detail based on specific examples. Specifically, the compound represented by general formula (4) may be a secondary phosphine or a boron trihydride complex of a secondary phosphine. Specific examples of the secondary phosphine include dimethylphosphine (4-1), diethylphosphine (4-2), diisopropylphosphine (4-3), di-tert-butylphosphine (4-4), dicyclopentylphosphine (4-5), dicyclohexylphosphine (4-6), diphenylphosphine (4-7), bis(2-methylphenyl)phosphine (4-8), bis(4-methylphenyl)phosphine (4-9), bis(3,5-dimethylphenyl)phosphine (4-10), bis(2,4,6-trimethylphenyl)phosphine (4-11), bis(2-methoxyphenyl)phosphine (4-12), bis(4-methoxyphenyl)phosphine (4-13), bis(4-trifluoromethylphenyl)phosphine (4-14), bis[3,5-bis(trifluoromethyl)phenyl]phosphine (4-15), bis(3,5-di-tert-butyl-4-methoxyphenyl)phosphine (4-16), tert-butylphenylphosphine (4-17), di-1-adamantylphosphine (4-18), (11bS)-4,5-dihydro-3H-dinaphtho[2,1-c:1',2'-e]phosphepine (4-19), di-2-furylphosphine (4-20), and the like, and a preferred specific example is diphenylphosphine (4-7). Specific examples of the secondary phosphine-boron trihydride complex include boron trihydride complexes of the secondary phosphines listed as specific examples above, and preferred specific examples thereof include dicyclohexylphosphine-boron trihydride complex (4-21), and the like.

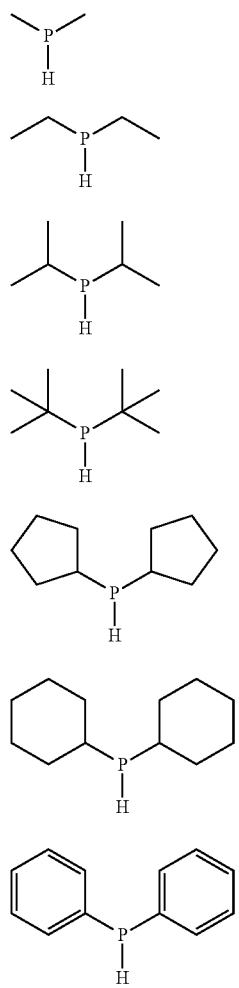

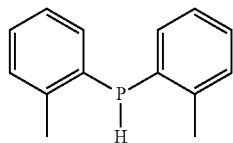

4-8

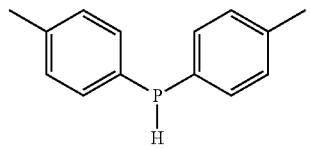

4-9

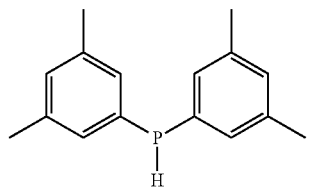

4-10

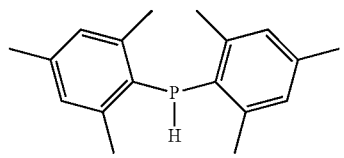

4-11

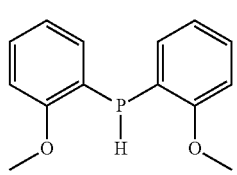

4-12

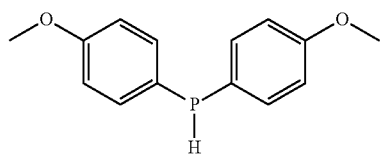

4-13

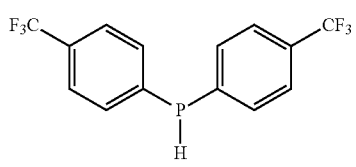

4-14

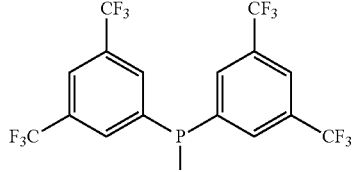

4-15

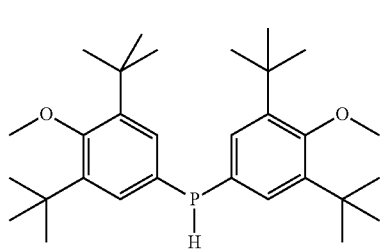

4-16

4-17

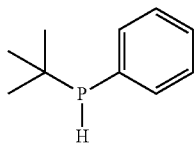

4-18

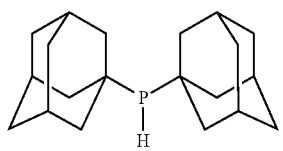

4-19

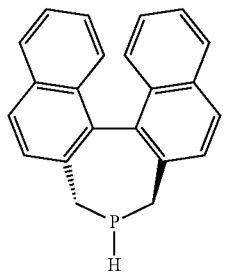

4-20

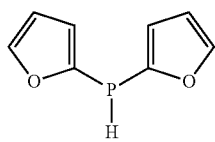

4-21

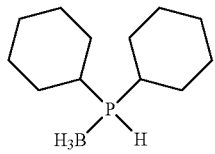

Some of these secondary phosphines are unstable in air. Hence, to facilitate the handling, a salt may be formed with a Bronsted acid, specifically, with tetrafluoroboric acid, for example. The Bronsted acid salt of the secondary phosphine may be used for the reaction after the secondary phosphine is liberated by a treatment with a base outside the reaction system, or may be used for the reaction while the secondary phosphine is being liberated by a treatment with a base in the reaction system. In addition, a secondary phosphide or a boron trihydride complex of a secondary phosphide may be used for this reaction instead of the compound represented by general formula (4). The secondary phosphide and the boron trihydride complex of a secondary phosphide can be prepared easily by reacting the compound represented by general formula (4) with a base. The secondary phosphide can also be prepared easily by other reactions, and specific example of the reactions include a reaction of a secondary phosphine halide with an alkali metal, a reaction of a secondary phosphine dimer with an alkali metal, a reaction of a tertiary phosphine with an alkali metal, and the like.

The amount of each of the compound represented by general formula (4), the secondary phosphide, and the boron trihydride complex of a secondary phosphide used is not particularly limited, and is selected, as appropriate, from the range of generally 0.4 to 2 equivalents, preferably 0.6 equivalents to 1.5 equivalents, and more preferably 0.8 to 1.2 equivalents to the compound represented by general formula ($2^{A}$), in general.

This reaction can be carried out under an acidic condition or a basic condition. It is more preferable to carry out the reaction under a basic condition. When a secondary phosphide or a boron trihydride complex of a secondary phosphide is used instead of the compound represented by general formula (4), this reaction is preferably carried out under a neutral condition or a basic condition.

When this reaction is carried out under an acidic condition, specific preferred acids include trifluoromethanesulfonic acid and the like.

When this reaction is carried out under a basic condition, preferred specific bases include alkali metal hydroxides such as lithium hydroxide, sodium hydroxide, and potassium hydroxide, alkaline earth metal hydroxides such as calcium hydroxide, strontium hydroxide, and barium hydroxide, metal hydrides such as lithium hydride, sodium hydride, potassium hydride, calcium hydride, sodium borohydride, and lithium aluminum hydride, alkali metal alkoxides such as lithium methoxide, sodium methoxide, potassium methoxide, sodium ethoxide, potassium ethoxide, sodium tert-butoxide, and potassium tert-butoxide, organolithium compounds such as methyllithium, n-butyllithium, sec-butyllithium, tert-butyllithium, and phenyllithium, alkali metal amides such as lithiumamide, sodium amide, lithium diisopropyl amide, and lithium hexamethyldisilazide, Grignard reagents such as methylmagnesium chloride, tert-butylmagnesium chloride, phenylmagnesium chloride, phenylmagnesium bromide, and methylmagnesium iodide, and the like. A particularly preferred specific example is n-butyllithium. Each of the bases may be used alone, or two or more of these bases may be used in combination, as appropriate.

The amount of the base used is not particularly limited, and is selected, as appropriate, from the rage of generally 0.3 to 10 equivalents, preferably 0.5 to 5 equivalents, and more preferably 0.8 to 3 equivalents to the compound represented by general formula (4). Note that, in this reaction, a method for adding the base is not particularly limited, and each of the compound represented by general formula (4) and the base may be added separately. Alternatively, a mixture of the compound represented by general formula (4) and the base (and a solvent) may be added, or the secondary phosphide obtainable by reacting the compound represented by general formula (4) with the base (in a solvent) or the boron trihydride complex of the secondary phosphide may be added.

This reaction is preferably carried out in the presence of a solvent. Specifically, the solvent may be an aliphatic hydrocarbon such as n-pentane, n-hexane, n-heptane, n-octane, n-decane, cyclohexane, or decalin, an aromatic hydrocarbon such as benzene, toluene, xylene, mesitylene, p-cymene, or 1,4-diisopropylbenzene, a monoalcohol such as methanol, ethanol, 2-propanol, n-butanol, tert-butanol, 2-methyl-2-butanol, or 2-ethoxyethanol, a polyol such as ethylene glycol, propylene glycol, 1,2-propanediol, or glycerin, an ether such as diethyl ether, diisopropyl ether, tert-butyl methyl ether, cyclopentyl methyl ether, dimethoxyethane, ethylene glycol diethyl ether, tetrahydrofuran, or 1,4-dioxane, an amine such as triethylamine, aniline, or 2-phenethylamine, or the like. Preferred specific examples thereof include n-hexane, tetrahydrofuran, and the like. Each of these solvents may be used alone, or two or more thereof may be used, as appropriate, in combination.

The amount of the solvent used is not particularly limited, and is selected, as appropriate, from the range of generally 1 to 200 times by volume, preferably 2 to 100 times by volume, and more preferably 5 to 50 times by volume of that of the compound represented by general formula ($2^{A}$).

This reaction is preferably performed in an inert gas atmosphere. Specifically, the inert gas may be argon gas, nitrogen gas, or the like. The reaction temperature is selected, as appropriate, from the range of generally −78 to 150° C., preferably −40 to 100° C., and more preferably 0 to 75° C. The reaction time naturally varies depending on the base, the solvent, the reaction temperature, and other conditions, and is selected, as appropriate, from the range of generally 1 minute to 48 hours, preferably 5 minutes to 24 hours, and more preferably 10 minutes to 8 hours.

By reacting the compound represented by general formula ($2^B$) with the compound represented by general formula (4) using this production method, the compound represented by general formula ($1^B$) can be produced similarly. In addition, by reacting the compound represented by general formula ($2^C$) with the compound represented by general formula (4), the compound represented by general formula ($1^D$) can be produced similarly (Eq. 3).

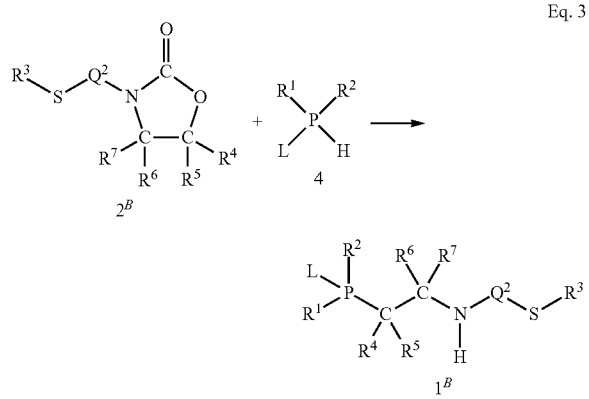

Eq. 3

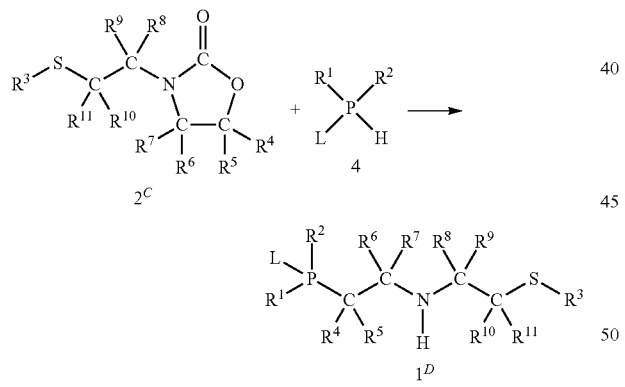

Next, the reaction of the compound represented by general formula ($3^A$) with the compound represented by general formula (5) is described in detail (Eq. 4).

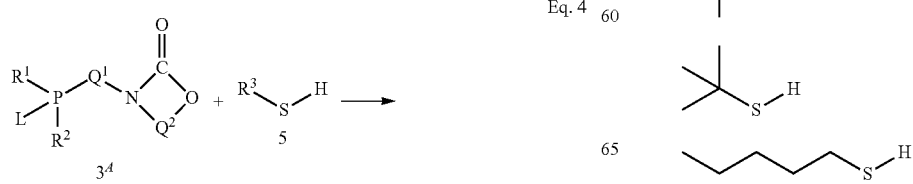

Eq. 4

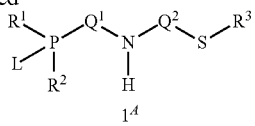

$1^A$

The compound represented by general formula (5) is described in further detail based on specific examples. Specifically, the compound represented by general formula (5) may be a thiol. Specific examples of the thiol include methanethiol (5-1), ethanethiol (5-2), 1-propanethiol (5-3), 2-propanethiol (5-4), 1-butanethiol (5-5), 2-butanethiol (5-6), 2-methyl-1-propanethiol (5-7), 2-methyl-2-propanethiol (5-8), 1-pentanethiol (5-9), 3-methyl-1-butanethiol (5-10), cyclopentanethiol (5-11), 1-hexanethiol (5-12), cyclohexanethiol (5-13), 1-heptanethiol (5-14), 1-octanethiol (5-15), 1-nonanethiol (5-16), 1-decanethiol (5-17), 1-adamantanethiol (5-18), benzenethiol (5-19), o-toluenethiol (5-20), m-toluenethiol (5-21), p-toluenethiol (5-22), 2,4-dimethylbenzenethiol (5-23), 2,5-dimethylbenzenethiol (5-24), 3,4-dimethylbenzenethiol (5-25), 3,5-dimethylbenzenethiol (5-26), 4-isopropylbenzenethiol (5-27), 4-tert-butylbenzenethiol (5-28), 2-methoxybenzenethiol (5-29), 4-methoxybenzenethiol (5-30), 2,5-dimethoxybenzenethiol (5-31), 3,4-dimethoxybenzenethiol (5-32), 2-fluorobenzenethiol (5-33), 3-fluorobenzenethiol (5-34), 4-fluorobenzenethiol (5-35), 2-chlorobenzenethiol (5-36), 4-chlorobenzenethiol (5-37), biphenyl-4-thiol (5-38), 1-naphthalenethiol (5-39), benzyl mercaptan (5-40), (2,4,6-trimethylphenyl)methanethiol (5-41), (4-methoxyphenyl)methanethiol (5-42), (4-fluorophenyl)methanethiol (5-43), (2-chlorophenyl)methanethiol (5-44), (4-chlorophenyl)methanethiol (5-45), triphenylmethanethiol (5-46), 9-mercaptofluorene (5-47), and the like, and preferred specific examples thereof include 1-adamantanethiol (5-18) and the like.

5-1

5-2

5-3

5-4

5-5

5-6

5-7

5-8

5-9

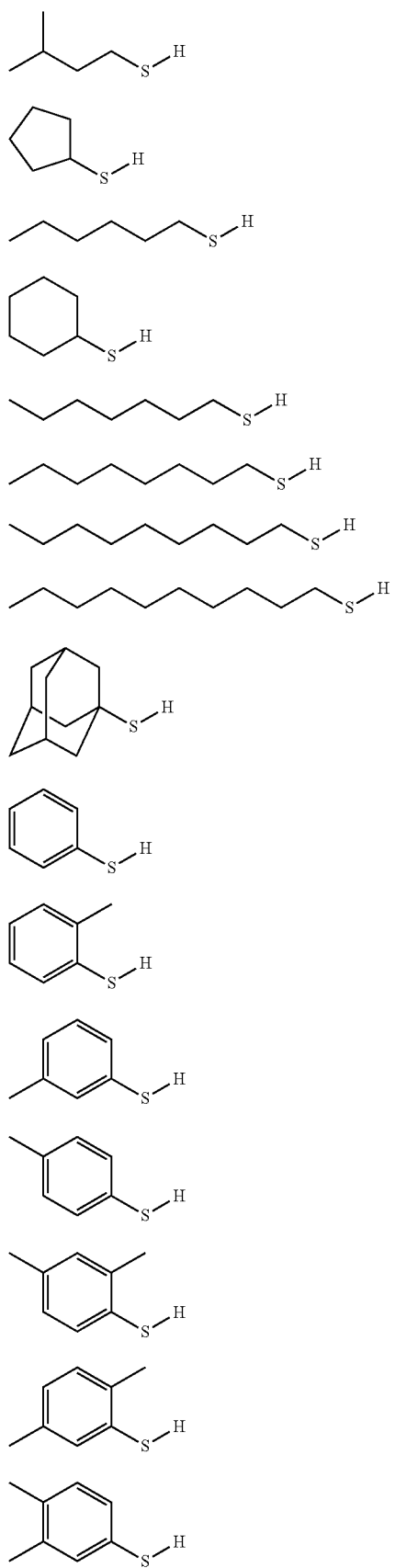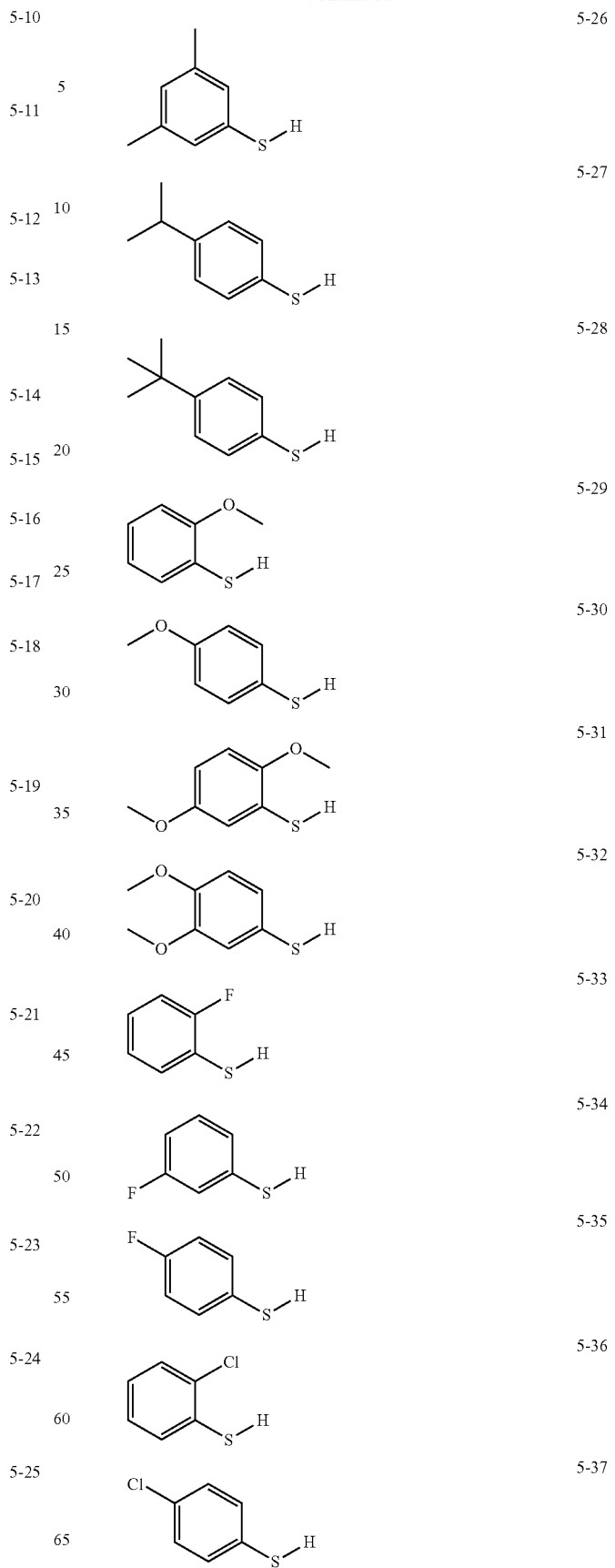

-continued

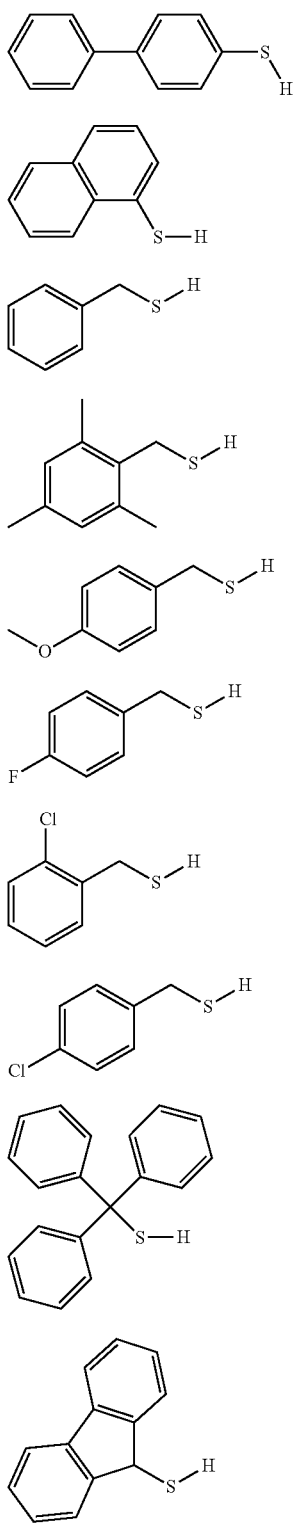

5-38

5-39

5-40

5-41

5-42

5-43

5-44

5-45

5-46

5-47

In this reaction, it is also possible to use a salt of the thiol (thiolate) easily obtainable by reacting the compound represented by general formula (5) with a base, instead of the compound represented by general formula (5). Specific examples of the thiolate include alkali metal salts of the above-described thiols listed as the specific examples, and the like, and preferred specific examples thereof include sodium salt of methanethiol (5-1) (sodium methanethiolate), sodium salt of ethanethiol (5-2) (sodium ethanethiolate), sodium salt of 2-methyl-2-propanethiol (5-8) (sodium 2-methyl-2-propanethiolate), sodium salt of benzenethiol (5-19) (sodium benzenethiolate), sodium salt of p-toluenethiol (5-22) (sodium p-toluenethiolate), and the like.

This reaction can be carried out under an acidic condition or a basic condition, and is more preferably carried out under a basic condition. In addition, when a thiolate is used instead of the compound represented by general formula (5), this reaction is preferably carried out under a neutral condition or a basic condition. When this reaction is carried out under a basic condition, specific preferred bases include alkali metal hydroxides such as lithium hydroxide, sodium hydroxide, and potassium hydroxide, alkali metal phosphates such as sodium phosphate and potassium phosphate, alkali metal carbonates such as lithium carbonate, sodium carbonate, and potassium carbonate, alkali metal carboxylates such as sodium acetate and potassium acetate, alkaline earth metal hydroxides such as calcium hydroxide, strontium hydroxide, and barium hydroxide, metal hydrides such as lithium hydride, sodium hydride, potassium hydride, calcium hydride, sodium borohydride, and lithium aluminum hydride, alkali metal alkoxide such as lithium methoxide, sodium methoxide, potassium methoxide, sodium ethoxide, potassium ethoxide, sodium tert-butoxide, and potassium tert-butoxide, organolithium compounds such as methyllithium, n-butyllithium, sec-butyllithium, tert-butyllithium, and phenyllithium, alkali metal amides such as lithium amide, sodium amide, lithium diisopropyl amide, and lithium hexamethyldisilazide, Grignard reagents such as methylmagnesium chloride, tert-butylmagnesium chloride, phenylmagnesium chloride, phenylmagnesium bromide, and methylmagnesium iodide, amines such as triethylamine, tri-n-butylamine, diisopropylethylamine, N,N-dimethylaniline, 4-dimethylaminopyridine, pyrrolidine, piperidine, N-methylmorpholine, 1,5-diazabicyclo[4.3.0]non-5-ene, and 1,8-diazabicyclo[5.4.0]undec-7-ene, and the like, and a preferred specific example thereof is sodium tert-butoxide. Each of these bases may be used alone, or two or more thereof may be used, as appropriate, in combination.

The amount of the base used is not particularly limited, and is selected, as appropriate, from the range of generally 0.3 to 10 equivalents, preferably 0.5 to 5 equivalents, and more preferably 0.8 to 3 equivalents to the compound represented by general formula (5). Note that a method for adding the base in this reaction is not particularly limited, and each of the compound represented by general formula (5) and the base may be added separately. Alternatively, a mixture of the compound represented by general formula (5) and the base (and a solvent) may be added, or the thiolate obtained by reacting the compound represented by general formula (5) with the base (in a solvent) may be added.

This reaction is preferably carried out in the presence of a solvent. Specifically, the solvent may be an aliphatic hydrocarbon such as n-pentane, n-hexane, n-heptane, n-octane, n-decane, cyclohexane, or decalin, an aromatic hydrocarbon such as benzene, toluene, xylene, mesitylene, p-cymene, or 1,4-diisopropylbenzene, a halogenated aromatic hydrocarbon such as chlorobenzene or o-dichlorobenzene, an alcohol such as methanol, ethanol, 2-propanol, n-butanol, tert-butanol, 2-methyl-2-butanol, or 2-ethoxyethanol, a polyol such as ethylene glycol, propylene glycol, 1,2-propanediol, or glycerin, an ether such as diethyl ether, diisopropyl ether, tert-butyl methyl ether, cyclopentyl methyl ether, dimethoxyethane, ethylene glycol diethyl ether, tetrahydrofuran, or 1,4-dioxane, an ester such as methyl acetate, ethyl acetate, n-butyl acetate, or methyl propionate, a ketone such as acetone, methyl ethyl ketone, methyl isobutyl ketone, or cyclohexanone, an amine such as triethylamine, aniline or phenethylamine, an amide such as formamide, N,N-dimethylformamide, or N,N-dimethylacetamide, a nitrile such as acetonitrile, malononitrile, or benzonitrile, a sulfoxide such as dimethyl sulfoxide, water, or the like, and a preferred specific example thereof is 2-methyl-2-butanol. Each of these solvents may be used alone, or two or more thereof may be used, as appropriate, in combination.

The amount of the solvent used is not particularly limited, and is selected, as appropriate, from the range of generally 0.5 to 100 times by volume, preferably 1 to 40 times by volume, and more preferably 2 to 20 times by volume of that of the compound represented by general formula ($3^A$).

This reaction is preferably performed in an inert gas atmosphere. Specifically, the inert gas may be argon gas, nitrogen gas, or the like. The reaction temperature is selected, as appropriate, from the range of generally 25 to 200° C., preferably 50 to 175° C., and more preferably 75 to 150° C. The reaction time naturally varies depending on the base, the solvent, the reaction temperature, and other conditions, and is selected, as appropriate, from the range of generally 1 minute to 24 hours, preferably 2 minutes to 12 hours, and more preferably 5 minutes to 8 hours.

By reacting the compound represented by general formula ($3^B$) with the compound represented by general formula (5) using this production method, the compound represented by general formula ($1^C$) can be produced similarly. In addition, by reacting the compound represented by general formula ($3^C$) with the compound represented by general formula (5), the compound represented by general formula ($1^D$) can be produced similarly (Eq. 5).

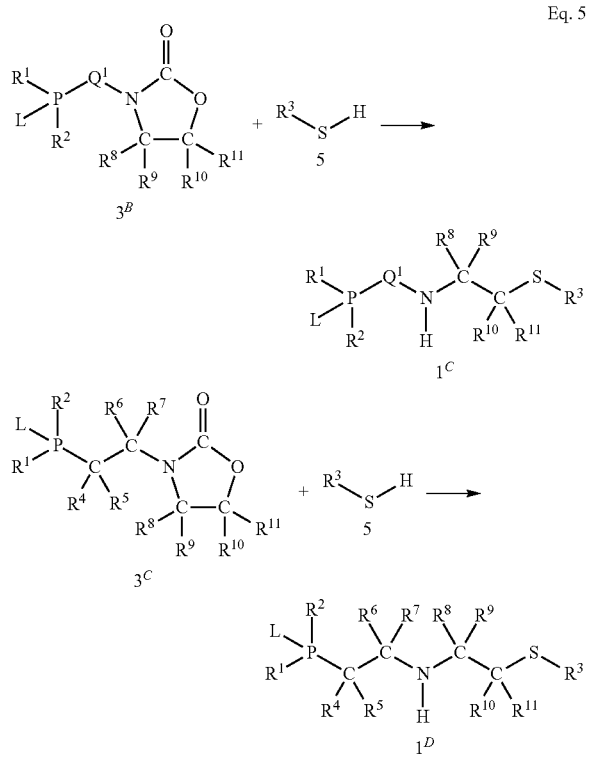

If necessary, the thus obtained compound of the present invention may be subjected to post treatments, isolation, and purification. Examples of methods for the post treatments include concentration, solvent exchange, washing, extraction, back-extraction, filtration, crystallization by adding a poor solvent, formation of a salt by adding a Bronsted acid, and the like. These methods can be performed alone or in combination. Examples of methods for the isolation or purification include decolorization with an adsorbent, column chromatography, distillation, recrystallization, washing of crystals with a poor solvent, crystallization of a salt obtained by adding a Bronsted acid, and the like. These methods can be performed alone or in combination.

Next, the metal complex of the present invention is described in further detail. The metal species in the metal complex of the present invention is not particularly limited, as long as the compound of the present invention can coordinate to the metal species. From the viewpoint of the catalytic activities in organic synthesis reactions, the metal species is preferably selected from the group consisting of group 5 transition metals, group 6 transition metals, group 7 transition metals, group 8 transition metals, group 9 transition metals, group 10 transition metals, and group 11 transition metals. The metal species is more preferably a metal species selected from the group consisting of group 8 transition metals, group 9 transition metals, and group 10 transition metals, namely, iron, ruthenium, osmium, cobalt, rhodium, iridium, nickel, palladium, and platinum. The metal species is particularly preferably ruthenium. The valence of the metal species is not particularly limited either, as long as the compound of the present invention can coordinate to the metal species. For example, the valence is preferably +2 for a group 8 transition metal, the valence is preferably +3 for a group 9 transition metal, and the valence is preferably +2 for a group transition metal.

A preferred group 8 transition metal complex comprising the compound of the present invention as a ligand is a metal complex represented by compositional formula ($8^A$) shown above. Meanwhile, a preferred group 9 transition metal complex comprising the compound of the present invention as a ligand is a metal complex represented by compositional formula ($9^A$) shown above. Moreover, a preferred group 10 transition metal complex comprising the compound of the present invention as a ligand is a metal complex represented by compositional formula ($10^A$) shown above.

In each of compositional formulae ($8^A$), ($9^A$), and ($10^A$), $M^8$ represents a divalent group 8 transition metal ion selected from the group consisting of a divalent iron ion, a divalent ruthenium ion, and a divalent osmium ion, and preferably represents a divalent ruthenium ion. $M^9$ represents a trivalent group 9 transition metal ion selected from the group consisting of a trivalent cobalt ion, a trivalent rhodium ion, and a trivalent iridium ion, and $M^{10}$ represents a divalent group 10 transition metal ion selected from the group consisting of a divalent nickel ion, a divalent palladium ion, and a divalent platinum ion. $X^1$, $X^2$, and $X^3$ each independently represent a monoanionic monodentate ligand, and $L^1$, $L^2$, and $L^3$ each independently represent a neutral monodentate ligand; k, l, and m, which respectively represent the coordination numbers of $L^1$, $L^2$, and $L^3$, each independently represent an integer of 0 or 1; and PNS represents the compound of the present invention. When the total of k, l, and m in compositional formula ($8^A$) is an integer of 1 to 3, n in compositional formula ($8^A$) represents 0, whereas when the total is 0, n represents 1 or 2.

Next, $X^1$, $X^2$, and $X^3$, i.e., monoanionic monodentate ligands, in compositional formulae ($8^A$), ($9^A$), and ($10^A$) are described in detail. A monoanionic monodentate ligand refers to a functional group having a single negative charge and being capable of binding to a metal in a metal complex via a single bond, an anion capable of functioning as a counter ion to the metal complex, or a group simultaneously having characteristics of the both. Specifically, the monoanionic monodentate ligands (name as functional group/name as anion, followed by their general formulae in parentheses) include hydride group/hydride ion (—H/H$^-$), hydroxy group/hydroxide ion (—OH/HO$^-$), alkoxy groups/alkoxide ions (—OR/RO$^-$), aryloxy groups/aryloxide ions (—OAr/ArO$^-$), acyloxy groups/carboxylate ions (—OC(=O) R/RCO$_2^-$), hydrogen carbonate ion (HCO$_3^-$), mercapto group/hydrogen sulfide ion (—SH/HS$^-$), alkylthio groups/alkylthiolate ions (—SR/RS$^-$), arylthio groups/arylthiolate ions (—SAr/ArS$^-$), sulfonyloxy groups/sulfonate ions (—OSO$_2$R/RSO$_3^-$), thiocyanate ion (NCS$^-$), halogeno groups/halide ions (—X/X$^-$), hypochlorite ion (ClO$^-$), chlorite ion (ClO$_2^-$), chlorate ion (ClO$_3^-$), perchlorate ion (ClO$_4^-$), tetrahydroborate ion (BH$_4^-$), tetrafluoroborate ion (BF$_4^-$), tetraarylborate ions (BAr$_4^-$), dihydrogen phosphate ion (H$_2$PO$_4^-$), hexafluorophosphate ion (PF$_E^-$), hexafluoroantimonate ion (SbF$_6^-$), azido group/azide ion (—N$_3$/N$_3^-$), cyano group/cyanide ion (—CN/CN$^-$), nitro group/nitrite group/nitrite ion (—NO$_2$/—ONO/NO$_2^-$), nitrate ion (NO$_3^-$), hydrogen sulfate ion (HSO$_4^-$), tetrahydroxoaluminate ion ([Al(OH)$_4$]$^-$), tetrahydroxochromate ion ([Cr(OH)$_4$]$^-$), dicyanoargentate ion ([Ag(CN)$_2$]$^-$), chloroaurate ion ([AuCl$_4$]$^-$), and the like.

From the viewpoint of the catalytic activity of the metal complex of the present invention, preferred specific monoanionic monodentate ligands include hydride group/hydride ion, hydroxy group/hydroxide ion, alkoxy groups/alkoxide ions, aryloxy groups/aryloxide ions, acyloxy groups/carboxylate ions, sulfonyloxy groups/sulfonate ions, halogeno groups/halide ions, perchlorate ion, tetrahydroborate ion, tetrafluoroborate ion, tetraarylborate ions, hexafluorophosphate ion, hexafluoroantimonate ion, and the like, and more preferred specific monoanionic monodentate ligands include hydride group/hydride ion, halogeno groups/halide ions, tetrahydroborate ion, and the like.

The preferred monoanionic monodentate ligands are described in further detail. The alkoxy groups/alkoxide ions are, for example, alkoxy groups/alkoxide ions having 1 to 10 carbon atoms, and preferably alkoxy groups/alkoxide ions having 1 to 4 carbon atoms, and specifically include methoxy group/methoxide ion, ethoxy group/ethoxide ion, 1-propoxy group/1-propoxide ion, 2-propoxy group/2-propoxide ion, 1-butoxy group/1-butoxide ion, 2-butoxy group/2-butoxide ion, tert-butoxy group/tert-butoxide ion, and the like.

The aryloxy groups/aryloxide ions are, for example, aryloxy groups/aryloxide ions having 6 to 14 carbon atoms, and preferably aryloxy groups/aryloxide ions having 6 to 10 carbon atoms, and specifically include phenoxy group/phenoxide ion, p-methylphenoxy group/p-methylphenoxide ion, 2,4,6-trimethylphenoxy group/2,4,6-trimethylphenoxide ion, p-nitrophenoxy group/p-nitrophenoxide ion, pentafluorophenoxy group/pentafluorophenoxide ion, 1-naphthyloxy group/1-naphthyloxide ion, 2-naphthyloxy group/2-naphthyloxide ion, and the like.

The acyloxy groups/carboxylate ions are, for example, acyloxy groups/carboxylate ions having 1 to 18 carbon atoms, and preferably acyloxy groups/carboxylate ions having 1 to 6 carbon atoms, and specifically include formyloxy group/formate ion, acetoxy group/acetate ion, trifluoroacetoxy group/trifluoroacetate ion, propanoyloxy group/propionate ion, acryloyloxy group/acrylate ions, butanoyloxy group/butyrate ion, pivaloyloxy group/pivalate ion, pentanoyloxy group/valerate ion, hexanoyloxy group/caproate ion, benzoyloxy group/benzoate ion, pentafluorobenzoyloxy group/pentafluorobenzoate ion, and the like.

The sulfonyloxy groups/sulfonate ions are, for example, sulfonyloxy groups/sulfonate ions having 1 to 18 carbon atoms, and preferably sulfonyloxy groups/sulfonate ions having 1 to carbon atoms, and specifically include methanesulfonyloxy group/methanesulfonate ion, trifluoromethanesulfonyloxy group/trifluoromethanesulfonate ion, n-nonafluorobutanesulfonyloxy group/n-nonafluorobutanesulfonate ion, p-toluenesulfonyloxy group/p-toluenesulfonate ion, 10-camphorsulfonyloxy group/10-camphorsulfonate ion, and the like.

Specifically, the halogeno groups/halide ions include fluoro group/fluoride ion, chloro group/chloride ion, bromo group/bromide ion, and iodo group/iodide ion, and a preferred specific example is chloro group/chloride ion.

Specifically, the tetraarylborate ions include tetraphenylborate ion, tetrakis(pentafluorophenyl)borate ion, tetrakis[3,5-bis(trifluoromethyl)phenyl]borate ion, and the like.

In addition, none of these monoanionic monodentate ligands are present alone. Hence, when the metal complex of the present invention is produced, it is preferable to use the corresponding monoanionic monodentate ligand source, i.e., a conjugate acid derived from the monoanionic monodentate ligand or a salt derived from the monoanionic monodentate ligand.

Next, L$^1$, L$^2$, and L$^3$, i.e., neutral monodentate ligands, in compositional formulae (8$^A$), (9$^A$), and (10$^A$) are described in detail. A neutral monodentate ligand refers to an organic compound having at least one nonionic functional group capable of coordinating to a metal, and specific neutral monodentate ligands (generic name followed by general formula in parentheses) include water (H$_2$O), alcohols (ROH), ethers (ROR'), ketones (RC(=O) R'), esters (RC(=O) OR'), thiols (RSH), sulfides (RSR'), sulfoxides (RS(=O) R'), amines (RR'R"N), amides (RR'NC(=O)R"), nitriles (RCN), isonitriles (RNC), heteroarenes (HetArH), secondary phosphines (RR'PH), secondary phosphine oxides (RR'P(=O)H), tertiary phosphines (RR'R"P), phosphites ((RO) (R'O) (R"O)P), phosphoramidites ((RO) (R'O) PNR'"), tertiary arsines (RR'R"As), carbenes (RR'C:), nitrenes (RN::), silylenes (RR'Si:), hydrogen molecule (H$_2$), nitrogen molecule (N$_2$), carbon monoxide (CO), nitrogen monoxide (NO), and the like.

From the viewpoint of the catalytic activities of the metal complex of the present invention in organic synthesis reactions, preferred neutral monodentate ligands include alcohols, ethers, sulfides, sulfoxides, amines, amides, nitriles, isonitriles, heteroarenes, secondary phosphines, secondary phosphine oxides, tertiary phosphines, phosphites, phosphoramidites, tertiary arsines, carbenes, hydrogen molecule, and carbon monoxide, of which tertiary phosphines, phosphites, carbon monoxide, and the like are more preferable.

The preferred neutral monodentate ligands are described in further detail. Specifically, the alcohols include methanol, ethanol, 2-propanol, 2,2,2-trifluoroethanol, 1,1,1,3,3,3-hexafluoro-2-propanol, and the like.

Specifically, the ethers include dimethyl ether, diethyl ether, tetrahydrofuran, 1,4-dioxane, and the like.

Specifically, the sulfides include dimethyl sulfide, diethyl sulfide, diphenyl sulfide, tetrahydrothiophene, and the like.

Specifically, the sulfoxides include dimethyl sulfoxide, tetrahydrothiophene-1-oxide, and the like. Note that these sulfoxides may be coordinated to the metal species via either the sulfur atom or an oxygen atom on the sulfur atom.

Specifically, the amines include ammonia, methylamine, dimethylamine, trimethylamine, ethylamine, diethylamine, triethylamine, isopropylamine, aniline, benzylamine, α-phenethylamine, β-phenethylamine, piperazine, piperidine, morpholine, and the like.

Specifically, the amides include N,N-dimethylformamide, N,N-dimethylacetamide, and the like.

Specifically, the nitriles include acetonitrile, benzonitrile, and the like.

Specifically, the isonitriles include (trimethylsilyl)methyl isocyanide, isopropyl isocyanide, 1-butyl isocyanide, tert-butyl isocyanide, 1-pentyl isocyanide, 2-pentyl isocyanide, cyclohexyl isocyanide, 1,1,3,3-tetramethylbutyl isocyanide, 1-adamantyl isocyanide, 2,6-dimethylphenyl isocyanide, 4-methoxyphenyl isocyanide, 2-naphthyl isocyanide, benzyl isocyanide, a-methylbenzyl isocyanide, and the like, and preferred specific examples thereof include 4-methoxyphenyl isocyanide and the like.

Specifically, the heteroarenes include furan, benzofuran, isobenzofuran, thiophene, thianaphthene, isothianaphthene, pyridine, quinoline, isoquinoline, 3H-pyrrole, 3H-indole, 2H-pyrrole, 1H-isoindole, oxazole, oxazoline, benzoxazole, isoxazole, isoxazoline, benzisoxazole, thiazole, thiazoline, benzothiazole, isothiazole, isothiazoline, benzisothiazole, imidazole, imidazoline, benzimidazole, pyrazole, 2-pyrazoline, indazole, and the like.

Specifically, the secondary phosphines include the same compounds as the secondary phosphines listed as the specific examples of the compound represented by general formula (4).

Specifically, the secondary phosphine oxides include dimethylphosphine oxide, diethylphosphine oxide, diisopropylphosphine oxide, di-tert-butylphosphine oxide, dicyclopentylphosphine oxide, dicyclohexylphosphine oxide, diphenylphosphine oxide, bis(2-methylphenyl)phosphine oxide, bis(4-methylphenyl)phosphine oxide, bis(3,5-dimethylphenyl)phosphine oxide, bis(2,4,6-trimethylphenyl)phosphine oxide, bis(2-methoxyphenyl)phosphine oxide, bis(4-methoxyphenyl)phosphine oxide, bis(4-trifluoromethylphenyl)phosphine oxide, bis[3,5-bis(trifluoromethyl)phenyl]phosphine oxide, bis(3,5-di-tert-butyl-4-methoxyphenyl)phosphine oxide, tert-butylphenylphosphine oxide, di-1-adamantylphosphine oxide, (11bS)-4,5-dihydro-3H-dinaphtho[2,1-c:1',2'-e]phosphepine-4-oxide, di-2-furylphosphine oxide, and the like. Note that each of these secondary phosphine oxides may be coordinated to the metal species via either the phosphorus atom or the oxygen atom on the phosphorus atom.

The tertiary phosphines are compounds represented by the following general formula (11):

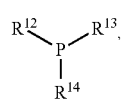

11 wherein P represents a phosphorus atom; $R^{12}$, $R^{13}$, and $R^{14}$ each independently represent a group selected from the group consisting of alkyl groups, optionally substituted alkenyl groups, optionally substituted aryl groups, optionally substituted heteroaryl groups, and optionally substituted aralkyl groups; and any ones of $R^{12}$ to $R^{14}$ may be bonded to each other to form an optionally substituted ring.

In general formula (11), P represents a phosphorus atom. $R^{12}$, $R^{13}$, and $R^{14}$ each independently represent a group selected from the group consisting of alkyl groups, optionally substituted alkenyl groups, optionally substituted aryl groups, optionally substituted heteroaryl groups, and optionally substituted aralkyl groups, and preferably represent a group selected from the group consisting of alkyl groups, optionally substituted aryl groups, and optionally substituted heteroaryl groups.

The alkyl groups may be linear, branched, or cyclic, and are, for example, alkyl groups having 1 to 30 carbon atoms, preferably alkyl groups having 1 to 20 carbon atoms, and more preferably alkyl groups having 1 to 10 carbon atoms. Specifically, the alkyl groups include a methyl group, an ethyl group, a n-propyl group, a 2-propyl group, a cyclopropyl group, a n-butyl group, a 2-butyl group, an isobutyl group, a tert-butyl group, a cyclobutyl group, a n-pentyl group, a 2-pentyl group, a 3-pentyl group, a tert-pentyl group, a 2-methylbutyl group, a 3-methylbutyl group, a 2-methylbutan-3-yl group, a 2,2-dimethylpropyl group, a cyclopentyl group, a n-hexyl group, a 2-hexyl group, a 3-hexyl group, a tert-hexyl group, a 2-methylpentyl group, a 3-methylpentyl group, a 4-methylpentyl group, a 2-methylpentan-3-yl group, a 2-methylpentan-4-yl group, a 3-methylpentan-2-yl group, a 3-methylpentan-3-yl group, a 2,2-dimethylbutyl group, a 3,3-dimethylbutyl group, a 2,2-dimethylbutan-3-yl group, a cyclohexyl group, a n-heptyl group, a n-octyl group, a n-nonyl group, a n-decyl group, a 1-adamantyl group, a 2-adamantyl group, and the like, and preferred specific examples thereof include a methyl group, an ethyl group, and a cyclohexyl group.

The alkenyl groups may be linear, branched, or cyclic, and are, for example, alkenyl groups having 2 to 20 carbon atoms, preferably alkenyl groups having 2 to 14 carbon atoms, and more preferably alkenyl groups having 2 to 8 carbon atoms. Specifically, the alkenyl groups include a vinyl group, a 1-propenyl group, a 2-propenyl group, an allyl group, a 1-cyclohexenyl group, a 1-styryl group, a 2-styryl group, and the like.

The aryl groups are, for example, aryl groups having 6 to 18 carbon atoms, preferably aryl groups having 6 to 14 carbon atoms, and more preferably aryl groups having 6 to 10 carbon atoms. Specifically, the aryl groups include a phenyl group, a 1-naphthyl group, a 2-naphthyl group, and the like, and a preferred specific example thereof is a phenyl group.

The heteroaryl groups includes heteroaryl groups derived from aromatic heterocycles each having a 5 to 6-membered ring and containing 1 to 4 heteroatoms selected from the group consisting of nitrogen atoms, oxygen atoms, and sulfur atoms and heteroaryl groups derived from polycyclic aromatic heterocycles formed by fusion of the aromatic heterocycles with the above-described aryl groups. Specifically, the heteroaryl groups includes a 2-furyl group, a 3-furyl group, a 2-thienyl group, a 3-thienyl group, a 2-benzofuryl group, a 3-benzofuryl group, a 2-benzothienyl group, a 3-benzothienyl group, and the like, and a preferred specific example is a 2-furyl group.

The aralkyl groups include aralkyl groups each formed by substitution of at least one hydrogen atom of one of the above-described alkyl groups with one of the above-described aryl groups, and polycyclic aralkyl groups each formed by fusion of one of the cyclic alkyl groups with one of the above-described aryl groups. Specifically, the aralkyl groups include a benzyl group, a 1-phenylethyl group, a 2-phenylethyl group, a 1-phenylpropyl group, a 2-phenylpropyl group, a 3-phenylpropyl group, a 1-phenyl-2-propyl group, a 2-phenyl-2-propyl group, a 1-indanyl group, a 2-indanyl group, a 9-fluorenyl group, and the like.

Any ones of $R^{12}$ to $R^{14}$ may be bonded to each other to form an optionally substituted ring. Specific examples of the ring include a phospholane ring, a phosphole ring, a phosphinane ring, a phosphinine ring, and the like.

Substituents which may be present on the alkenyl groups, the aryl groups, the heteroaryl groups, and the aralkyl groups serving as $R^{12}$ to $R^{14}$ and on the ring formed when any ones of $R^{12}$ to $R^{14}$ are bonded to each other include alkyl groups, halogenoalkyl groups, alkenyl groups, aryl groups, heteroaryl groups, aralkyl groups, hydroxy groups, alkoxy groups, alkoxycarbonyl groups, carboxyl groups, amino groups, sulfo groups, halogeno groups, and the like. Of these substituents, the alkyl groups, alkenyl groups, aryl groups, heteroaryl groups, and aralkyl groups are the same as the groups in the detailed description of $R^{12}$ to $R^{14}$.

The halogenoalkyl groups include groups which are the same as the above-described alkyl groups, except that at least one hydrogen atom is replaced with a halogen atom. Specifically, the halogenoalkyl groups include a trifluoromethyl group, a n-nonafluorobutyl group, and the like, and a preferred specific example thereof is a trifluoromethyl group.

The alkoxy groups are, for example, alkoxy groups having 1 to 10 carbon atoms, and preferably alkoxy groups having 1 to 4 carbon atoms. Specifically, the alkoxy groups include a methoxy group, an ethoxy group, a 1-propoxy group, a 2-propoxy group, a 1-butoxy group, a 2-butoxy group, a tert-butoxy group, and the like, and a preferred specific example thereof is a methoxy group.

Specifically, the alkoxycarbonyl groups include a methoxycarbonyl group and the like.

Specifically, the amino groups include a dimethylamino group, a 4-morpholinyl group, and the like.

Specifically, the halogeno groups include a fluoro group, a chloro group, a bromo group, and an iodo group, and preferred halogeno groups include a fluoro group and a chloro group.

Preferred specific examples of the tertiary phosphines represented by general formula (11) include trimethylphosphine (11-1), triethylphosphine (11-2), tricyclohexylphosphine (11-3), triphenylphosphine (11-4), tris(4-trifluoromethylphenyl)phosphine (11-5), tris(4-methoxyphenyl)phosphine (11-6), tris(2-furyl)phosphine (11-7), and the like.

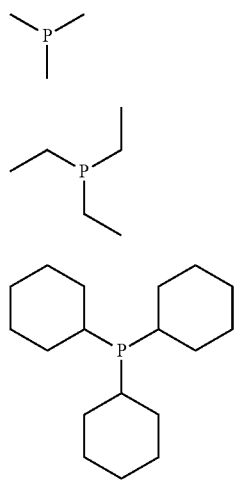

11-1

11-2

11-3

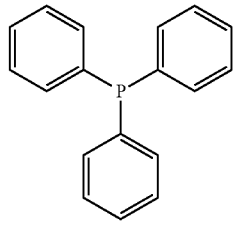

11-4

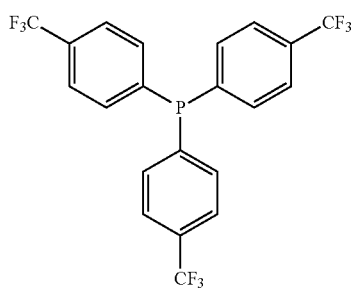

11-5

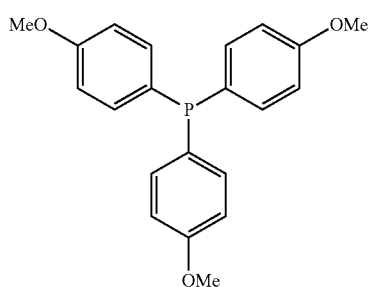

11-6

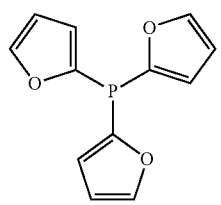

11-7

Specifically, the phosphites include trimethyl phosphite, triethyl phosphite, tris(2,2,2-trifluoroethyl) phosphite, triisopropyl phosphite, triphenyl phosphite, 4-ethyl-2,6,7-trioxa-1-phosphabicyclo[2,2,2]octane, and the like, and preferred specific examples thereof include 4-ethyl-2,6,7-trioxa-1-phosphabicyclo[2,2,2]octane and the like.

Specifically, the phosphoramidites include dimethyl N,N-diisopropylphosphoramidite, di-tert-butyl N,N-diethylphosphoramidite, dibenzyl N,N-dimethylphosphoramidite, and the like.

Specifically, the tertiary arsines include triphenylarsine, and the like.

The carbenes include linear, branched, or cyclic organic compounds each having a carbene carbon, i.e., a nonionic divalent carbon atom having six valence electrons in its molecule and being in a singlet state or a triplet state. From the viewpoint of the catalytic activities of the metal complex of the present invention in organic synthesis reactions, preferred carbenes include carbenes in a singlet state. Moreover, from the viewpoint of the chemical stability of the carbenes, more preferred carbenes include so-called N-heterocyclic carbenes in each of which a carbene carbon is included in a nitrogen-containing heterocyclic compound and which are in a singlet state.

Specifically, the N-heterocyclic carbenes include imidazol-4-ylidene, imidazol-4-ylidene, dihydroimidazol-2-ylidene, tetrahydropyrimidin-2-ylidene, hexahydro-1,3-diazepin-2-ylidene, oxazol-2-ylidene, dihydrooxazol-2-ylidene, thiazol-2-ylidene, dihydrothiazol-2-ylidene, pyrazolylidene, triazolylidene, pyridylidene, and the like.

N-Heterocyclic carbenes preferable from the viewpoint of synthesis include imidazol-2-ylidenes represented by the following general formula (12):

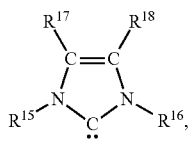

wherein the two dot leader represents lone pair electrons; C represents a carbon atom and N represents a nitrogen atom; $R^{15}$ and $R^{16}$ each independently represent a group selected from the group consisting of alkyl groups, optionally substituted alkenyl groups, optionally substituted aryl groups, and optionally substituted aralkyl groups; $R^{17}$ and $R^{18}$ each independently represent a group selected from the group consisting of a hydrogen atom, alkyl groups, optionally substituted alkenyl groups, optionally substituted aryl groups, and optionally substituted aralkyl groups; and any ones of $R^{15}$ to $R^{19}$ may be bonded to each other to form an optionally substituted ring, and dihydroimidazol-2-ylidenes represented by the following general formula (13):

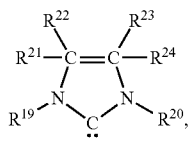

wherein the two dot leader represents lone pair electrons; C represents a carbon atom and N represents a nitrogen atom; $R^{19}$ and $R^{20}$ each independently represent a group selected from the group consisting of alkyl groups, optionally substituted alkenyl groups, optionally substituted aryl groups, and optionally substituted aralkyl groups; $R^{21}$, $R^{22}$, $R^{23}$, and $R^{24}$ each independently represent a group selected from the group consisting of a hydrogen atom, alkyl groups, optionally substituted alkenyl groups, optionally substituted aryl groups, and optionally substituted aralkyl groups; and any ones of $R^{19}$ to $R^{24}$ may be bonded to each other to form an optionally substituted ring.

In each of general formulae (12) and (13), the two dot leader represents lone pair electrons. C represents a carbon atom and N represents a nitrogen atom. $R^{15}$, $R^{16}$, $R^{19}$, and $R^{20}$ each independently represent a group selected from the group consisting of alkyl groups, optionally substituted alkenyl groups, optionally substituted aryl groups, and optionally substituted aralkyl groups. $R^{17}$, $R^{18}$, $R^{21}$, $R^{22}$, $R^{23}$, and $R^{24}$ each independently represent a group selected from the group consisting of a hydrogen atom, alkyl groups, optionally substituted alkenyl groups, optionally substituted aryl groups, and optionally substituted aralkyl groups. Any ones of $R^{15}$ to $R^{18}$ and $R^{19}$ to $R^{24}$ may be bonded to each other to form an optionally substituted ring.

The alkyl groups, alkenyl groups, aryl groups, and aralkyl groups serving as $R^{15}$ to $R^{24}$ are the same as the groups in the detailed description of $R^{12}$ to $R^{14}$ in general formula (11) shown above. Substituents which may be present on the alkenyl groups, aryl groups, and aralkyl groups serving as $R^{15}$ to $R^{24}$, the ring formed when any ones of $R^5$ to $R^{18}$ are bonded to each other, and the ring formed when any ones of $R^{19}$ to $R^{24}$ are bonded to each other include alkyl groups, halogenoalkyl groups, alkenyl groups, aryl groups, heteroaryl groups, aralkyl groups, hydroxy groups, alkoxy groups, amino groups, halogeno groups, and the like. These substituents are the same as the groups in the detailed description of the substituents which may be present on the alkenyl groups, aryl groups, heteroaryl groups, and aralkyl groups serving as $R^{12}$ to $R^{14}$ in general formula (11) shown above and on the ring formed when any ones of $R^{12}$ to $R^{14}$ in general formula (11) are bonded to each other.

Specific examples of the imidazol-2-ylidenes represented by general formula (12) include 1,3-dimethyl-2H-imidazol-2-ylidene (12-1), 1-ethyl-3-methyl-2H-imidazol-2-ylidene (12-2), 1,3-diisopropyl-2H-imidazol-2-ylidene (12-3), 1,3-di-tert-butyl-2H-imidazol-2-ylidene (12-4), 1,3-dicyclohexyl-2H-imidazol-2-ylidene (12-5), 1,3-bis(1-adamantyl)-2H-imidazol-2-ylidene (12-6), 1,3-dimethyl-2H-benzimidazol-2-ylidene (12-7), 1,3-di-tert-butyl-2H-benzimidazol-2-ylidene (12-8), 1,3-dicyclohexyl-2H-benzimidazol-2-ylidene (12-9), 1,3-bis(1-adamantyl)-2H-benzimidazol-2-ylidene (12-10), 1-methyl-3-(2,4,6-trimethylphenyl)-2H-benzimidazol-2-ylidene (12-11), 1,3-bis(2,6-diisopropylphenyl)-2H-imidazol-2-ylidene (12-12), 1,3-bis(2,4,6-trimethylphenyl)-2H-imidazol-2-ylidene (12-13), 1,3-bis[(1S)-2,2-dimethyl-1-(1-naphthyl)propyl]-2H-imidazol-2-ylidene (12-14), 2-(2,6-diisopropylphenyl)-5-methylimidazo[1,5-a]pyridin-1(2H)-ylidene (12-15), 2-(2,4,6-trimethylphenyl)-5-methylimidazo[1,5-a]pyridin-1(2H)-ylidene (12-16), 2-benzylimidazo[1,5-a]quinolin-1(2H)-ylidene (12-17), and the like.

12-1

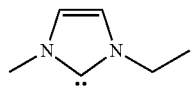

12-2

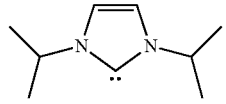

12-3

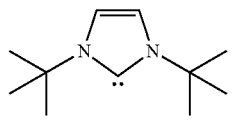

12-4

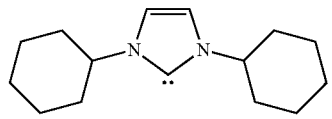

12-5

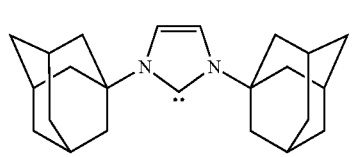

12-6

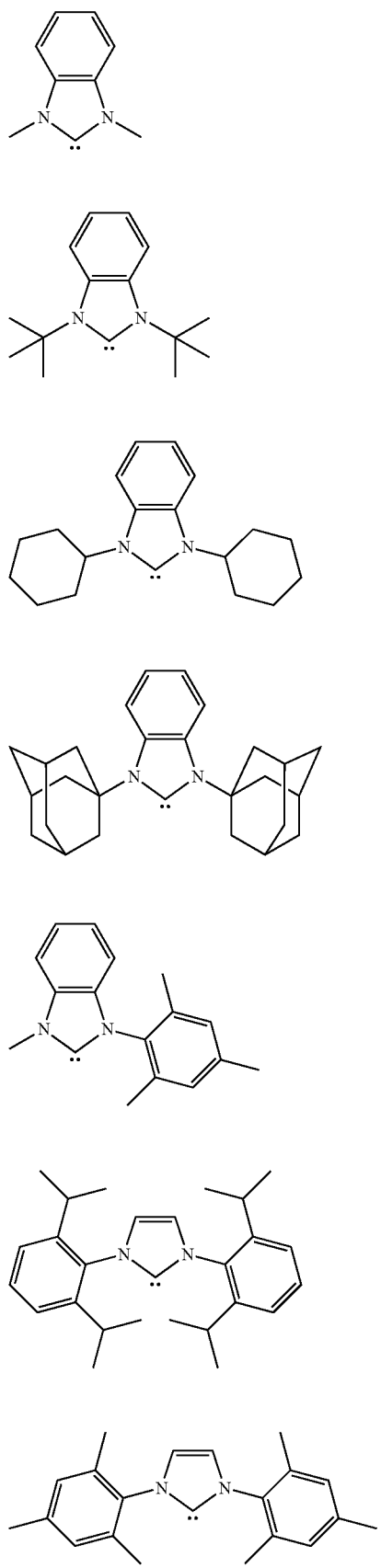

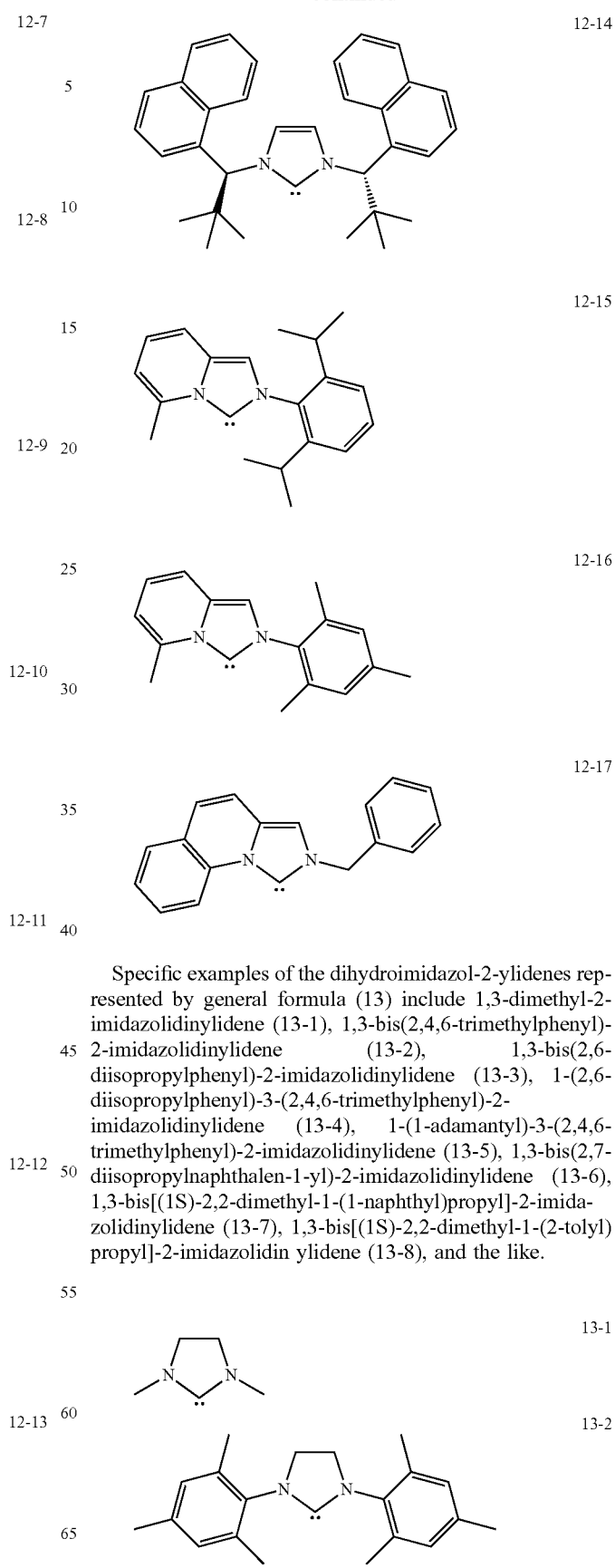

Specific examples of the dihydroimidazol-2-ylidenes represented by general formula (13) include 1,3-dimethyl-2-imidazolidinylidene (13-1), 1,3-bis(2,4,6-trimethylphenyl)-2-imidazolidinylidene (13-2), 1,3-bis(2,6-diisopropylphenyl)-2-imidazolidinylidene (13-3), 1-(2,6-diisopropylphenyl)-3-(2,4,6-trimethylphenyl)-2-imidazolidinylidene (13-4), 1-(1-adamantyl)-3-(2,4,6-trimethylphenyl)-2-imidazolidinylidene (13-5), 1,3-bis(2,7-diisopropylnaphthalen-1-yl)-2-imidazolidinylidene (13-6), 1,3-bis[(1S)-2,2-dimethyl-1-(1-naphthyl)propyl]-2-imidazolidinylidene (13-7), 1,3-bis[(1S)-2,2-dimethyl-1-(2-tolyl)propyl]-2-imidazolidin ylidene (13-8), and the like.

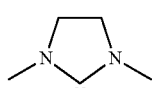

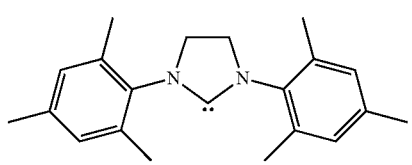

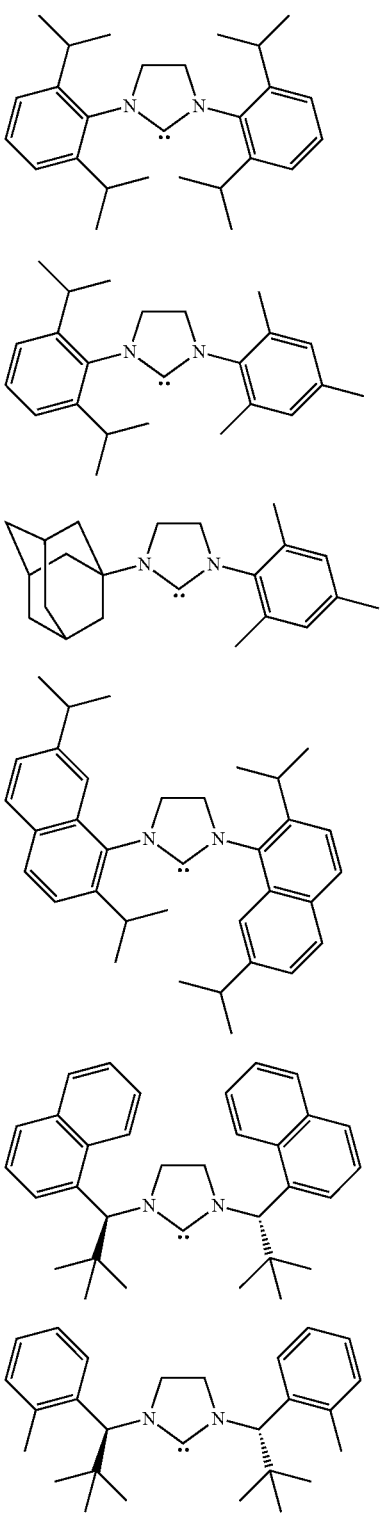

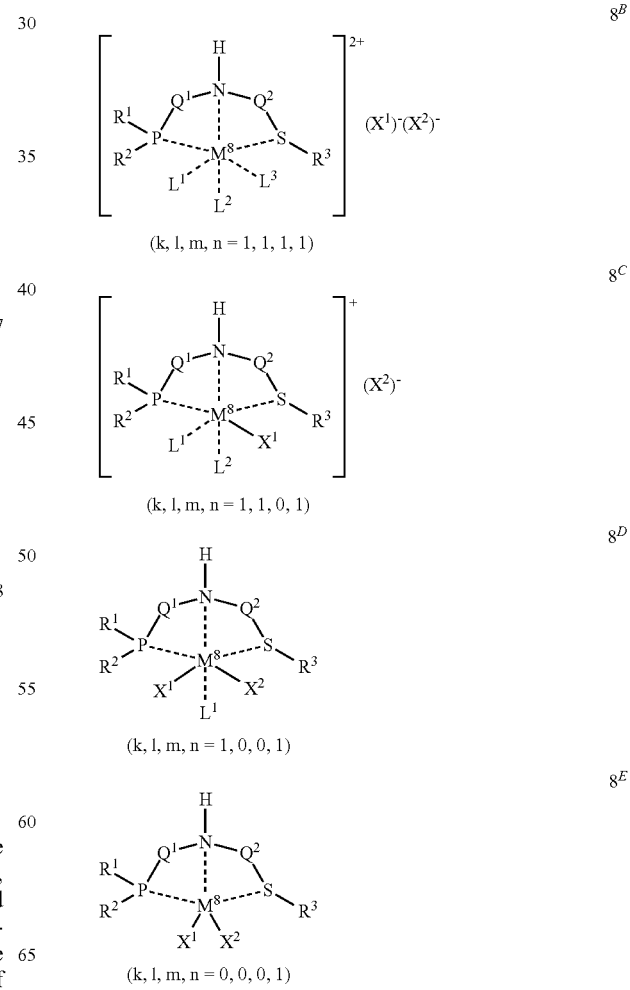

Some of the above-described N-heterocyclic carbenes are compounds unstable in air. Hence, to facilitate the handling, the N-heterocyclic carbenes may be reacted with a Brønsted acid, specifically, for example, hydrochloric acid, hydrobromic acid, hydroiodic acid, tetrafluoroboric acid, or the like to form the corresponding Brønsted acid salts. When any of these Brønsted acid salts is used for producing the metal complex of the present invention, the Brønsted acid salt itself may be used for the reaction. Alternatively, the Brønsted acid salt may be used after the heterocyclic carbene is liberated by a treatment with a base outside the reaction system, or may be used while the N-heterocyclic carbene is being liberated by a treatment with a base in the reaction system.

Next, the relationship between the numeric values represented by k, l, m, and n in the metal complex represented by compositional formula ($8^A$) shown above and the structure of the metal complex is described in detail on the basis of the following structural compositional formulae ($8^B$), ($8^C$), ($8^D$), ($8^E$), and ($8^F$) (a structural compositional formula is defined as a structural formula in which none of the facial/meridional isomerization characteristic of a metal complex having a tridentate ligand, the coordination isomerization characteristic of a metal complex having multiple monodentate ligands, and the "Hemilability" of a tridentate ligand are taken into consideration). Note that, in the following structural compositional formulae ($8^B$) to ($8^F$), H, N, P, S, $R^1$, $R^2$, $R^3$, $Q^1$, and $Q^2$ are the same as those defined in general formula ($1^A$) shown above, $M^8$, $X^1$, $X^2$, $L^1$, $L^2$, and $L^3$ are the same as those defined in compositional formula ($8^A$) shown above, and each dashed line between symbols represents a coordination bond.

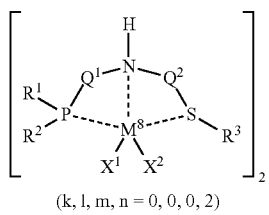

(k, l, m, n = 0, 0, 0, 2)

Combinations of the numeric values represented by k, l, m, and n are described in the form of (k, l, m, n)=((numeric value of k), (numeric value of l), (numeric value of m), and (numeric value of n)). As can be seen from structural compositional formulae ($8^B$) to ($8^F$) shown above, when (k, l, m, n)=(1, 1, 1, 1), compositional formula ($8^A$) represents a dicationic complex, when (k, l, m, n)=(1, 1, 1, 0), compositional formula ($8^A$) represents a cationic complex, and when (k, l, m, n)=(1, 0, 0, 1), compositional formula ($8^A$) represents a neutral complex. Moreover, when (k, l, m, n)=(0, 0, 0, 1), compositional formula ($8^A$) represents a neutral pentacoordinated complex, and when (k, l, m, n)=(0, 0, 0, 2), compositional formula ($8^A$) represents a neutral dinuclear complex.

In a preferred mode, the metal complex represented by compositional formula ($8^A$) may be a metal complex represented by any one of structural compositional formulae ($8^B$) to ($8^F$), in which $Q^1$ in is a 1,2-ethanediyl group, i.e., a metal complex represented by any one of the following structural compositional formulae ($8^G$), ($8^H$), ($8^I$), ($8^J$), and ($8^K$)

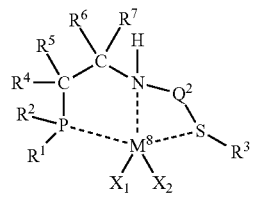

(k, l, m, n = 0, 0, 0, 1)

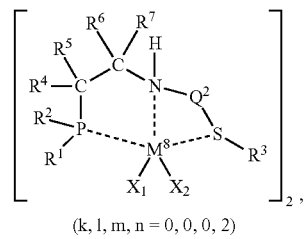

(k, l, m, n = 0, 0, 0, 2)

wherein C, H, N, P, S, $R^1$, $R^3$, $R^4$, $R^5$, $R^6$, $R^7$, and $Q^2$ are the same as those defined in general formula ($1^B$) shown above. $M^8$, $X^1$, $X^2$, $L^1$, $L^2$, and $L^3$ are the same as those defined in compositional formula ($8^A$) shown above, and each dashed line between symbols represents a coordinate bond, or a metal complex represented by any one of structural compositional formulae ($8^B$) to ($8^F$), in which $Q^2$ is a 1,2-ethanediyl group, i.e., a metal complex represented by any one of the following structural compositional formulae ($8^L$), ($8^M$), ($8^N$), ($8^O$), and ($8^P$):

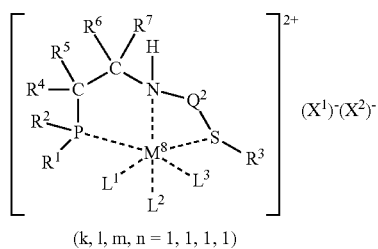

(k, l, m, n = 1, 1, 1, 1)

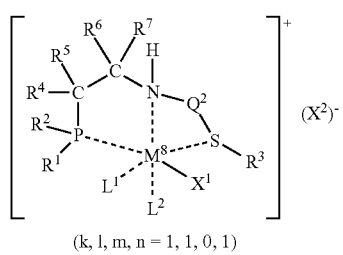

(k, l, m, n = 1, 1, 0, 1)

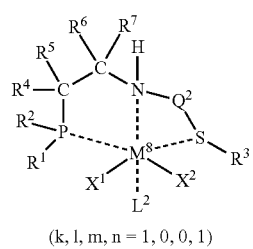

(k, l, m, n = 1, 0, 0, 1)

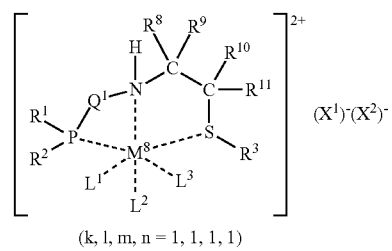

(k, l, m, n = 1, 1, 1, 1)

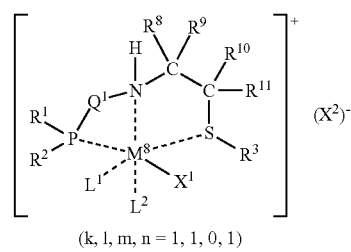

(k, l, m, n = 1, 1, 0, 1)

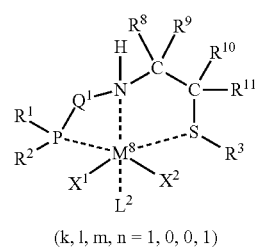

(k, l, m, n = 1, 0, 0, 1)

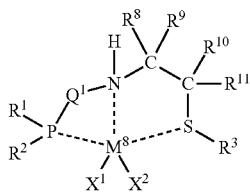

$8^O$ (k, l, m, n = 0, 0, 0, 1)

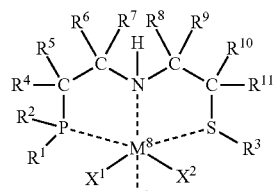

$8^S$ (k, l, m, n = 1, 0, 0, 1)

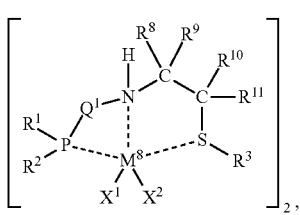

$8^P$ (k, l, m, n = 0, 0, 0, 2)

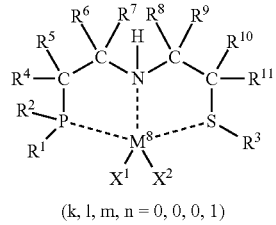

$8^T$ (k, l, m, n = 0, 0, 0, 1)

wherein C, H, N, P, S, $R^1$, $R^3$, $R^8$, $R^9$, $R^{10}$, $R^{11}$, and $Q^1$ are the same as those defined in general formula ($1^C$) shown above; and $M^8$, $X^1$, $X^2$, $L^1$, $L^2$, and $L^3$ are the same as those defined in compositional formula ($8^A$) shown above, and each dashed line between symbols represents a coordinate bond.

In a more preferred mode, the metal complex represented by compositional formula ($8^A$) may be a metal complex represented by any one of structural compositional formula ($8^B$) to ($8^F$) shown above, in which each of $Q^1$ and $Q^2$ is a 1,2-ethanediyl group, i.e., a metal complex represented by any one of the following structural compositional formulae ($8^Q$), ($8^R$), ($8^S$), ($8^T$), and ($8^U$):

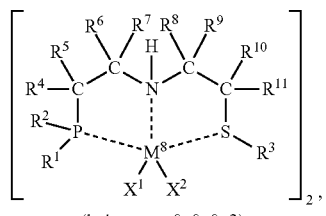

$8^U$ (k, l, m, n = 0, 0, 0, 2)

wherein C, H, N, P, S, $R^1$, $R^3$, $R^4$, $R^5$, $R^6$, $R^7$, $R^8$, $R^9$, $R^{10}$, and $R^{11}$ are the same as those defined in general formula ($1^D$) shown above; and $M^8$, $X^1$, $X^2$, $L^1$, $L^2$, and $L^3$ are the same as those defined in compositional formula ($8^A$) shown above, and each dashed line between symbols represents a coordinate bond. In a particularly preferred mode, the metal complex is represented by any one of structural compositional formulae ($8^R$), ($8^S$), and ($8^U$) shown above. Specific particularly preferred examples of the metal complex represented by compositional formula ($8^A$) include metal complexes of the following structural compositional formulae ($8^S$-1) to ($8^S$-17), ($8^U$-1) to ($8^U$-3), and ($8^R$-1):

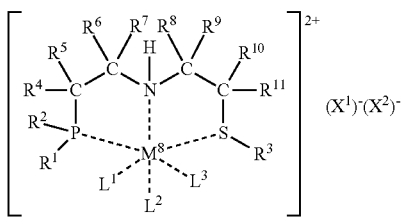

$8^Q$ (k, l, m, n = 1, 1, 1, 1)

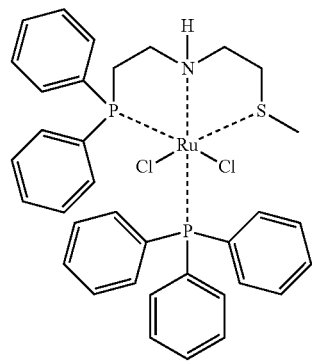

$8^S$-1

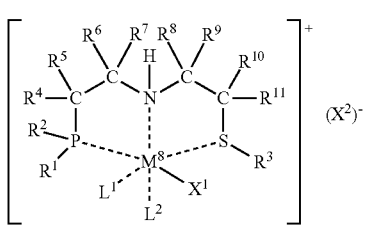

$8^R$ (k, l, m, n = 1, 1, 0, 1)

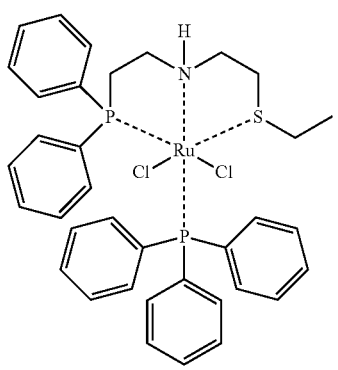
8S-2
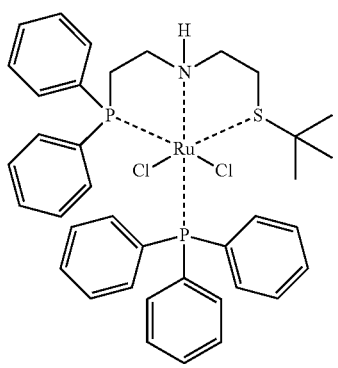
8S-3
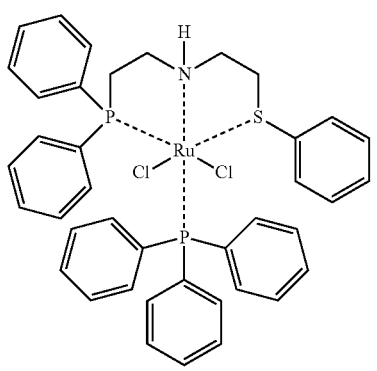
8S-4
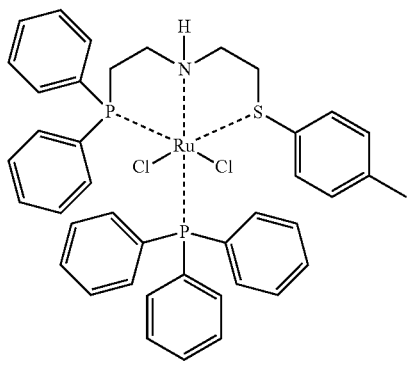
8S-5
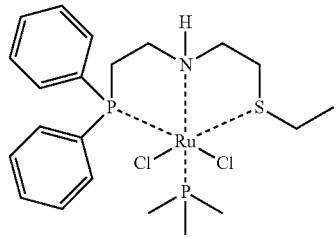
8S-6
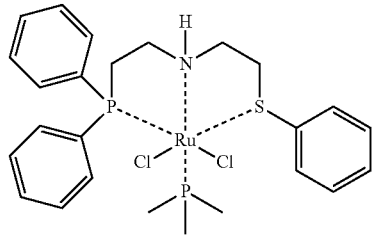
8S-7
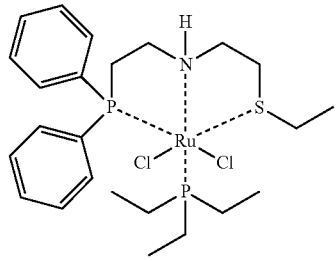
8S-8
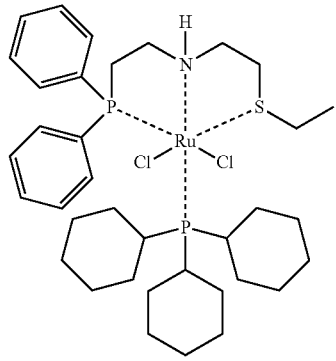
8S-9
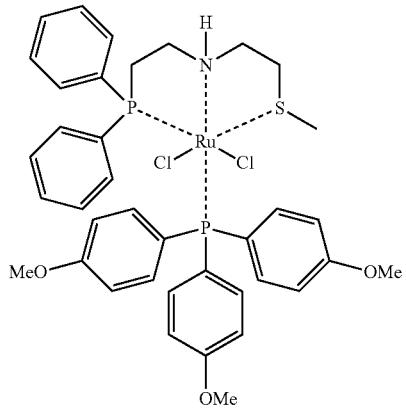
8S-10

-continued
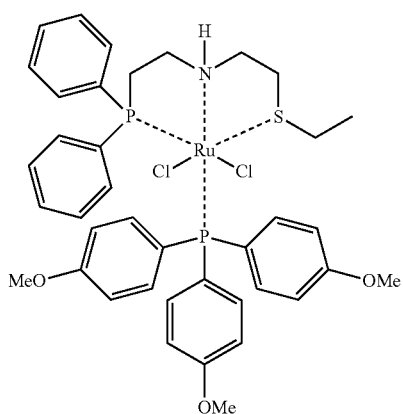
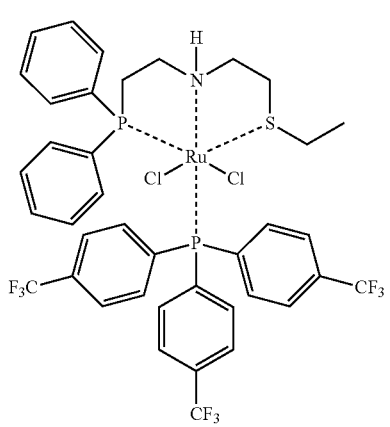
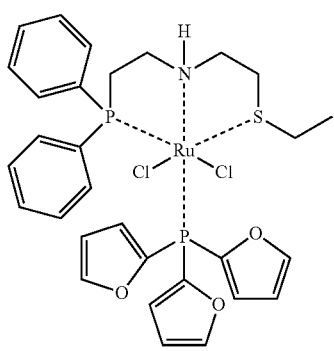
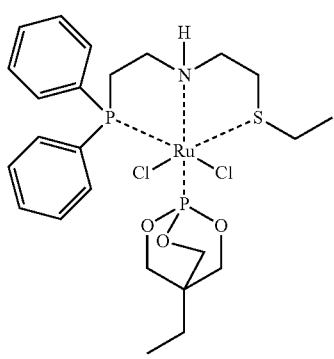
-continued
8<sup>S</sup>-11
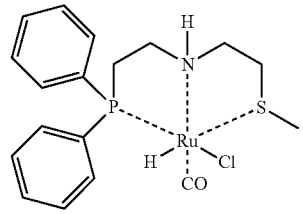
8<sup>S</sup>-16
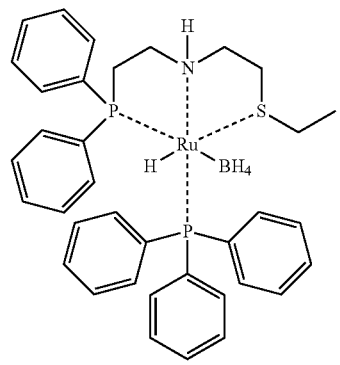
8<sup>S</sup>-17
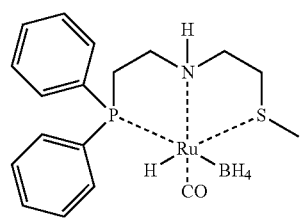
8<sup>U</sup>-1
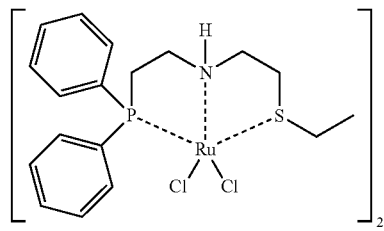
8<sup>U</sup>-2
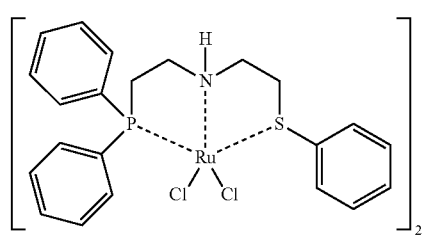
8<sup>U</sup>-3
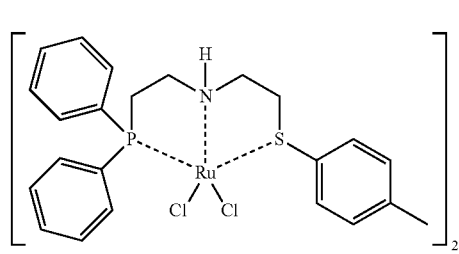

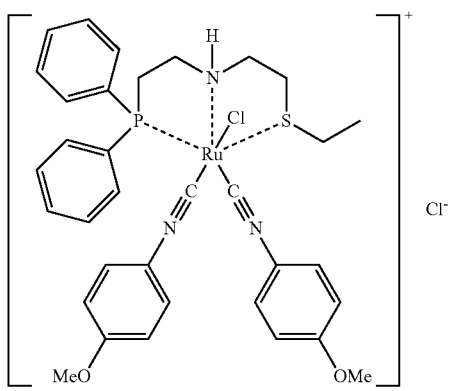

8^R-1

Next, the relationship between the numeric values of k, l, and m in the metal complex represented by compositional formula ($9^A$) and the structure of the metal complex is described based on the following structural compositional formulae ($9^B$), ($9^C$), ($9^D$), and ($9^E$). Note that, in the following structural compositional formulae ($9^B$) to ($9^E$), H, N, P, S, $R^1$, $R^3$, $Q^1$, and $Q^2$ are the same as those defined in general formula ($1^A$) shown above, $M^9$, $X^1$, $X^2$, $X^3$, $L^1$, $L^2$, and $L^3$ are the same as those defined in compositional formula ($9^A$) shown above, and each dashed line between symbols represents a coordinate bond.

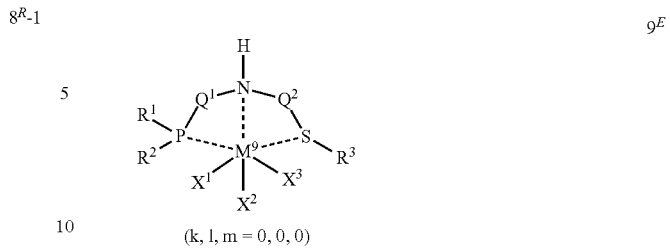

(k, l, m = 0, 0, 0)

Combinations of the numeric values represented by k, l, and m are described in the form of (k, l, m)=((numeric value of k), (numeric value of l), (numeric value of m)). As can be seen from structural compositional formulae ($9^B$) to ($9^E$) shown above, compositional formula ($9^A$) represents a tri-cationic complex, when (k, l, m)=(1, 1, 1), or a dicationic complex, when (k, l, m)=(1, 1, 0). In addition, compositional formula ($9^A$) represents a cationic complex when (k, l, m)=(1, 0, 0), or a neutral complex when (k, l, m)=(0, 0, 0).

In a preferred mode, the metal complex represented by compositional formula ($9^A$) may be a metal complex represented by any one of structural compositional formula ($9^B$) to ($9^E$) shown above, in which $Q^1$ is a 1,2-ethanediyl group, i.e., a metal complex represented by any one of the following structural compositional formulae ($9^F$), ($9^G$), ($9^H$), and ($9^I$):

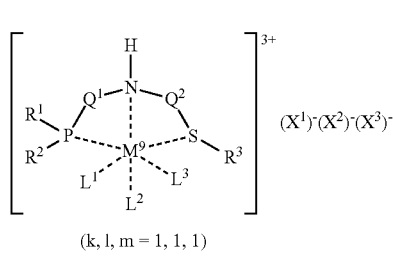

(k, l, m = 1, 1, 1)

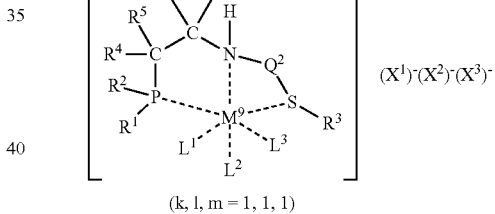

(k, l, m = 1, 1, 1)

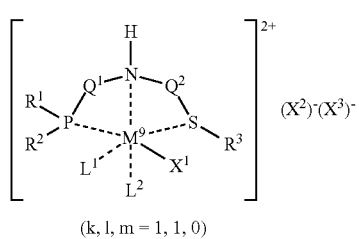

(k, l, m = 1, 1, 0)

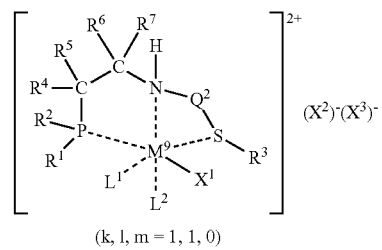

(k, l, m = 1, 1, 0)

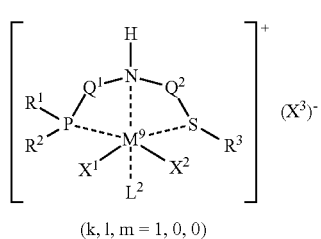

(k, l, m = 1, 0, 0)

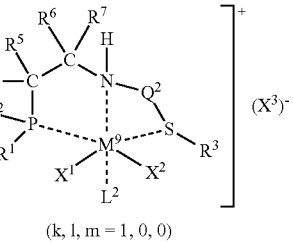

(k, l, m = 1, 0, 0)

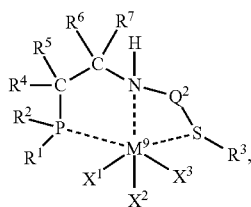

(k, l, m = 0, 0, 0)

wherein C, H, N, P, S, $R^1$, $R^3$, $R^4$, $R^5$, $R^6$, $R^7$, and $Q^2$ are the same as those defined in general formula ($1^B$) shown above; and $M^9$, $X^1$, $X^2$, $X^3$, $L^1$, $L^2$, and $L^3$ are the same as those defined in compositional formula ($9^A$), and each dashed line between symbols represents a coordinate bond, or a metal complex represented by any one of structural compositional formula ($9^B$) to ($9^E$) shown above, in which $Q^2$ is a 1,2-ethanediyl group, i.e., a metal complex represented by anyone of the following structural compositional formulae ($9^J$), ($9^K$), ($9$ L), and ($9^M$):

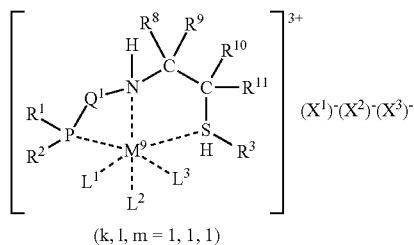

(k, l, m = 1, 1, 1)

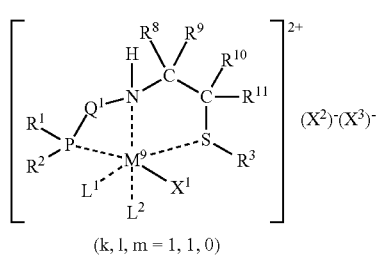

(k, l, m = 1, 1, 0)

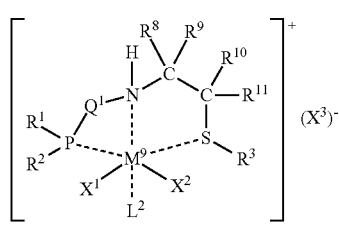

(k, l, m = 1, 0, 0)

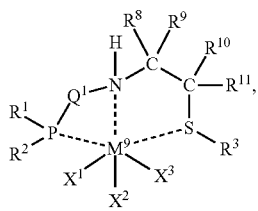

(k, l, m = 0, 0, 0)

wherein C, H, N, P, S, $R^1$, $R^3$, $R^8$, $R^9$, $R^{10}$, $R^{11}$, and $Q^1$ are the same as those defined in general formula ($1^C$) shown above; and $M^9$, $X^1$, $X^2$, $X^3$, $L^1$, $L^2$, and $L^3$ are the same as those defined in compositional formula ($9^A$) shown above, and each dashed line between symbols represents a coordinate bond.

In a more preferred mode, the metal complex represented by compositional formula ($9^A$) may be a metal complex represented by any one of structural compositional formulae ($9^B$) to ($9^E$) shown above, in which each of $Q^1$ and $Q^2$ is a 1,2-ethanediyl group, i.e., a metal complex represented by the following structural compositional formulae ($9^N$), ($9^O$), ($9^P$), and ($9^Q$):

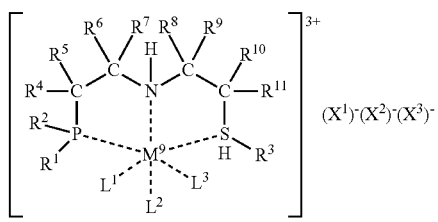

(k, l, m = 1, 1, 1)

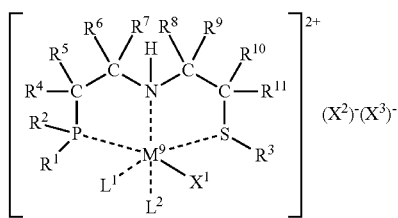

(k, l, m = 1, 1, 0)

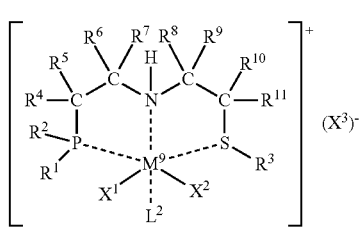

(k, l, m = 1, 0, 0)

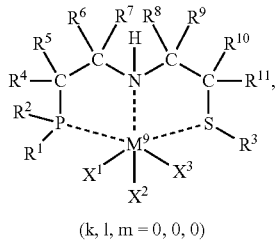

(k, l, m = 0, 0, 0)

wherein each solid line between symbols, C, H, N, P, S, $R^1$, $R^3$, $R^4$, $R^5$, $R^6$, $R^7$, $R^8$, $R^9$, $R^{10}$, and $R^{11}$ are the same as those defined in general formula ($1^D$) shown above; and $M^9$, $X^1$, $X^Z$, $X^3$, $L^1$, $L^2$, and $L^3$ are the same as those defined in compositional formula ($9^A$) shown above, and each dashed line between symbols represents a coordinate bond.

Moreover, the relationship between the numeric value of k in the metal complex represented by compositional formula ($10^A$) shown above and the structure of the metal complex is described based on the following structural compositional formulae ($10^B$) and ($10^C$). Note that, in the following structural compositional formulae ($10^B$) and ($10^C$), H, N, P, S, $R^1$, $R^3$, $Q^1$, and $Q^2$ are the same as those defined in general formula ($1^A$) shown above, $M^{10}$, $X^1$, $X^2$, and $L^1$ are the same as those defined in compositional formula (10) shown above, and each dashed line between symbols represents a coordinate bond.

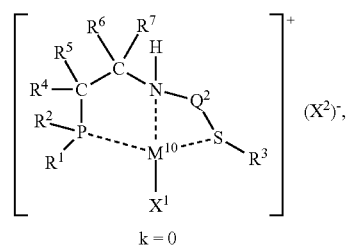

The numeric value represented by k is described in the form of k=(numeric value of k). As can be seen from structural compositional formulae ($10^B$) and ($10^C$), compositional formula ($10^A$) represents a dicationic complex when k=1, and represents a cationic complex when k=0.

In a preferred mode, the metal complex represented by compositional formula ($10^A$) may be a metal complex represented by structural compositional formula ($10^B$) or ($10^C$) shown above, in which $Q^1$ is a 1,2-ethanediyl group, i.e., a metal complex represented by the following structural compositional formula ($10^D$) or ($10^E$):

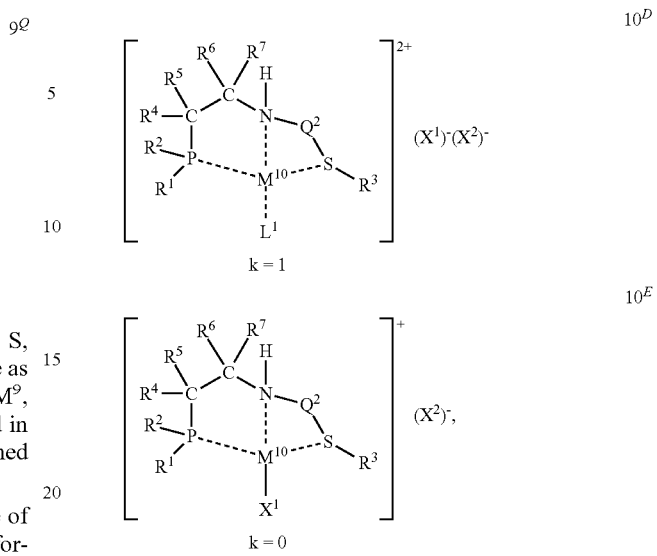

wherein C, H, N, P, S, $R^1$, $R^3$, $R^4$, $R^5$, $R^6$, $R^7$, and $Q^2$ are the same as those defined in general formula ($1^B$) shown above; and $M^{10}$, $X^1$, $X^2$, and $L^1$ are the same as those defined in compositional formula ($10^A$) shown above, and each dashed line between symbols represents a coordinate bond, or a metal complex represented by structural compositional formulae ($10^B$) or ($10^C$) shown above, in which $Q^2$ is a 1,2-ethanediyl group, i.e., a metal complex represented by the following structural compositional formula ($10^F$) or ($10^G$):

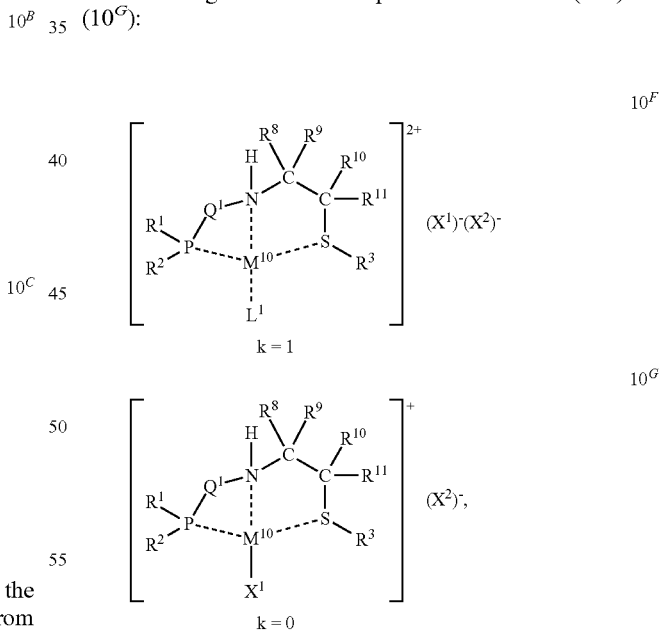

wherein C, H, N, P, S, R, $R^3$, $R^8$, $R^9$, $R^{10}$, $R^{11}$, and $Q^1$ are the same as those defined in general formula ($1^C$) shown above; and $M^{10}$, $X^1$, $X^2$, and $L^1$ are the same as those defined in compositional formula ($10^A$) shown above, and each dashed line between symbols represents a coordinate bond.

In a more preferred mode, the metal complex represented by compositional formula ($10^A$) may be a metal complex represented by structural compositional formula ($10^B$) or ($10^C$), in which each of $Q^1$ and $Q^2$ is a 1,2-ethanediyl group, i.e., a metal complex represented by the following structural compositional formula ($10^H$) or ($10^I$):

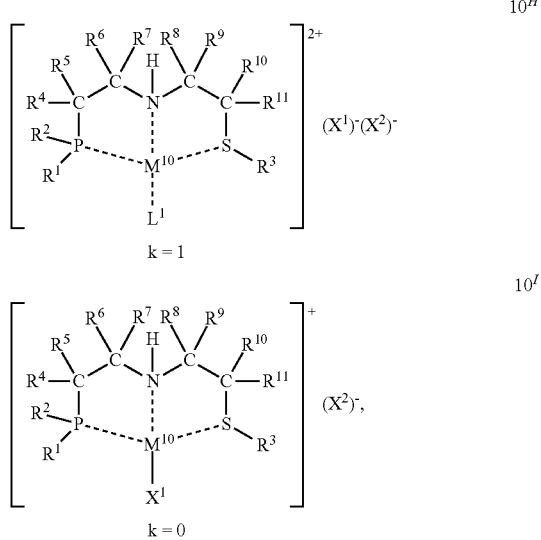

wherein C, H, N, P, S, $R^1$, $R^3$, $R^4$, $R^5$, $R^6$, $R^7$, $R^8$, $R^9$, $R^{10}$, and $R^{11}$ are the same as those defined in general formula ($1^D$) shown above; and $M^{10}$, $X^1$, $X^2$, and $L^1$ are the same as those defined in compositional formula ($10^4$) shown above, and each dashed line between symbols represents a coordinate bond.

Note that, because of the coordination effect of the metal species, the hydrogen atom on the imino group of the metal complex of the present invention has a higher acidity than the hydrogen atom on the imino group of the compound of the present invention. Hence, upon treatment with a base, the metal complex of the present invention is deprotonated, so that the coordinate bond between the metal atom and the nitrogen atom changes to a covalent bond in some cases. A specific description is made by taking, as an example, the formation of a metal complex represented by the following structural compositional formula ($8^{D'}$), wherein each dashed line between symbols, N, P, S, $R^1$, $R^2$, $R^3$, $Q^1$, $Q^2$, $M^8$, $X^1$, and $L^1$ are the same as those defined in structural compositional formula ($8^D$) shown above, by the deprotonation of the metal complex ($8^D$) of the present invention (Eq. 6). The deprotonated metal complex of the present invention is important also as an active intermediate in catalytic organic synthesis reactions.

Eq. 6

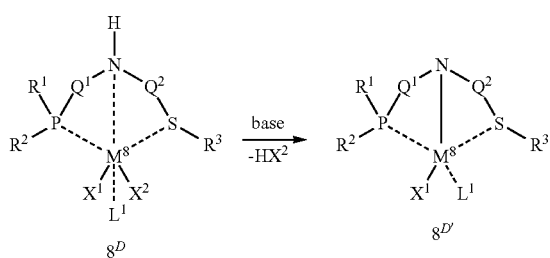

The compound of the present invention is useful as a tridentate ligand for various catalytic organic synthesis reactions, and the metal complex of the present invention is useful as a catalyst for various organic synthesis reactions. The organic synthesis reactions are not particularly limited, and specifically include oxidation reactions, reduction reactions, hydrogenation reactions, dehydrogenation reactions, hydrogen transfer reactions, addition reactions, conjugate addition reactions, cyclization reactions, functional-group conversion reactions, isomerization reactions, rearrangement reactions, polymerization reactions, bond formation reactions, bond cleavage reactions, and the like, of which hydrogenation reactions are preferable, and hydrogenation reactions of esters and the like are more preferable.

When the compound of the present invention is used as a ligand for a catalytic organic synthesis reaction, adding the compound of the present invention to the reaction system is not particularly limited, and each of the compound of the present invention and a metal compound may be added separately to the reaction system. Alternatively, a mixture of the compound of the present invention and a metal compound (and a solvent) may be added to the reaction system, or a solution of the metal complex of the present invention obtained by reacting the compound of the present invention with a metal compound (and, if necessary, the monoanionic monodentate ligand source, the neutral monodentate ligand, and a neutral monodentate ligand equivalent such as a Brønsted acid salt of an N-heterocyclic carbene) in a solvent may be added to the reaction system. In these methods for addition, the monoanionic monodentate ligand source, the neutral monodentate ligand, and the neutral monodentate ligand equivalent may be additionally added to adjust the catalytic activity and the reaction selectivity. In addition, one of the compounds of the present invention may be used alone, or two or more thereof may be used, as appropriate, in combination.

When the metal complex of the present invention is used as a catalyst for an organic synthesis reaction, the reaction for adding the metal complex of the present invention to the reaction system is not particularly limited, and the metal complex of the present invention may be added alone to the reaction system. Alternatively, the metal complex of the present invention may be dissolved or suspended in a solvent, and then added to the reaction system. In these methods for addition, the compound of the present invention, the monoanionic monodentate ligand source, the neutral monodentate ligand, and the neutral monodentate ligand equivalent may be additionally added to adjust the catalytic activity and the reaction selectivity. In addition, one of these metal complexes of the present invention may be used alone, or two or more thereof may be used, as appropriate, in combination.

EXAMPLES

Hereinafter, the compound of the present invention, the metal complex of the present invention, and catalytic reactions using the metal complex of the present invention are described in detail based on Examples and Comparative Examples; however, the present invention is not limited to Examples and Comparative Examples at all. In Examples and Comparative Examples, the following apparatuses and conditions were employed for measuring physical properties.

1) Proton nuclear magnetic resonance spectroscopy ($^1$H NMR): Varian Mercury plus Model 300 spectrometer (resonance frequency: 300 MHz, manufactured by Varian, Inc.)

or Model 400MR DD2 spectrometer (resonance frequency: 400 MHz, manufactured by Agilent Technologies, Inc.)
Internal standard substances: tetramethylsilane (0 ppm (singlet peak)) or residual non-deuterated solvent (methanol: 3.31 ppm (quintet peak), dichloromethane: 5.32 ppm (triplet peak), or chloroform: 7.26 ppm (singlet peak))
2) Carbon 13 nuclear magnetic resonance spectroscopy ($^{13}C$ NMR): Varian Mercury plus Model 300 spectrometer (resonance frequency: 75 MHz, manufactured by Varian, Inc.) or Model 400MR DD2 spectrometer (resonance frequency: 100 MHz, manufactured by Agilent Technologies, Inc.)
Internal standard substance: chloroform (77 ppm (triplet peak))
3) Phosphorus 31 nuclear magnetic resonance spectroscopy ($^{31}P$ NMR): Varian Mercury plus Model 300 spectrometer (resonance frequency: 121 MHz, manufactured by Varian, Inc.) or Model 400MR DD2 spectrometer (resonance frequency: 161 MHz, manufactured by Agilent Technologies, Inc.)
External standard substance: phosphoric acid (0 ppm (singlet peak)) in heavy water
4) Fluorine 19 nuclear magnetic resonance spectroscopy ($^{19}F$ NMR): Model 400MR DD2 spectrometer (resonance frequency: 376 MHz, manufactured by Agilent Technologies, Inc.)
External standard substance: α,α,α-trifluoro-p-xylene (−64 ppm (singlet peak))
5) Gas chromatography (GC): Model GC-4000 apparatus (manufactured by GL Sciences Inc.)
Column: InertCap PureWax (manufactured by GL Sciences Inc.), sample inlet: 200° C., sample detector: 250° C., initial temperature: 50° C., temperature ramp rate 1: 5° C./minute, target temperature 1: 150° C., holding time at target temperature 1: 0 minutes, temperature ramp rate 2: 10° C./minute, target temperature 2: 250° C., holding time at target temperature 2: 5 minutes.
6) High-resolution mass spectrometry (HRMS): LCMS-IT-TOF-type spectrometer (manufactured by Shimadzu Corporation)
Examples 1 to 10 relate to production of compounds of the present invention, Examples 11 to 31 relate to production of metal complexes of the present invention, and Examples 32 and 33 and Comparative Examples 1 to 4 relate to organic synthesis reactions using the metal complex of the present invention as a catalyst. Note that, unless otherwise noted, the substrates, the solvents, and the like were introduced under a nitrogen stream, the reactions were carried out in a nitrogen atmosphere, and post treatments on the reaction liquids and purification of the crude products were carried out in air.

(Example 1) Synthesis of 2-Diphenylphosphino-N-[2-(methylthio)ethyl]ethylamine (Structural Formula ($1^D$-1)), Route 1 (Eq. 7)

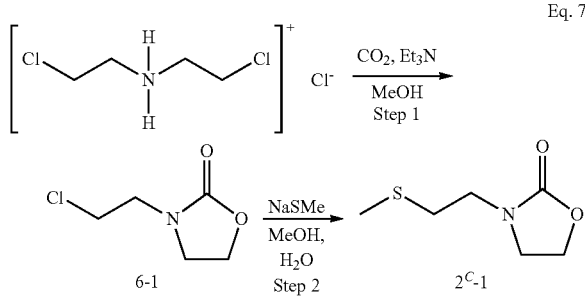

Eq. 7

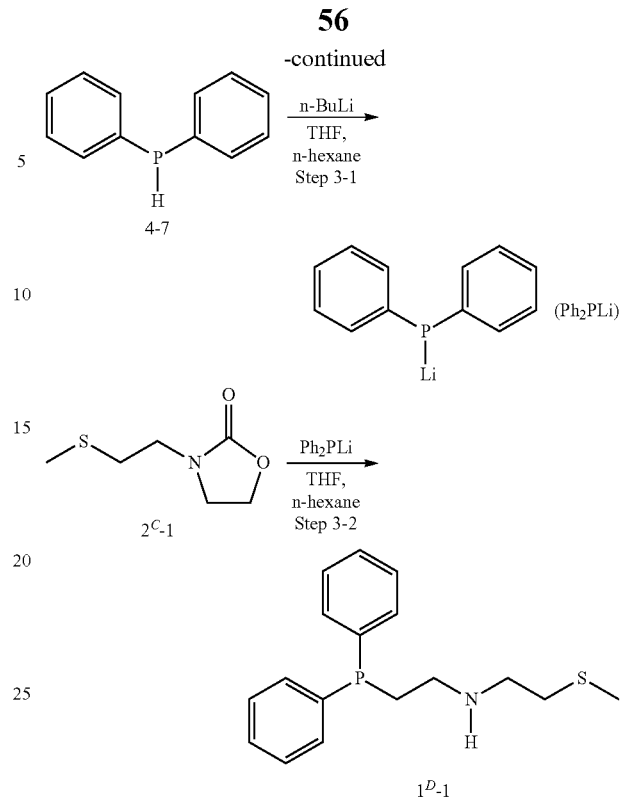

Step 1: Synthesis of 3-(2-Chloroethyl)-2-oxazolidinone (Structural Formula (6-1))

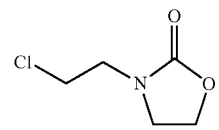

6-1

(Setup and Reaction)
This step was carried out in air. To a 2 L four-necked round-bottom flask, a magnetic stirrer bar and a thermometer were attached, and N,N-bis(chloroethyl)amine hydrochloride (200.0 g, 1.12 mol, 1.0 equivalents), methanol (MeOH) (600 mL), and triethylamine ($Et_3N$) (328.0 mL, 2.35 mol, 2.1 equivalents) were sequentially introduced. Carbon dioxide ($CO_2$) gas generated from dry ice was passed through the obtained solution at room temperature for 1 hour.
(Post Treatment, Isolation, and Purification)
After the reaction liquid was concentrated under reduced pressure, toluene (1.0 L) was added, and the obtained white suspension was filtered by suction. Then, the residue was washed with toluene. The filtrates were collectively concentrated under reduced pressure to obtain 165.7 g of title compound (6-1) as a light yellow liquid. Isolated yield: 98.9%. Note that this compound could be decolorized by distillation purification (boiling point: 135° C. (3 mmHg)); however, this compound was used in the subsequent step without any further purification, because the compound was almost pure based on the results of NMR analyses.
$^1H$ NMR (300 MHz, deuterated chloroform ($CDCl_3$)): δ=4.38 (ddd, J=0.9, 6.3, 7.8 Hz, 2H), 3.79-3.67 (m, 4H), 3.66-3.59 (m, 2H).

Step 2: Synthesis of 3-[2-(Methylthio)ethyl]-2-oxazolidinone (Structural Formula ($2^C$-1))

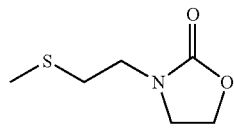

(Setup and Reaction)

This step was carried out in air. To a 1 L four-necked round-bottom flask, a magnetic stirrer bar, a condenser, a dropping funnel, and a thermometer were attached. Then, 3-(2-chloroethyl)-2-oxazolidinone (6-1) (48.7 g, 325.6 mmol, 1.0 equivalents) obtained in Step 1 and MeOH (200 mL) were introduced sequentially, and the obtained solution was heated to 55° C. Subsequently, a 21.3% by weight aqueous solution of sodium salt of methanethiol (5-1) (NaSMe) (128.6 g, 390.7 mmol, 1.2 equivalents) was placed in a dropping funnel, and added dropwise to the solution over 15 minutes. Then, the reaction liquid was stirred at 60° C. for 1 hour.

(Post Treatment, Isolation, and Purification)

After 190 mL of MeOH was recovered from the reaction liquid under reduced pressure, ethyl acetate (500 mL) was added, and the organic layer was separated. After extraction from the aqueous layer with ethyl acetate once, the organic layers were collectively concentrated under reduced pressure. The obtained residue was purified by distillation purification (boiling point: 137° C. (0.4 mmHg)) to obtain 43.9 g of title compound ($2^C$-1) as a colorless liquid. Isolated yield: 83.6%.

$^1$H NMR (400 MHz, CDCl$_3$): δ=4.38-4.32 (m, 2H), 3.67-3.62 (m, 2H), 3.49 (t, J=6.8 Hz, 2H), 2.70 (t, J=6.8 Hz, 2H), 2.15 (s, 3H).

$^{13}$C NMR (100 MHz, CDCl$_3$): δ=158.38, 61.77, 44.80, 42.87, 31.77, 15.18.

Step 3: Synthesis of 2-Diphenylphosphino-N-[2-(methylthio)ethyl]ethylamine (Structural Formula ($1^D$-1))

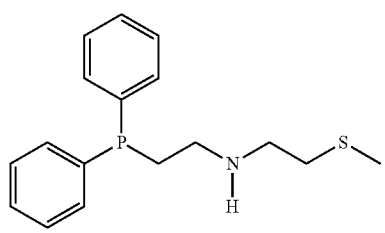

(Setup and Reaction)

To a 200 mL four-necked round-bottom flask, a magnetic stirrer bar, a dropping funnel, a thermometer, and a three-way stopcock were attached, and the inside was purged with nitrogen. Then, diphenylphosphine (4-7) (purity: 98.5%, 10.0 g, 52.9 mmol, 1.1 equivalents) and anhydrous tetrahydrofuran (THF) (50 mL) were introduced sequentially. The obtained solution was cooled to 5° C. in an ice-water bath. A n-hexane solution of n-butyllithium (n-BuLi) (concentration: 1.60 mol/L, 33.1 mL, 52.9 mmol, 1.1 equivalents) was placed in a dropping funnel, and added dropwise to the solution at such a rate that the inside temperature was kept at 10° C. or below over 20 minutes. Then, the ice-water bath was removed, followed by stirring at room temperature for 20 minutes. Thus, a solution of lithium diphenylphosphide (Ph$_2$PLi) in THF/n-hexane (52.9 mmol, 1.1 equivalents) was prepared as a reddish orange liquid. Subsequently, 3-[2-(methylthio)ethyl]-2-oxazolidinone ($2^C$-1) (7.8 g, 48.1 mmol, 1.0 equivalents) obtained in Step 2 and anhydrous THF (10 mL) were sequentially introduced into a dropping funnel, and added dropwise to the Ph$_2$PLi solution at such a rate that the inside temperature was kept at 30° C. or below over 30 minutes.

(Post Treatment, Isolation, and Purification)

The reaction liquid was concentrated under reduced pressure, and water (100 mL) and ethyl acetate (200 mL) were added, followed by stirring. Then, the mixture was allowed to stand, and the aqueous layer was separated. The organic layer was concentrated under reduced pressure, and the obtained residue was purified by silica gel column chromatography (eluent: toluene/ethyl acetate/triethylamine=2/1/0.03 to 1/2/0.03) to obtain 12.5 g of title compound ($1^D$-1) as a light yellow viscous liquid. Isolated yield: 77.9%.

$^1$H NMR (400 MHz, CDCl$_3$): δ=7.46-7.39 (m, 4H), 7.36-7.30 (m, 6H), 2.82-2.72 (m, 4H), 2.61 (t, J=6.4 Hz, 2H), 2.31-2.25 (m, 2H), 2.07 (s, 3H), 1.53* (br s, 1H). (* note that the peak attributable to water was included)

$^{31}$P NMR (161 MHz, CDCl$_3$): δ=−20.7.

(Example 2) Synthesis of 2-Diphenylphosphino-N-[2-(methylthio)ethyl]ethylamine (Structural Formula ($1^D$-1)), Route 2 (Eq. 8)

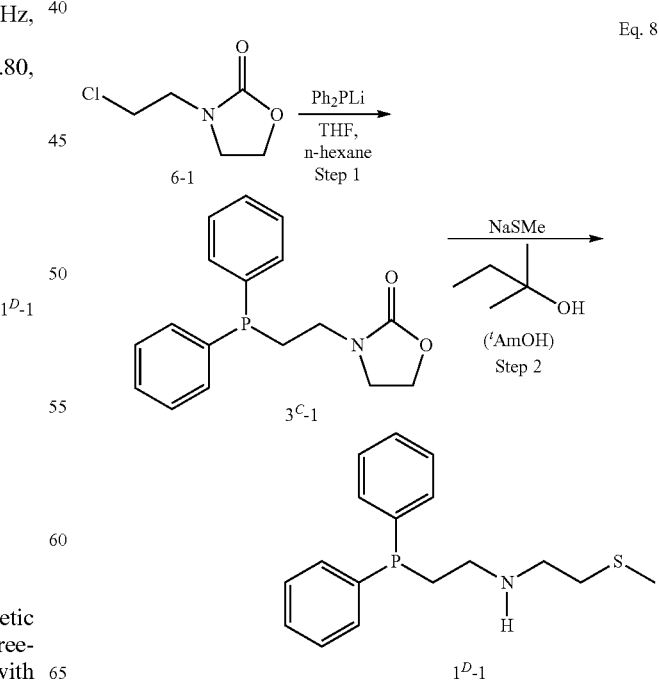

Eq. 8

Step 1: Synthesis of 3-[2-(Diphenylphosphino)ethyl]-2-oxazolidinone (Structural Formula ($3^C$-1))

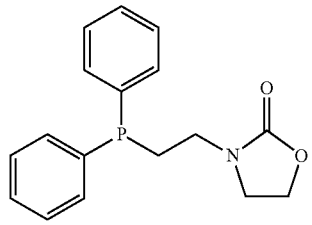

$3^C$-1

(Setup and Reaction)

To a 500 mL four-necked round-bottom flask, a magnetic stirrer bar, a dropping funnel, a thermometer, and a three-way stopcock were attached, and the inside was purged with nitrogen. Then, 3-(2-chloroethyl)-2-oxazolidinone (6-1) (16.1 g, 107.4 mmol, 1.0 equivalents) obtained in Step 1 of Example 1 and anhydrous THF (80 mL) were introduced, and the obtained solution was cooled to −30° C. by using a dry ice/acetone bath. Subsequently, a Ph$_2$PLi THF/n-hexane solution (107.4 mmol, 1.0 equivalents) prepared in the same manner as in Step 3 of Example 1 was placed in a dropping funnel, and added dropwise to the solution at such a rate that the inside temperature was kept at −20° C. or below over 2.5 hours. Then, the temperature of the obtained reaction liquid was raised to room temperature.

(Post Treatment, Isolation, and Purification)

After the reaction liquid was concentrated under reduced pressure, toluene (300 mL) and water (100 mL) were added to the obtained residue, followed by stirring. Then, the mixture was allowed to stand, and the aqueous layer was separated. The organic layer was washed with water (50 mL) three times, and then concentrated under reduced pressure. The obtained residue was recrystallized from 2-methyl-2-butanol ($^t$AmOH) to obtain 18.7 g of title compound ($3^C$-1) as a white powder. Isolated yield: 58.2%.

$^1$H NMR (300 MHz, CDCl$_3$): δ=7.49-7.31 (m, 10H), 4.21-4.13 (m, 2H), 3.54-3.37 (m, 4H), 2.37-2.31 (m, 2H).
$^{31}$P NMR (121 MHz, CDCl$_3$): δ=−21.3.

Step 2: Synthesis of 2-Diphenylphosphino-N-[2-(methylthio)ethyl]ethylamine ($1^D$-1)

(Setup and Reaction)

To a 100 mL four-necked round-bottom flask, a magnetic stirrer bar, a condenser, a thermometer, and a three-way stopcock were attached, and the inside was purged with nitrogen. Then, 3-[2-(diphenylphosphino)ethyl]-2-oxazolidinone ($3^C$-1) (6.0 g, 20.0 mmol) obtained in Step 1, $^t$AmOH (40 mL), and NaSMe (purity: 95.0%, 1.77 g, 24.0 mmol, 1.2 equivalents) were introduced sequentially, and the obtained suspension was stirred for 1 hour under reflux.

(Post Treatment, Isolation, and Purification)

The reaction liquid was concentrated under reduced pressure, and the obtained residue was directly filtered and purified by silica gel column chromatography (eluent: toluene/ethyl acetate/triethylamine=2/1/0.03 to 1/2/0.03) to obtain 4.9 g of title compound ($1^D$-1) as a light yellow viscous liquid. Isolated yield: 80.8%. The NMR analysis results of this compound were completely the same as those obtained in Step 3 of Example 1.

(Example 3) Synthesis of 2-Diphenylphosphino-N-[2-(ethylthio)ethyl]ethylamine (Structural Formula ($1^D$-2)), Route 1 (Eq. 9)

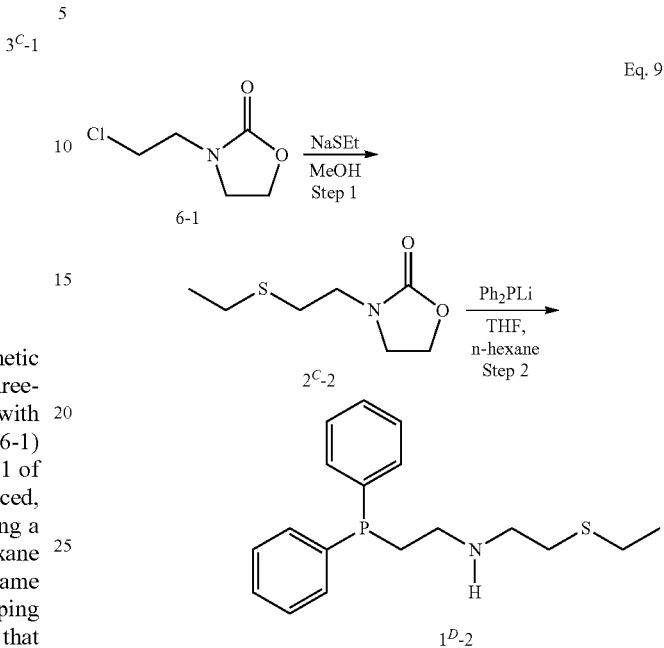

Eq. 9

Step 1: Synthesis of 3-[2-(Ethylthio)ethyl]-2-oxazolidinone (Structural Formula ($2^C$-2))

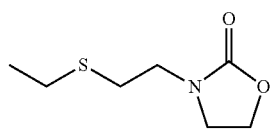

$2^C$-2

(Setup and Reaction)

This step was carried out in air. To a 200 mL four-necked round-bottom flask, a magnetic stirrer bar, a condenser, and a thermometer were attached. Then, 3-(2-chloroethyl)-2-oxazolidinone (6-1) (16.3 g, 109.1 mmol, 1.0 equivalents) obtained in Step 1 of Example 1, MeOH (55 mL), and sodium salt of ethanethiol (5-2) (NaSEt) (purity: 96.4%, 10.0 g, 114.6 mmol, 1.05 equivalents) were introduced sequentially, and the obtained suspension was stirred under reflux for 1 hour.

(Post Treatment, Isolation, and Purification)

The reaction liquid was concentrated under reduced pressure, and the obtained residue was directly filtered and purified by silica gel column chromatography (eluent: toluene/ethyl acetate=1/1 to 1/4) to obtain 17.9 g of title compound ($2^C$-2) as a light yellow liquid. Isolated yield: 93.6%.

$^1$H NMR (300 MHz, CDCl$_3$): δ=4.38-4.30 (m, 2H), 3.69-3.61 (m, 2H), 3.47 (t, J=6.9 HZ, 2H), 2.73 (t, J=6.9 Hz, 2H), 2.59 (q, J=7.2 Hz, 2H), 1.27 (t, J=7.2 Hz, 3H).

Step 2: Synthesis of 2-Diphenylphosphino-N-[2-(ethylthio)ethyl]ethylamine (Structural Formula (1$^D$-2))

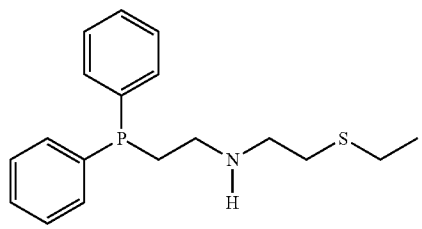

(Setup and Reaction)

By using a 200 mL four-necked round-bottom flask, a magnetic stirrer bar, a dropping funnel, a thermometer, and a three-way stopcock, a Ph$_2$PLi THF/n-hexane solution (52.9 mmol, 1.1 equivalents) was prepared in the same manner as in Step 3 of Example 1. Subsequently, 3-[2-(ethylthio)ethyl]-2-oxazolidinone (2$^C$-2) (8.4 g, 48.1 mmol, 1.0 equivalents) obtained in Step 1 and anhydrous THF (10 mL) were sequentially introduced into a dropping funnel, and added dropwise to the Ph$_2$PLi solution at such a rate that the inside temperature was kept at 30° C. or below over 30 minutes.

(Post Treatment, Isolation, and Purification)

The reaction liquid was concentrated under reduced pressure, and water (100 mL) and ethyl acetate (200 mL) were added, followed by stirring. Then, the mixture was allowed to stand, followed by liquid-liquid separation. The organic layer was concentrated under reduced pressure, and the obtained residue was purified by silica gel column chromatography (eluent: toluene/ethyl acetate/triethylamine=2/1/0.03 to 1/2/0.03) to obtain 13.8 g of title compound (1$^D$-2) as a light yellow viscous liquid. Isolated yield: 90.4%.

$^1$H NMR (300 MHz, CDCl$_3$): δ=7.47-7.29 (m, 10H), 2.82-2.71 (m, 4H), 2.63 (t, J=6.3 Hz, 2H), 2.51 (q, J=7.5 Hz, 2H), 2.28 (dd, J=7.5, 8.1 Hz, 2H), 1.64* (br s, 1H), 1.24 (t, J=7.5 Hz, 3H). (* note that the peak attributable to water was included)

$^{31}$P NMR (121 MHz, CDCl$_3$): δ=−20.6.

(Example 4) Synthesis of 2-Diphenylphosphino-N-[2-(ethylthio)ethyl]ethylamine (Structural Formula (1$^D$-2)), Route 2 (Eq. 10)

Eq. 10

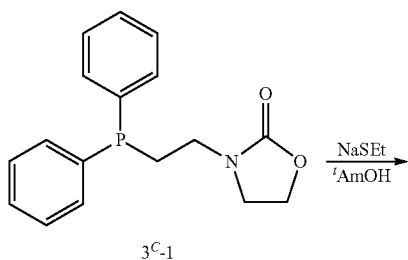

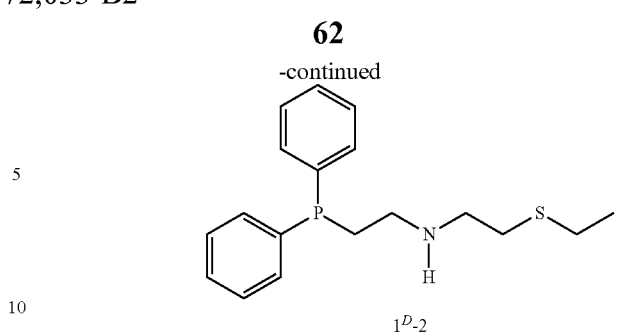

(Setup and Reaction)

To a 100 mL four-necked round-bottom flask, a magnetic stirrer bar, a condenser, a thermometer, and a three-way stopcock were attached, and the inside was purged with nitrogen. Then, 3-[2-(diphenylphosphino)ethyl]-2-oxazolidinone (3$^C$-1) (5.0 g, 16.7 mmol, 1.0 equivalents) obtained in Step 1 of Example 2, $^t$AmOH (33 mL), and NaSEt (purity: 96.4%, 1.75 g, 20.0 mmol, 1.2 equivalents) were introduced sequentially, and the obtained suspension was stirred under reflux for 1 hour.

(Post Treatment, Isolation, and Purification)

The reaction liquid was cooled to room temperature, and water (20 mL) was added, followed by stirring. Then, the mixture was allowed to stand, and the aqueous layer was separated. The organic layer was concentrated under reduced pressure, and the obtained residue was purified by silica gel column chromatography (eluent: toluene/ethyl acetate/triethylamine=2/1/0.03 to 1/2/0.03) to obtain 4.4 g of title compound (1$^D$-2) as a light yellow viscous liquid. Isolated yield: 83.0%. The NMR analysis results of this compound were completely the same as those obtained in Step 2 of Example 3.

As can be seen from Examples 1 to 4, the compound of the present invention can be easily produced from each of the compound represented by general formula (2) and the compound represented by general formula (3).

(Example 5) Synthesis of 2-Diphenylphosphino-N-[2-(ethylthio)ethyl]ethylammonium chloride (Structural Formula (1$^D$-2 Hydrochloride)) (Eq. 11)

Eq. 11

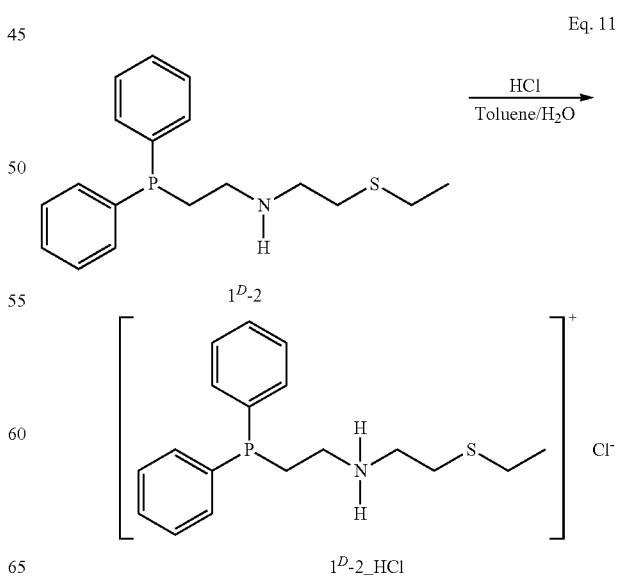

(Setup and Reaction)

This step was carried out in air. To a 100 mL round-bottom flask, a magnetic stirrer bar was attached, and 2-diphenylphosphino-N-[2-(ethylthio)ethyl]ethylamine ($1^D$-2) (3.17 g, 10.0 mmol, 1.0 equivalents) obtained in Example 3/Example 4 and toluene (40 mL) were sequentially introduced.

To the obtained solution, 4 N aqueous hydrochloric acid (HCl) solution (5.0 mL, 20.0 mmol, 2.0 equivalents) was added dropwise by using a pipette, and the obtained white suspension was stirred at room temperature for 10 minutes.

(Post Treatment, Isolation, and Purification)

After the reaction, the obtained suspension was filtered by suction, and then the crystals obtained by filtration were washed with toluene, and dried by heating under reduced pressure. Thus, 3.40 g of title compound ($1^D$-2 hydrochloride) was obtained as a white powder. Isolated yield: 96.12.

$^1$H NMR (400 MHz, deuterated methanol (CD$_3$OD)): δ=7.50-7.43 (m, 4H), 7.42-7.36 (m, 6H), 4.85 (s, 2H), 3.20 (t, J=6.8 Hz, 2H), 3.14-3.06 (m, 2H), 2.81 (t, J=7.2 Hz, 2H), 2.58 (d, J=7.2 Hz, 2H), 2.51-2.45 (m, 2H), 1.25 (t, J=7.2 Hz, 3H).

$^{31}$P NMR (161 MHz, CD$_3$OD): δ=−20.9.

As can be seen from Example 5, it is also possible to derive a crystalline salt, which is easy to handle, from the compound of the present invention by a treatment with a Bronsted acid.

(Example 6) Synthesis of 2-Diphenylphosphino-N-[2-(tert-butylthio) ethyl]ethylamine (Structural Formula ($1^D$-3)) (Eq. 12)

Eq. 12

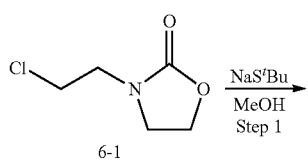

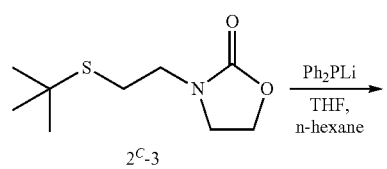

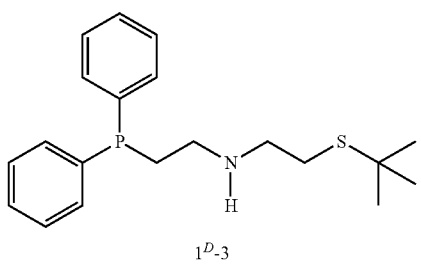

Step 1: Synthesis of 3-[2-(tert-Butylthio)ethyl]-2-oxazolidinone (Structural Formula ($2^C$-3))

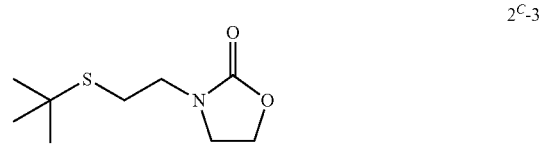

(Setup and Reaction)

This reaction was carried out in air. To a 200 mL four-necked round-bottom flask, a magnetic stirrer bar, a condenser, and a thermometer were attached. Then, 3-(2-chloroethyl)-2-oxazolidinone (6-1) (12.5 g, 83.8 mmol, 1.0 equivalents) obtained in Step 1 of Example 1, MeOH (80 mL), and sodium salt of 2-methyl-2-propanethiol (5-8) (NaS$^t$Bu) (purity: 98.7%, 10.0 g, 88.0 mmol, 1.05 equivalents) were introduced sequentially, and the obtained suspension was stirred under reflux for 3 hours.

(Post Treatment, Isolation, and Purification)

The reaction liquid was concentrated under reduced pressure, and the obtained residue was directly filtered and purified by silica gel column chromatography (eluent: toluene/ethyl acetate=2/1 to 1/2) to obtain 15.6 g of title compound ($2^C$-3) as a colorless liquid. Isolated yield: 91.6%.

$^1$H NMR (400 MHz, CDCl$_3$): δ=4.36-4.28 (m, 2H), 3.68-3.62 (m, 2H), 3.44 (t, J=6.8 Hz, 2H), 2.72 (t, J=6.8 Hz, 2H), 1.31 (s, 9H).

$^{13}$C NMR (100 MHz, CDCl$_3$): δ=158.26, 61.76, 45.31, 44.58, 42.50, 30.91, 26.58.

Step 2: Synthesis of 2-Diphenylphosphino-N-[2-(tert-butylthio)ethyl]ethylamine (Structural Formula ($1^D$-3))

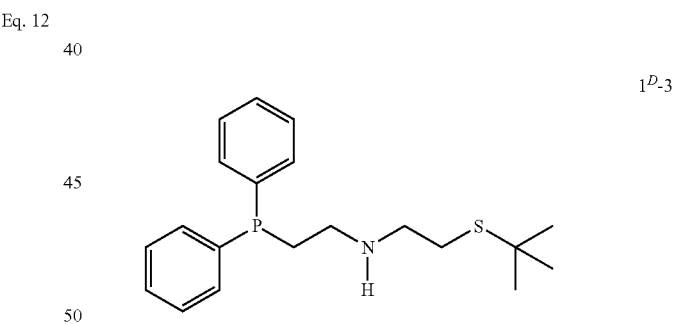

(Setup and Reaction)

By using a 200 mL four-necked round-bottom flask, a magnetic stirrer bar, a dropping funnel, a thermometer, and a three-way stopcock, a Ph$_2$PLi THF/n-hexane solution (52.9 mmol, 1.1 equivalents) was prepared in the same manner as in Step 3 of Example 1. Subsequently, 3-[2-(tert-butylthio)ethyl]-2-oxazolidinone ($2^C$-3) (9.8 g, 48.1 mmol, 1.0 equivalents) obtained in Step 1 and anhydrous THF (10 mL) were sequentially introduced into a dropping funnel, and added dropwise to the Ph$_2$PLi solution at such a rate that the inside temperature was kept at 30° C. or below over 30 minutes.

(Post Treatment, Isolation, and Purification)

The reaction liquid was concentrated under reduced pressure, and water (100 mL) and ethyl acetate (200 mL) were added, followed by stirring. Then, the mixture was allowed to stand, followed by liquid-liquid separation. The organic layer was concentrated under reduced pressure, and the obtained residue was purified by silica gel column chromatography (eluent: toluene/ethyl acetate/triethylamine=4/1/0.05 to 1/1/0.02) to obtain 13.6 g of title compound ($1^D$-3) as a light yellow viscous liquid. Isolated yield: 81.8%.

$^1$H NMR (400 MHz, CDCl$_3$): δ=7.45-7.39 (m, 4H), 7.36-7.30 (m, 6H), 2.82-2.71 (m, 4H), 2.65 (t, J=6.4 Hz, 2H), 2.30-2.24 (m, 2H), 1.63* (br s, 1H), 1.31 (s, 9H). (note that the peak attributable to water was included)

$^{31}$P NMR (161 MHz, CDCl$_3$): δ=−20.6.

(Example 7) Synthesis of 2-Diphenylphosphino-N-[2-(1-adamantylthio)ethyl]ethylamine (Structural Formula ($1^D$-4)) (Eq. 13)

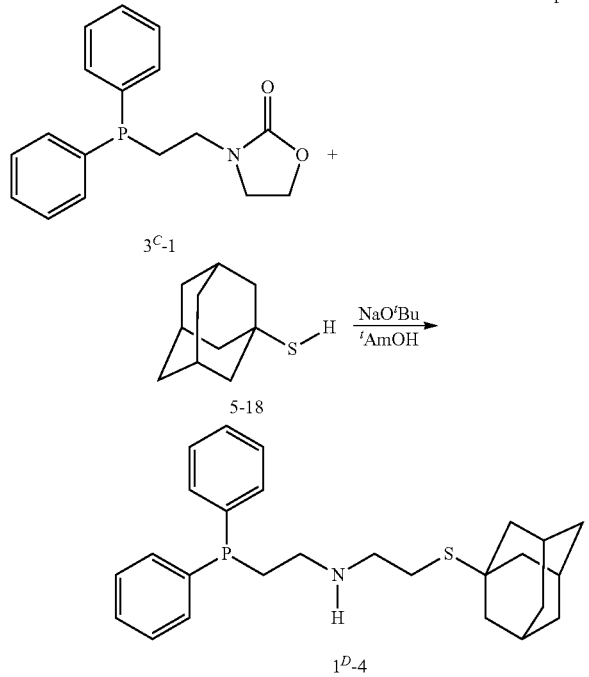

(Setup and Reaction)

To a 100 mL four-necked round-bottom flask, a magnetic stirrer bar, a condenser, a thermometer, and a three-way stopcock were attached, and the inside was purged with nitrogen. Then, 3-[2-(diphenylphosphino)ethyl]-2-oxazolidinone ($3^C$-1) (4.2 g, 14.0 mmol, 1.0 equivalents) obtained in Step 1 of Example 2, $^t$AmOH (28 mL), 1-adamantanethiol (5-18) (2.5 g, 14.9 mmol, 1.05 equivalents), and sodium tert-butoxide (NaO$^t$Bu) (1.5 g, 15.4 mmol, 1.1 equivalents) were sequentially added, and the obtained suspension was stirred for 1 hour under reflux.

(Post Treatment, Isolation, and Purification)

After the reaction liquid was cooled to room temperature, water (25 mL) and ethyl acetate (50 mL) were sequentially added, followed by stirring. Then, the mixture was allowed to stand, and the aqueous layer was separated. The organic layer was concentrated under reduced pressure, and then the obtained residue was purified by silica gel column chromatography (eluent: toluene/ethyl acetate/triethylamine=4/1/0.05 to 1/1/0.02) to obtain 4.0 g of title compound ($1^D$-4) as a yellow viscous liquid. Isolated yield: 67.5%.

$^1$H NMR (400 MHz, CDCl$_3$): δ=7.47-7.38 (m, 4H), 7.38-7.28 (m, 6H), 2.79-2.71 (m, 4H), 2.63 (t, J=6.0 Hz, 2H), 2.29-2.24 (m, 2H), 2.03 (br s, 3H), 1.83 (d, J=2.8 Hz, 6H), 1.73-1.62 (m, 6H), 1.52* (br s, 1H). (* note that a peak attributable to water was included)

$^{31}$P NMR (161 MHz, CDCl$_3$): δ=−20.7.

(Example 8) Synthesis of 2-Diphenylphosphino-N-[2-(phenylthio)ethyl]ethylamine (Structural Formula ($1^D$-5)) (Eq. 14)

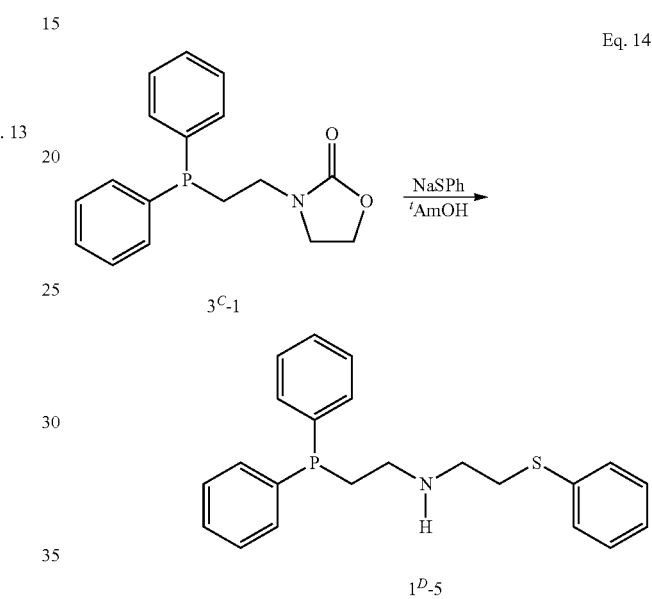

(Setup and Reaction)

To a 100 mL four-necked round-bottom flask, a magnetic stirrer bar, a condenser, a thermometer, and a three-way stopcock were attached, and the inside was purged with nitrogen. Then, 3-[2-(diphenylphosphino)ethyl]-2-oxazolidinone ($3^C$-1) (6.0 g, 20.0 mmol, 1.0 equivalents) obtained in Step 1 of Example 2, $^t$AmOH (40 mL), and sodium salt of benzenethiol (5-19) (NaSPh) (purity: 96.3%, 3.0 g, 22.0 mmol, 1.2 equivalents) were introduced sequentially, and the obtained suspension was stirred under reflux for 30 minutes.

(Post treatment and Purification)

The reaction liquid was cooled to room temperature, and water (20 mL) was added, followed by stirring. Then, the mixture was allowed to stand, followed by liquid-liquid separation. The organic layer was concentrated under reduced pressure, and the obtained residue was purified by silica gel column chromatography (eluent: toluene/ethyl acetate/triethylamine=1/1/0.02) to obtain 6.5 g of title compound ($1^D$-5) as a yellow viscous liquid. Isolated yield: 88.9%.

$^1$H NMR (300 MHz, CDCl$_3$): δ=7.51-7.14 (m, 15H), 3.02 (t, J=6.6 Hz, 2H), 2.80 (t, J=6.3 Hz, 2H), 2.84-2.69 (m, 4H), 2.25 (dd, J=7.2, 7.8 Hz, 2H), 1.64* (br s, 1H). (* note that the peak attributable to water was included)

$^{31}$P NMR (121 MHz, CDCl$_3$): δ=−20.6.

(Example 9) Synthesis of 2-Diphenylphosphino-N-[2-(p-tolylthio)ethyl]ethylamine (Structural Formula ($1^D$-6)) (Eq. 15)

(Example 10) Synthesis of 2-Dicyclohexylphosphino-N-[2-(methylthio)ethyl]ethylamine-Boron Trihydride Complex (Structural Formula ($1^D$-7)) (Eq. 16)

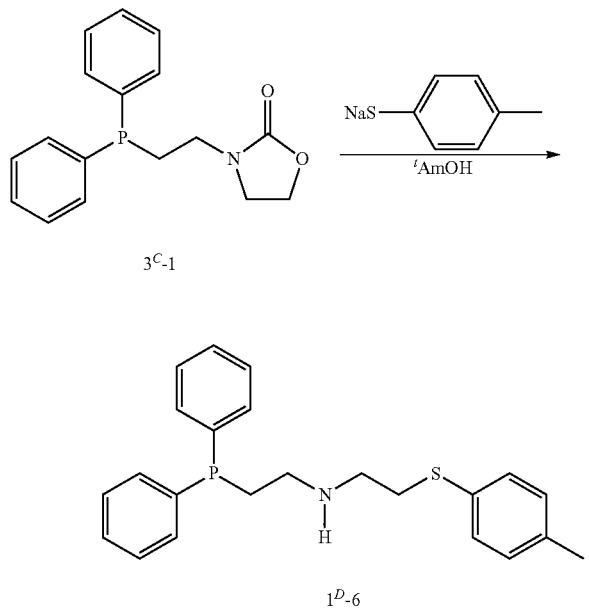

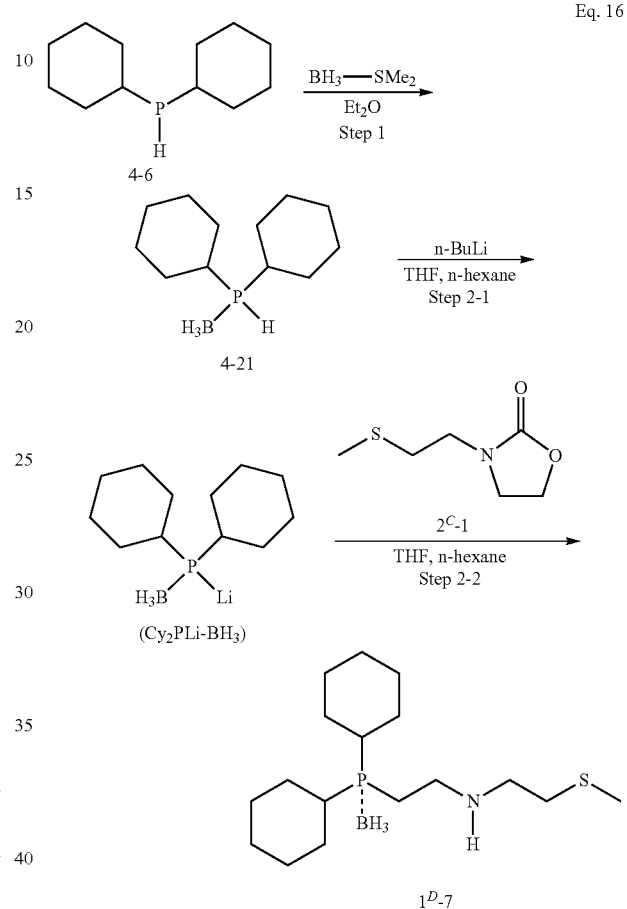

(Setup and Reaction)

To a 100 mL four-necked round-bottom flask, a magnetic stirrer bar, a condenser, a thermometer, and a three-way stopcock were attached, and the inside was purged with nitrogen. Then, 3-[2-(diphenylphosphino)ethyl]-2-oxazolidinone ($3^C$-1) (6.0 g, 20.0 mmol, 1.0 equivalents) obtained in Step 1 of Example 2, $^t$AmOH (40 mL), and sodium salt of p-toluenethiol (5-22) (sodium p-toluenethiolate) (purity: 98.3%, 3.3 g, 22.0 mmol, 1.2 equivalents) were introduced sequentially, and the obtained suspension was stirred under reflux for 30 minutes.

(Post treatment and Purification)

The reaction liquid was cooled to room temperature, and water (20 mL) was added, followed by stirring. Then, the mixture was allowed to stand, followed by liquid-liquid separation. The organic layer was concentrated under reduced pressure, and the obtained residue was purified by silica gel column chromatography (eluent: toluene/ethyl acetate/triethylamine=1/1/0.02) to obtain 6.5 g of title compound ($1^D$-6) as a yellow viscous liquid. Isolated yield: 85.6%.

$^1$H NMR (300 MHz, CDCl$_3$): δ=7.46-7.22 (m, 12H), 7.08 (d, J=8.4 Hz, 2H), 2.97 (t, J=6.6 Hz, 2H), 2.77 (t, J=6.6 Hz, 2H), 2.71 (t, J=8.1 Hz, 2H), 2.31 (s, 3H), 2.24 (dd, J=7.2, 8.1 Hz, 2H), 1.64* (br s, 1H). (* note that a peak attributable to water was included)

$^{31}$P NMR (121 MHz, CDCl$_3$): δ=−20.9.

Step 1: Synthesis of Dicyclohexylphosphine-Boron Trihydride Complex (Structural Formula (4-21))

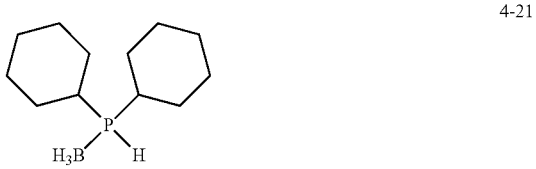

(Setup and Reaction)

To a 200 mL four-necked round-bottom flask, a magnetic stirrer bar, a dropping funnel, a thermometer, and a three-way stopcock were attached, and the inside was purged with nitrogen. Then, dicyclohexylphosphine (4-6) (20.0 mL, 91.2 mmol, 1.0 equivalents) and diethyl ether (Et$_2$O) (100 mL) were introduced sequentially, and the obtained solution was cooled to 5° C. in an ice-water bath. Subsequently, boron trihydride-dimethyl sulfide complex (BH$_3$—SMe$_2$) (concentration: 10.0 mol/L, 13.7 mL, 137.0 mmol, 1.5 equivalents)

was placed in a dropping funnel, and added dropwise to the solution at such a rate that the inside temperature was kept at 10° C. or below over 10 minutes. Then, the temperature of the reaction liquid was raised to normal temperature.
(Post Treatment, Isolation, and Purification)

After the reaction liquid was concentrated under reduced pressure, the obtained residue was dissolved in chloroform, and water was added, followed by stirring at normal temperature. Then, the mixture was allowed to stand, and the aqueous layer was separated. The organic layer was concentrated under reduced pressure, and the obtained solid was pulverized, and then dried under reduced pressure. Thus, 19.3 g of title compound (4-21) was obtained as a white powder. Isolated yield: 100%. This compound was used in the subsequent step without any further purification.

$^{31}$P NMR (161 MHz, deuterated methylene chloride (CD$_2$Cl$_2$)) δ=17.3-16.4 (m).

Step 2: Synthesis of 2-Dicyclohexylphosphino-N-[2-(methylthio)ethyl]ethylamine-Boron Trihydride Complex (Structural Formula (1$^D$-7))

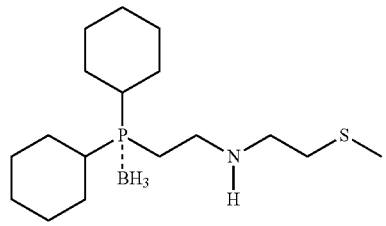

1$^D$-7

(Setup and Reaction)

To a 100 mL four-necked round-bottom flask, a magnetic stirrer bar, a dropping funnel, a thermometer, and a three-way stopcock were attached, and the inside was purged with nitrogen. Then, dicyclohexylphosphine-boron trihydride complex (4-21) (4.7 g, 22.0 mmol, 1.1 equivalents) obtained in Step 1 and anhydrous THF (22 mL) were introduced, and the obtained solution was cooled to 5° C. in an ice-water bath. A n-BuLi n-hexane solution (concentration: 1.60 mol/L, 13.1 mmol, 1.05 equivalents) was placed in a dropping funnel, and added dropwise to the solution at such a rate that the inside temperature was kept at 10° C. or below over 15 minutes. Then, the temperature of the reaction liquid was raised to normal temperature, followed by stirring for 30 minutes. Thus, a suspension of lithium dicyclohexylphosphide-boron trihydride complex (Cy$_2$PLi—BH$_3$) in THF/n-hexane was prepared. Subsequently, 3-[2-(methylthio)ethyl]-2-oxazolidinone (2$^C$-1) (3.2 g, 20.0 mmol, 1.0 equivalents) obtained in Step 2 of Example 1 and anhydrous THF (3 mL) were sequentially introduced into a dropping funnel, and added dropwise to the Cy$_2$PLi—BH$_3$ suspension at such a rate that the inside temperature was kept at 10° C. or below over 10 minutes. Then, the temperature of the reaction liquid was raised to room temperature, followed by stirring for 1 hour.
(Post Treatment, Isolation, and Purification)

After the reaction liquid was concentrated under reduced pressure, ethyl acetate (50 mL) and water (25 mL) were added to the obtained residue, followed by stirring. Then, the mixture was allowed to stand, and the aqueous layer was separated. The organic layer was washed sequentially with a 10% aqueous sodium chloride solution (25 mL) and water (25 mL), and then concentrated. The obtained residue was purified by silica gel chromatography (eluent: ethyl acetate to ethyl acetate/MeOH=50/1) to obtain 5.4 g of title compound (1$^D$-7) as a light yellow viscous liquid. Isolated yield: 82.0%.

$^1$H NMR (400 MHz, CD$_2$Cl$_2$): δ=2.88-2.76 (m, 4H), 2.61 (t, J=6.4 Hz, 2H), 2.08 (s, 3H), 1.92-1.17* (m, 23H), 0.90-(−0.30) (br q, 3H). (* note that a peak attributable to water was included)

$^{31}$P NMR (161 MHz, CD$_2$Cl$_2$): δ=22.4 (d, J=73.9 Hz, 1P).

(Example 11) Synthesis of Dichloro(triphenylphosphine){2-diphenylphosphino-N-[2-(methylthio)ethyl]ethylamine}ruthenium(II) (Structural Compositional Formula (8$^S$-1)) (Eq. 17)

Eq. 17

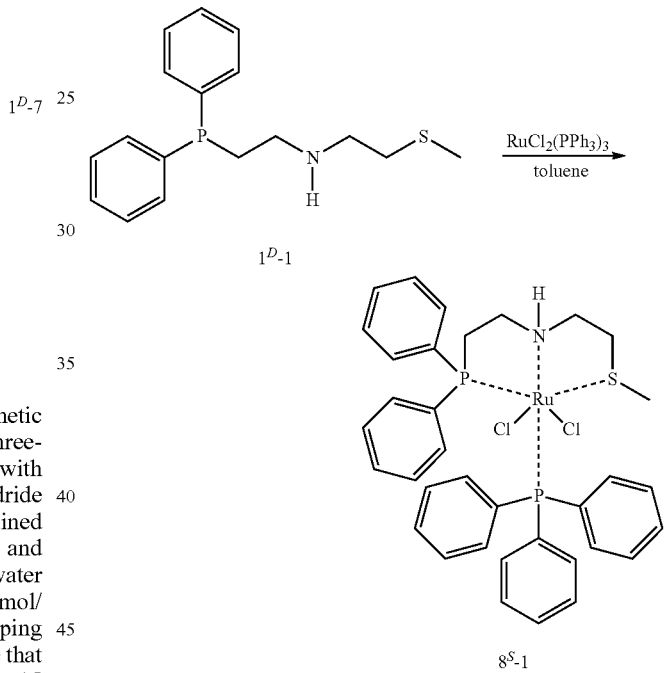

(Setup and Reaction)

To a 50 mL four-necked round-bottom flask, a magnetic stirrer bar, a condenser, a thermometer, and a three-way stopcock were attached, and the inside was purged with nitrogen. Then, dichlorotris(triphenylphosphine)ruthenium (II) (RuCl$_2$(PPh$_3$)$_3$) (2.88 g, 3.00 mmol, 1.0 equivalents), anhydrous toluene (30 mL), and 2-diphenylphosphino-N-[2-(methylthio)ethyl]ethylamine (1$^D$-1) (1.0 g, 3.30 mmol, 1.1 equivalents) obtained in Example 1/Example 2 were introduced sequentially, and the obtained dark purple suspension was stirred under reflux for 1 hour.
(Post Treatment, Isolation, and Purification)

The orange suspension obtained after the reaction was cooled to 5° C., and filtered by suction. Then, the crystals obtained by filtration were washed sequentially with toluene and n-hexane, and dried by heating under reduced pressure to obtain 2.17 g of title compound (8$^S$-1) as an orange powder. Isolated yield: 97.9%, Purity: 99.8% by weight (determined by $^1$H NMR analysis). Note that the major impurity was toluene. H NMR (400 MHz, CD$_2$Cl$_2$): See FIG. 1.

$^{31}$P NMR (161 MHz, CD$_2$Cl$_2$): δ=46.7-45.5 (m, 1P), 44.8-43.8 (m, 1P).

HRMS: Detected as molecular-mass ion (hereinafter, abbreviated as M+) of the title compound; actually measured value of mass-to-charge ratio (hereinafter, abbreviated as Meas. m/z)=737.0526, and predicted value of mass-to-charge ratio (hereinafter, abbreviated as Pred. m/z)=737.0546, compositional formula of molecular-mass ion (hereinafter, abbreviated as M) of title compound=C35H37NP2SCl2Ru.

(Example 12) Synthesis of Dichloro(triphenylphosphine){2-diphenylphosphino-N-[2-(ethylthio)ethyl]ethylamine}ruthenium(II) (Structural Compositional Formula ($8^S$-2)) (Eq. 18)

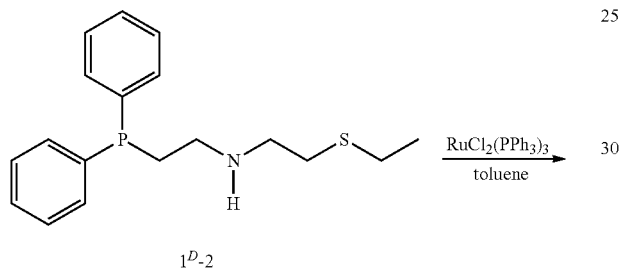

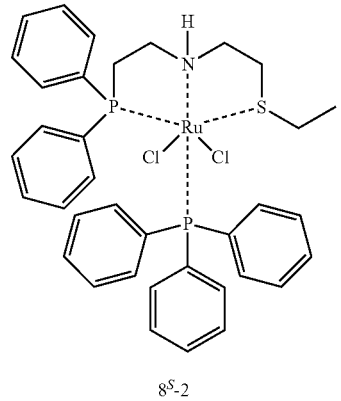

From RuCl$_2$(PPh$_3$)$_3$ (2.62 g, 2.73 mmol, 1.0 equivalents), anhydrous toluene (27 mL), and 2-diphenylphosphino-N-[2-(ethylthio)ethyl]ethylamine ($1^D$-2) (953 mg, 3.00 mmol, 1.1 equivalents) obtained in Example 3/Example 4, 2.06 g of title compound ($8^S$-2) was obtained as a bright reddish brown powder in the same manner as in Example 11. Isolated yield: 94.6%, Purity: 94.2% by weight (determined by $^1$H NMR analysis). Note that the major impurity was toluene.

Figure 2:
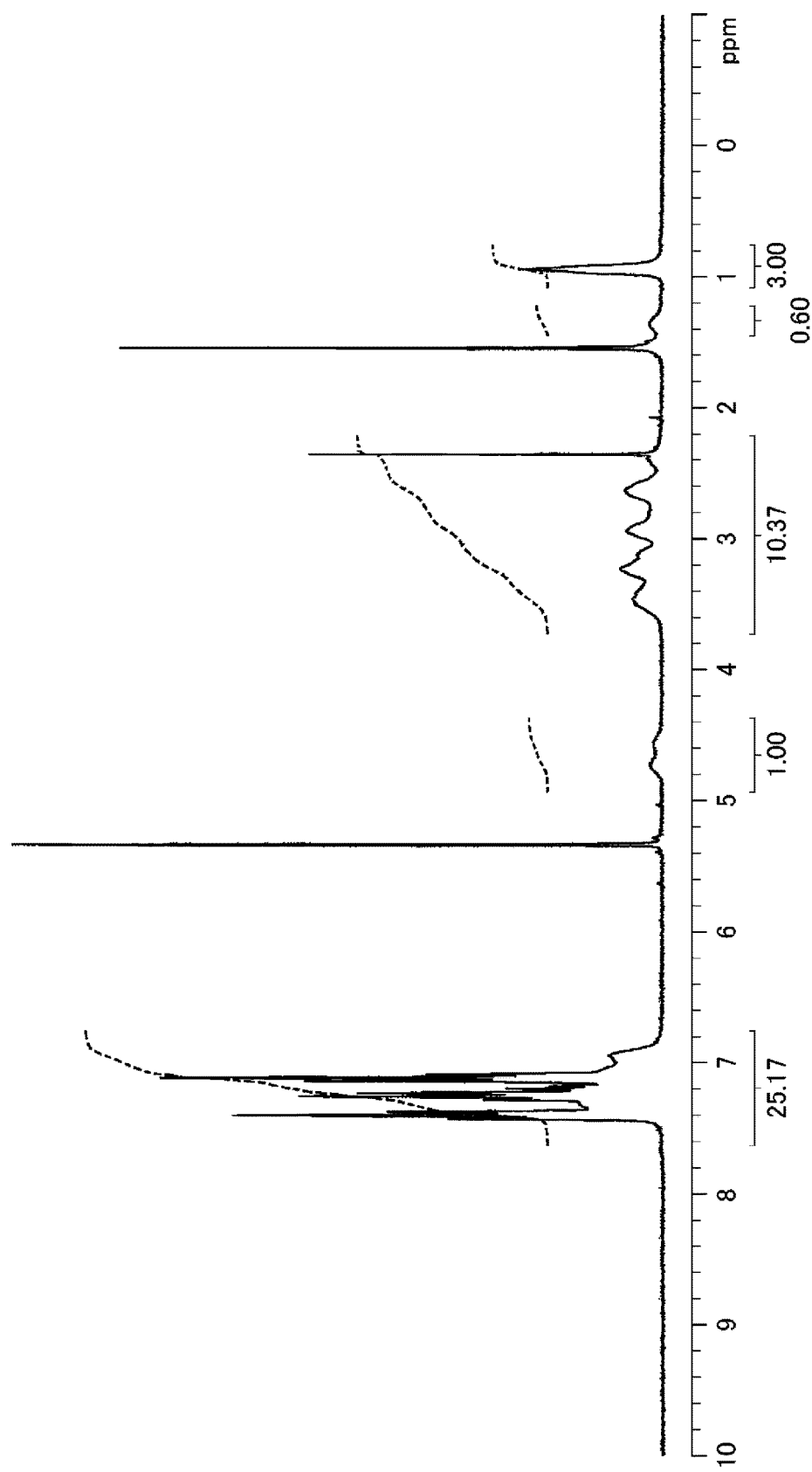
FIG. 2 is a $^1$H NMR chart of dichloro(triphenylphosphine){2-diphenylphosphino-N-[2-(ethylthio)ethyl]ethylamine}ruthenium(II) (8$^S$-2) (Example 12).

$^1$H NMR (300 MHz, CD$_2$Cl$_2$): See FIG. 2.

$^{31}$P NMR (121 MHz, CD$_2$Cl$_2$): δ=47.0-43.0 (m, 2P).

HRMS: Meas. m/z=751.0694, Pred. m/z=751.0697, M=C36H39NP2SCl2Ru.

(Example 13) Synthesis of Dichloro(triphenylphosphine) {2-diphenylphosphino-N-[2-(tert-butylthio)ethyl]ethylamine}ruthenium(II) (Structural Compositional Formula ($8^S$-3)) (Eq. 19)

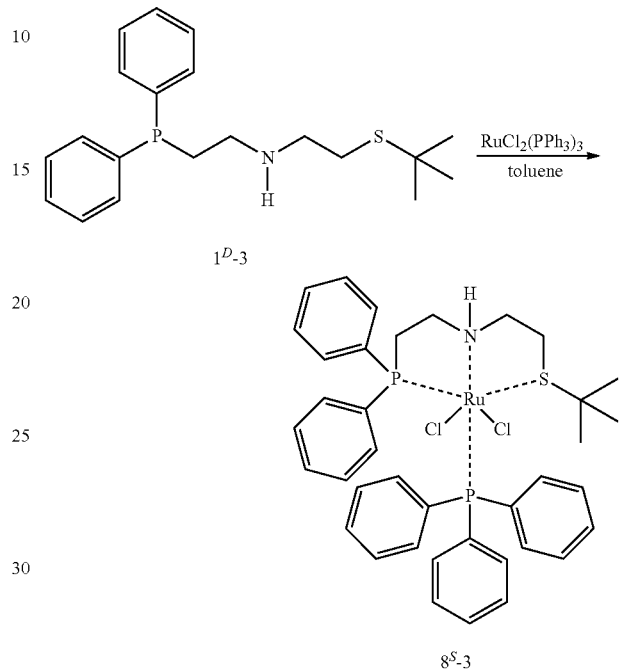

From RuCl$_2$(PPh$_3$)$_3$ (2.52 g, 2.63 mmol, 1.0 equivalents), anhydrous toluene (30 mL), and 2-diphenylphosphino-N-[2-(tert-butylthio)ethyl]ethylamine ($1^D$-3) (1.0 g, 2.89 mmol, 1.1 equivalents) obtained in Example 6, 1.54 g of title compound ($8^S$-3) was obtained as a light red powder in the same manner as in Example 11. Isolated yield: 70.3%, Purity: 93.6% by weight (determined by $^1$H NMR analysis). Note that the major impurity was toluene.

Figure 3:
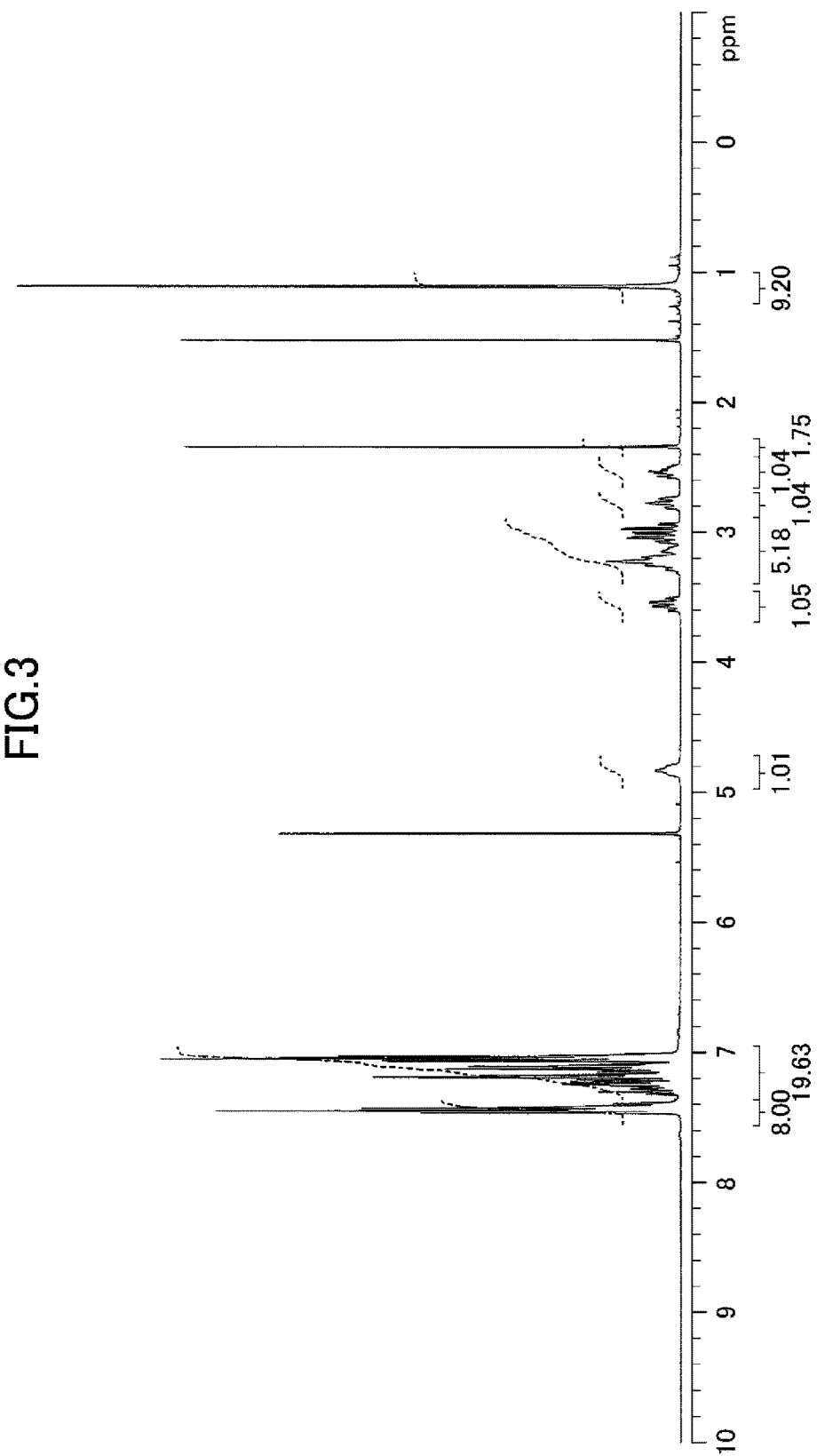
FIG. 3 is a $^1$H NMR chart of dichloro(triphenylphosphine){2-diphenylphosphino-N-[2-(tert-butylthio)ethyl]ethylamine}ruthenium(II) (8$^S$-3) (Example 13).

$^1$H NMR (400 MHz, CD$_2$Cl$_2$): See FIG. 3.

$^{31}$P NMR (161 MHz, CD$_2$Cl$_2$): δ=44.1 (d, J=28.0 Hz, 1P), 40.8 (d, J=31.1 Hz, 1P).

HRMS: Meas. m/z=779.1002, Pred. m/z=779.1016, M=C38H43NP2SCl2Ru.

(Example 14) Synthesis of Dichloro(triphenylphosphine) {2-diphenylphosphino-N-[2-(phenylthio)ethyl]ethylamine}ruthenium(II) (Structural Compositional Formula ($8^S$-4)) (Eq. 20)

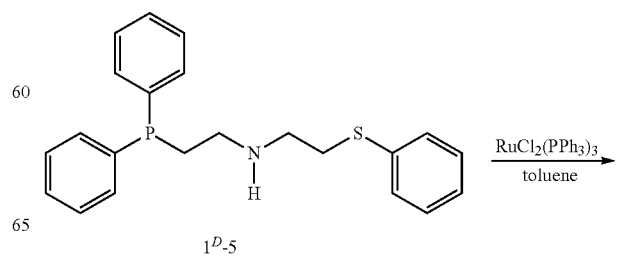

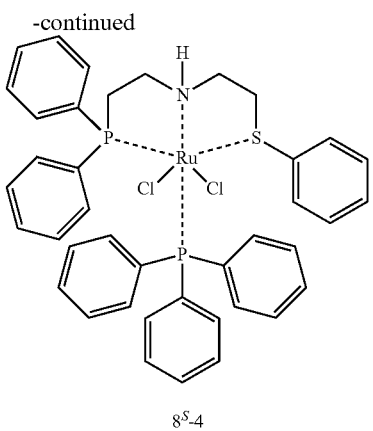

8<sup>S</sup>-4

From RuCl₂(PPh₃)₃ (1.0 g, 1.04 mmol, 1.0 equivalents), anhydrous toluene (20 mL), and 2-diphenylphosphino-N-[2-(phenylthio)ethyl]ethylamine (1$^D$-5) (332 mg, 1.14 mmol, 1.1 equivalents) obtained in Example 8, 780 mg of title compound (8$^S$-4) was obtained as a bright reddish brown powder in the same manner as in Example 11. Isolated yield: 99.3%, Purity: 95.8% by weight (determined by 1H NMR analysis). Note that the major impurity was toluene.

Figure 4:
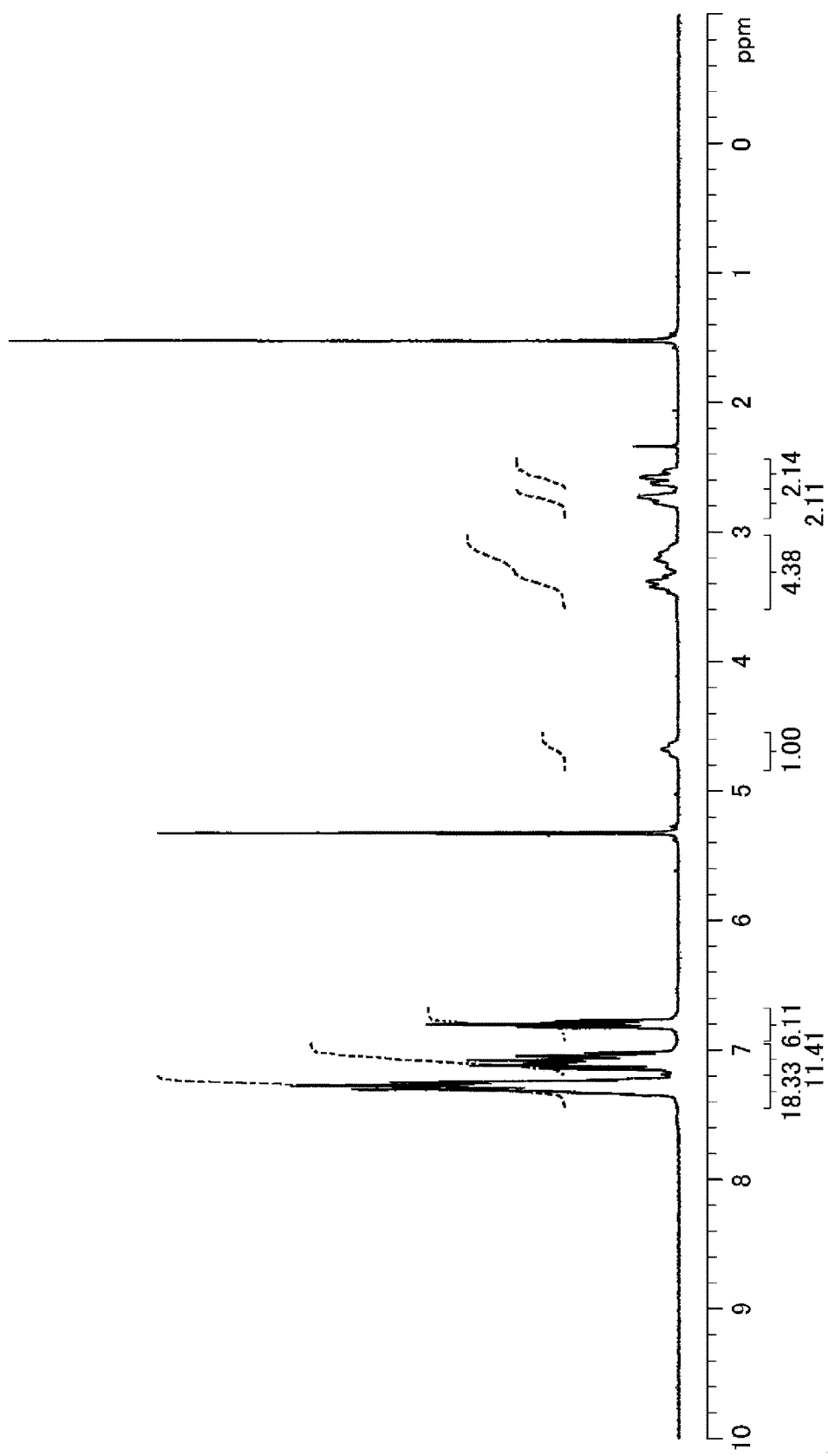
FIG. 4 is a $^1$H NMR chart of dichloro(triphenylphosphine) {2-diphenylphosphino-N-[2-(phenylthio)ethyl]ethylamine}ruthenium(II) (8$^S$-4) (Example 14).

$^1$H NMR (300 MHz, CD₂Cl₂): See FIG. 4.
$^{31}$P NMR (121 MHz, CD₂Cl₂): Unmeasurable because of low solubility.
HRMS: M⁺, Meas. m/z=799.0725, Pred. m/z=799.0698, M=C40H39NP2SCl2Ru.

(Example 15) Synthesis of Dichloro(triphenylphosphine){2-diphenylphosphino-N-[2-(p-tolylthio)ethyl]ethylamine}ruthenium(II) (Structural Compositional Formula (8$^S$-5)) (Eq. 21)

Eq. 21

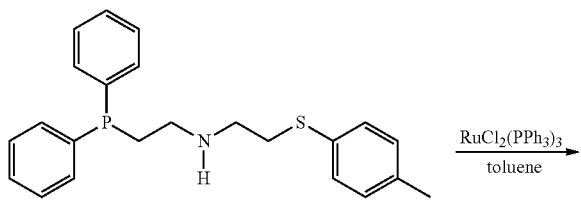

1$^D$-6

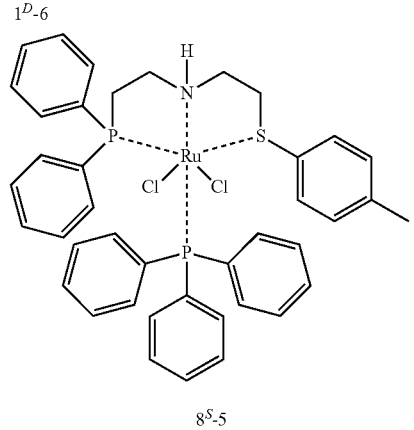

8$^S$-5

From RuCl₂(PPh₃)₃ (2.30 g, 2.40 mmol, 1.0 equivalents), anhydrous toluene (23 mL), and 2-diphenylphosphino-N-[2-(p-tolylthio)ethyl]ethylamine (1$^D$-6) (1.00 g, 2.64 mmol, 1.1 equivalents) obtained in Example 9, 1.88 g of title compound (8$^S$-5) was obtained as a bright reddish brown powder in the same manner as in Example 11. Isolated yield: 96.3%.

Figure 5:
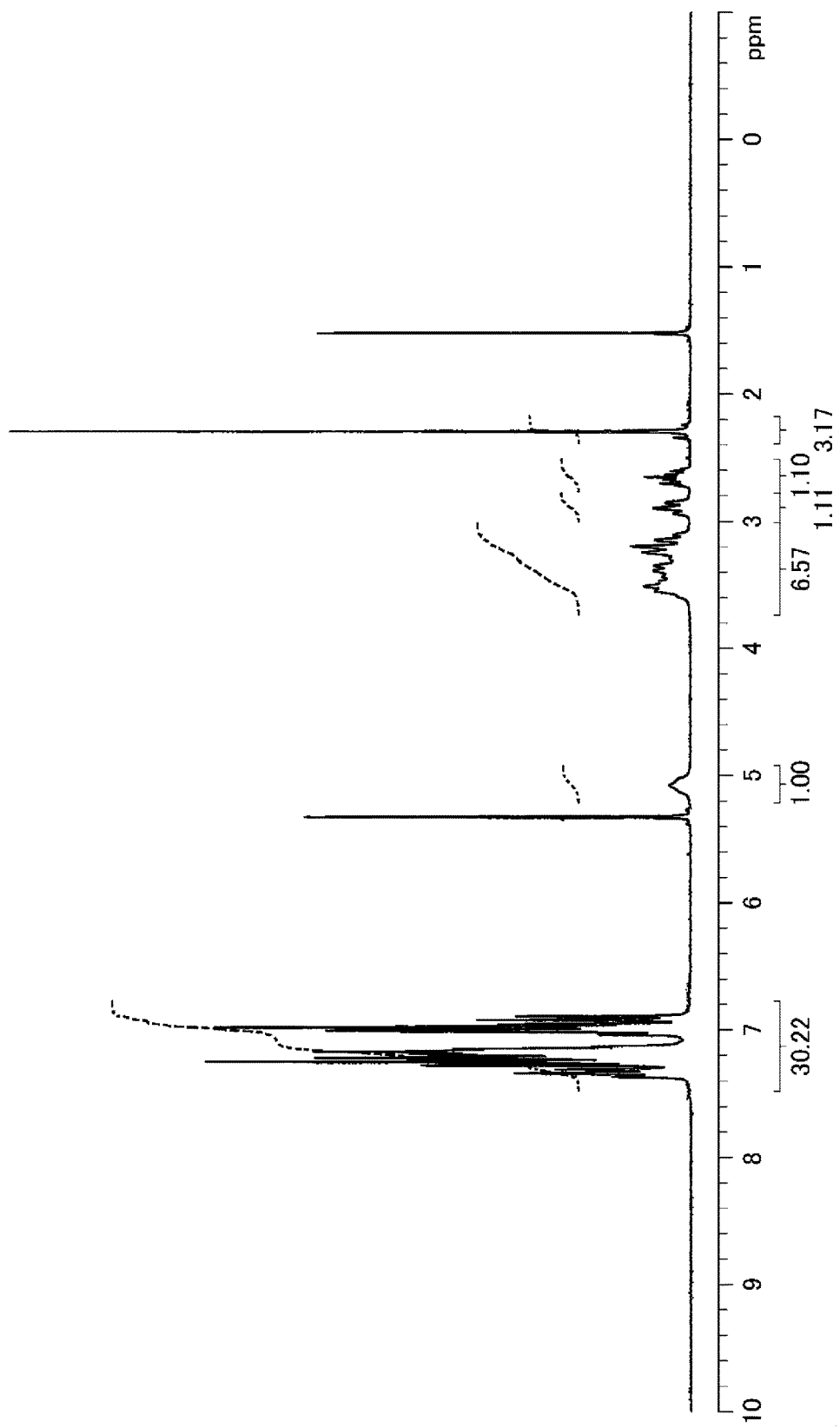
FIG. 5 is a $^1$H NMR chart of dichloro(triphenylphosphine){2-diphenylphosphino-N-[2-(p-tolylthio)ethyl]ethylamine}ruthenium(II) (8$^S$-5) (Example 15).

$^1$H NMR (300 MHz, CD₂Cl₂): See FIG. 5.
$^{31}$P NMR (121 MHz, CD₂Cl₂): δ=45.4 (br s, 1P), 44.0 (d, J=31.0 Hz, 1P).
HRMS: M⁺; Meas. m/z=813.0882, Pred. m/z=813.0855, M=C41H41NP2SCl2Ru.

(Example 16) Synthesis of Dichloro(trimethylphosphine){2-diphenylphosphino-N-[2-(ethylthio)ethyl]ethylamine}ruthenium(II) (Structural Compositional Formula (8$^3$-6)) (Eq. 22)

Eq. 22

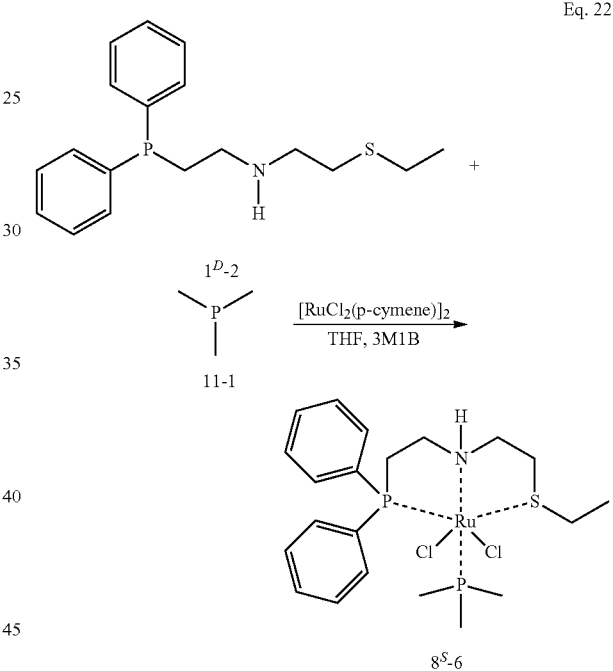

(Setup and Reaction)

To a 50 mL four-necked round-bottom flask, a magnetic stirrer bar, a Claisen distillation apparatus, a condenser, a thermometer, and a three-way stopcock were attached, and the inside was purged with nitrogen. Then, dichloro(p-cymene)ruthenium(II) dimer ([RuCl₂(p-cymene)]₂) (791 mg, 1.29 mmol, 1.0 equivalents) and 3-methoxy-1-butanol (3M1B) (9 mL) were sequentially introduced, and the obtained dark red suspension was degassed under reduced pressure. Subsequently, a solution of trimethylphosphine (11-1) in THF (concentration: 1.03 mol/L, 2.80 mL, 2.84 mmol, 2.2 equivalents) was introduced, and stirred at room temperature for 5 minutes. To the obtained orange suspension, 2-diphenylphosphino-N-[2-(ethylthio)ethyl]ethylamine (1$^D$-2) (900 mg, 2.84 mmol, 2.2 equivalents) obtained in Example 3/Example 4 was added. Then, THF was removed by distillation at normal pressure using the Claisen distillation apparatus, followed by stirring for 1 hour under reflux in 3M1B.

(Post Treatment, Isolation, and Purification)

The reaction liquid was cooled to 5° C., and the obtained yellowish orange suspension was filtered by suction. Then, the crystals obtained by filtration were washed with MeOH, and dried by heating under reduced pressure. Thus, 920 mg of title compound ($8^S$-6) was obtained as a yellowish orange powder. Isolated yield: 63.1%.

Figure 6:
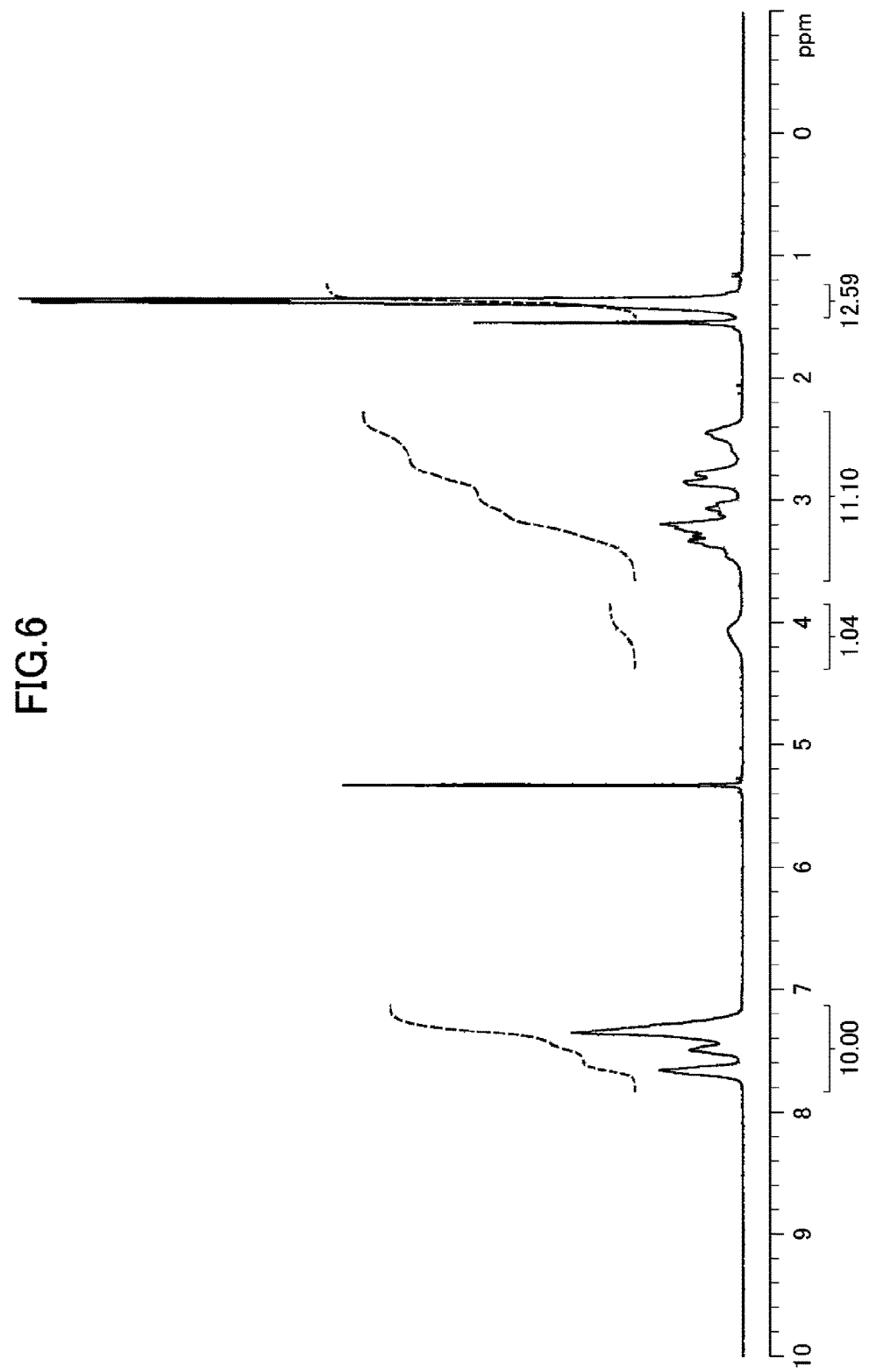
FIG. 6 is a $^1$H NMR chart of dichloro(trimethylphosphine){2-diphenylphosphino-N-[2-(ethylthio)ethyl]ethylamine}ruthenium(II) (8$^S$-6) (Example 16).

$^1$H NMR (300 MHz, CD$_2$Cl$_2$): See FIG. 6.

$^{31}$P NMR (121 MHz, CD$_2$Cl$_2$): δ=56.1 (br s, 1P), 9.7 (br s, 1P).

HRMS: M$^+$; Meas. m/z=565.0221, Pred. m/z=565.0223, M=C21H33NP2SCl2Ru.

(Example 17) Synthesis of Dichloro(trimethylphosphine) {2-diphenylphosphino-N-[2-(phen ylthio)ethyl]ethylamine}ruthenium(II) (Structural Compositional Formula ($8^S$-7)) (Eq. 23)

Eq. 23

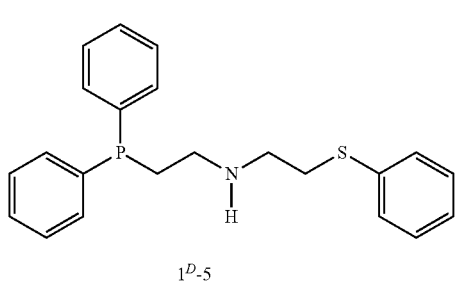

$1^D$-5

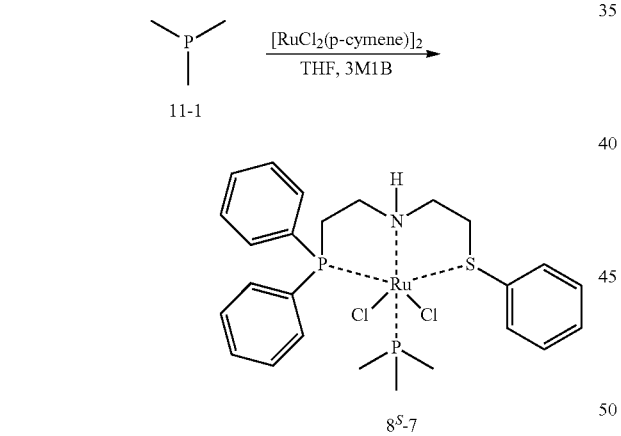

$8^S$-7

From [RuCl$_2$ (p-cymene)]$_2$ (762 mg, 1.25 mmol, 1.0 equivalents), 3M1B (10 mL), a solution of trimethylphosphine (11-1) in THF (concentration: 1.03 mol/L, 2.70 mL, 2.74 mmol, 2.2 equivalents), and 2-diphenylphosphino-N-[2-(phenylthio)ethyl]ethylamine ($1^D$-5) (1.00 g, 2.74 mmol, 2.2 equivalents) obtained in Example 8, 990 mg of title compound ($8^S$-7) was obtained as an orange powder in the same manner as in Example 16. Isolated yield: 64.5%.

Figure 7:
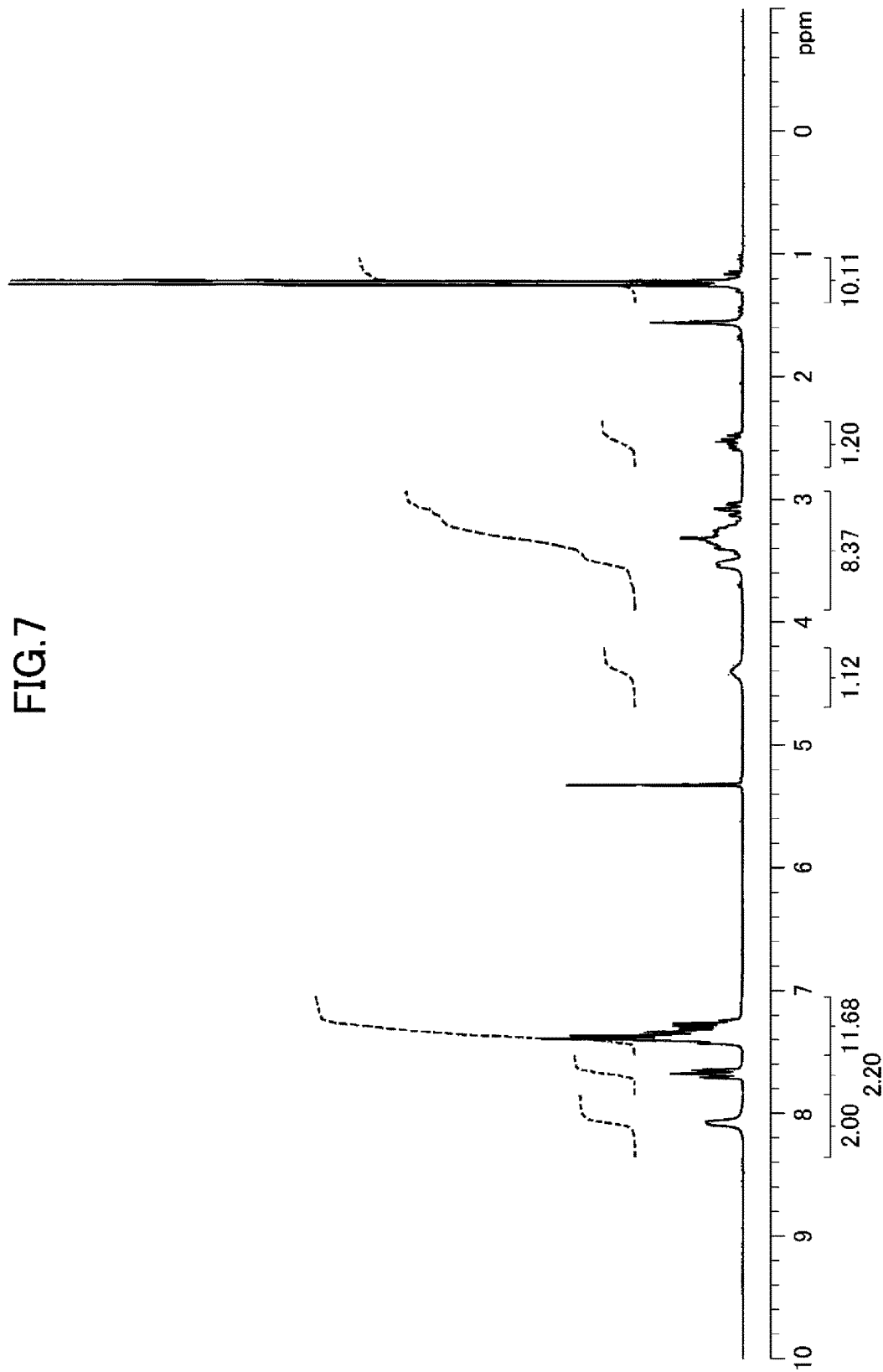
FIG. 7 is a $^1$H NMR chart of dichloro(trimethylphosphine){2-diphenylphosphino-N-[2-(phenylthio)ethyl] ethylamine}ruthenium(II) ($8^S$-7) (Example 17).

$^1$H NMR (300 MHz, CD$_2$Cl$_2$): See FIG. 7.

$^{31}$P NMR (121 MHz, CD$_2$Cl$_2$): δ=57.5 (d, J=32.4 Hz, 1P), 8.6 (d, J=34.0 Hz, 1P).

HRMS: M$^+$; Meas. m/z=613.0184, Pred. m/z=613.0224, M=C25H33NP2SCl2Ru.

(Example 18) Synthesis of Dichloro(triethylphosphine){2-diphenylphosphino-N-[2-(ethyl thio)ethyl]ethylamine}ruthenium(II) (Structural Compositional Formula ($8^S$-8)) (Eq. 24)

Eq. 24

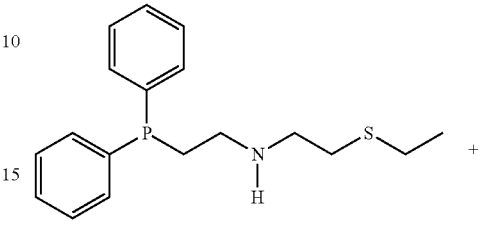

$1^D$-2

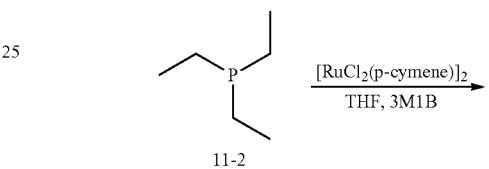

11-2

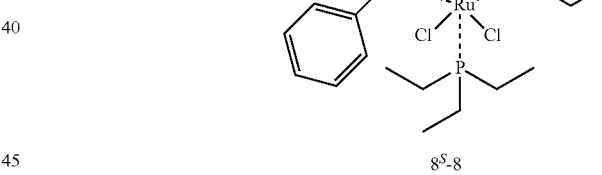

$8^S$-8

From [RuCl$_2$ (p-cymene)]$_2$ (877 mg, 1.43 mmol, 1.0 equivalents), 3M1B (15 mL), a solution of triethylphosphine (11-2) in THF (concentration: 1.03 mol/L, 3.06 mL, 3.15 mmol, 2.2 equivalents), and 2-diphenylphosphino-N-[2-(ethylthio)ethyl]ethylamine ($1^D$-2) (1.00 g, 3.15 mmol, 2.2 equivalents) obtained in Example 3/Example 4, 1.13 g of title compound ($8^S$-6) was obtained as a yellowish brown powder in the same manner as in Example 16. Isolated yield: 64.4%, Purity: 99.1% by weight (determined by $^1$H NMR). Note that the major impurity was 3M1B.

Figure 8:
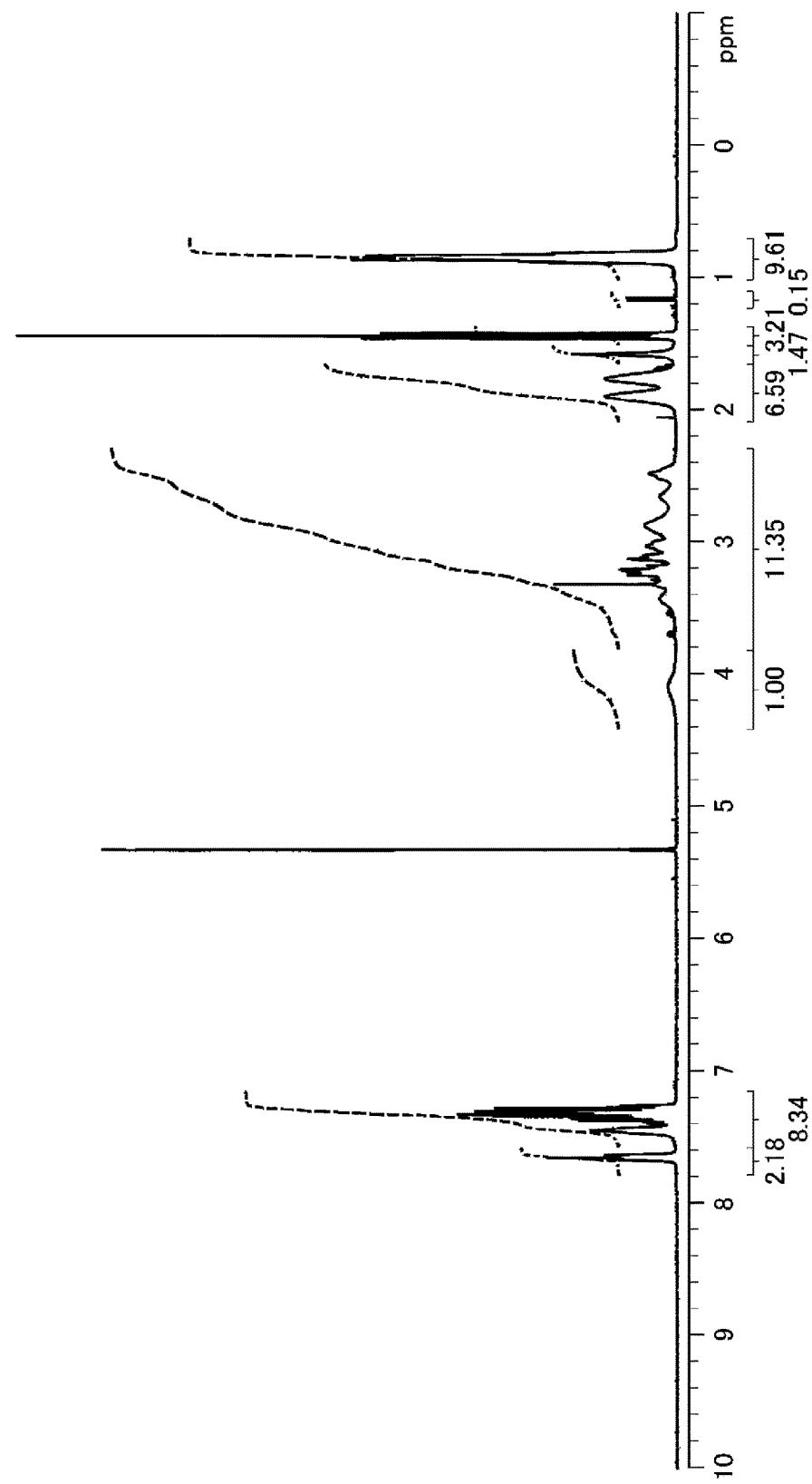
FIG. 8 is a $^1$H NMR chart of dichloro(triethylphosphine) {2-diphenylphosphino-N-[2-(ethylthio)ethyl] ethylamine}ruthenium(II) ($8^S$-8) (Example 18).

$^1$H NMR (400 MHz, CD$_2$Cl$_2$): See FIG. 8.

$^{31}$P NMR (161 MHz, CD$_2$Cl$_2$): δ=52.7 (br s, 1P), 29.8 (br s, 1P) HRMS: Detected as a molecular-mass ion formed by dissociation of one chloride ion from the title compound (hereinafter, this ion is abbreviated as [M-Cl]$^+$); Meas. m/z=572.1022, Pred. m/z=572.1008, compositional formula of molecular-mass ion formed by dissociation of one chloride ion from the title compound (hereinafter, abbreviated as M-Cl)=C24H39NP2SClRu.

(Example 19) Synthesis of Dichloro(tricyclohexylphosphine){2-diphenylphosphino-N-[2-(ethylthio)ethyl]ethylamine}ruthenium(II) (Structural Compositional Formula ($8^S$-9)) (Eq. 25)

(Example 20) Synthesis of Dichloro[tris(4-methoxyphenyl)phosphine]{2-diphenylphosphino-N-[2-(methylthio)ethyl]ethylamine}ruthenium(II) (Structural Compositional Formula (8-10)) (Eq. 26)

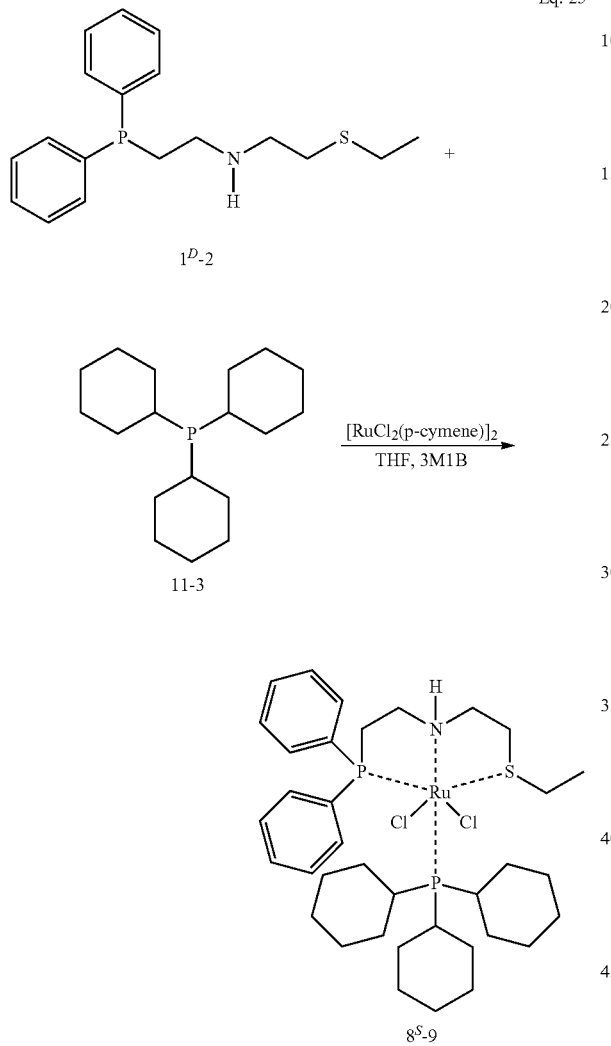

Eq. 25

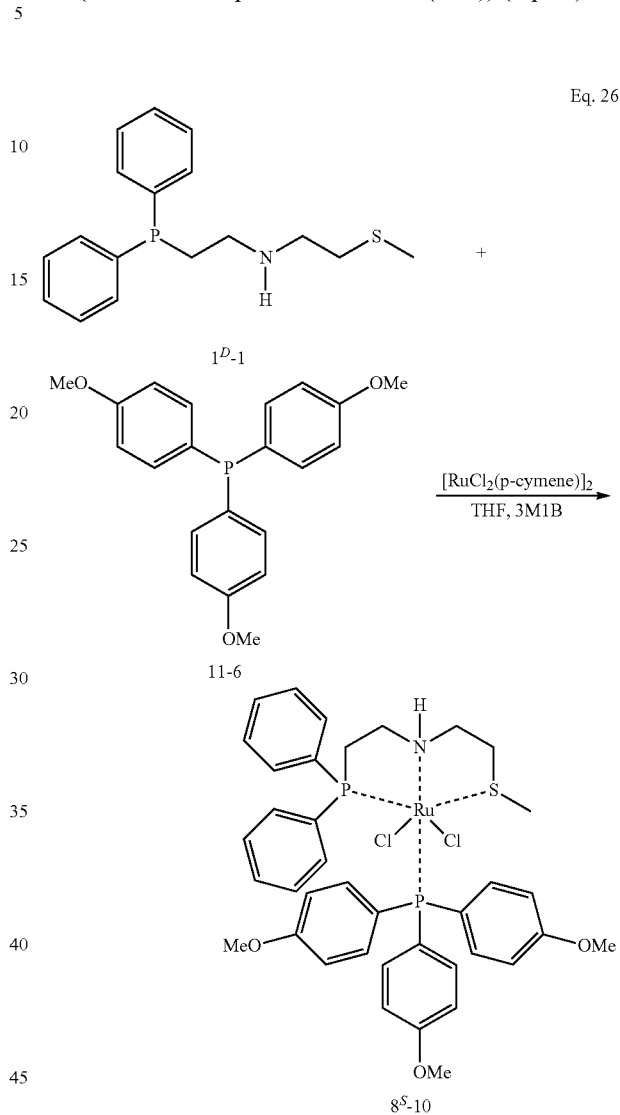

Eq. 26

By a reaction of [RuCl$_2$(p-cymene)]$_2$ (877 mg, 1.43 mmol, 1.0 equivalents), 3M1B (10 mL), a solution of tricyclohexylphosphine (11-3) in toluene (concentration: 1.04 mol/L, 3.03 mL, 3.15 mmol, 2.2 equivalents), and 2-diphenylphosphino-N-[2-(ethylthio)ethyl]ethylamine ($1^D$-2) (1.00 g, 3.15 mmol, 2.2 equivalents) obtained in Example 3/Example 4 under reflux in toluene/3M1B, 1.25 g of title compound ($8^S$-9) was obtained as a bright brown powder in the same manner as in Example 16, except that THF was not removed by distillation. Isolated yield: 50.0%, Purity: 88.1% by weight (determined by $^1$H NMR). Note that the major impurity was 3M1B.

Figure 9:
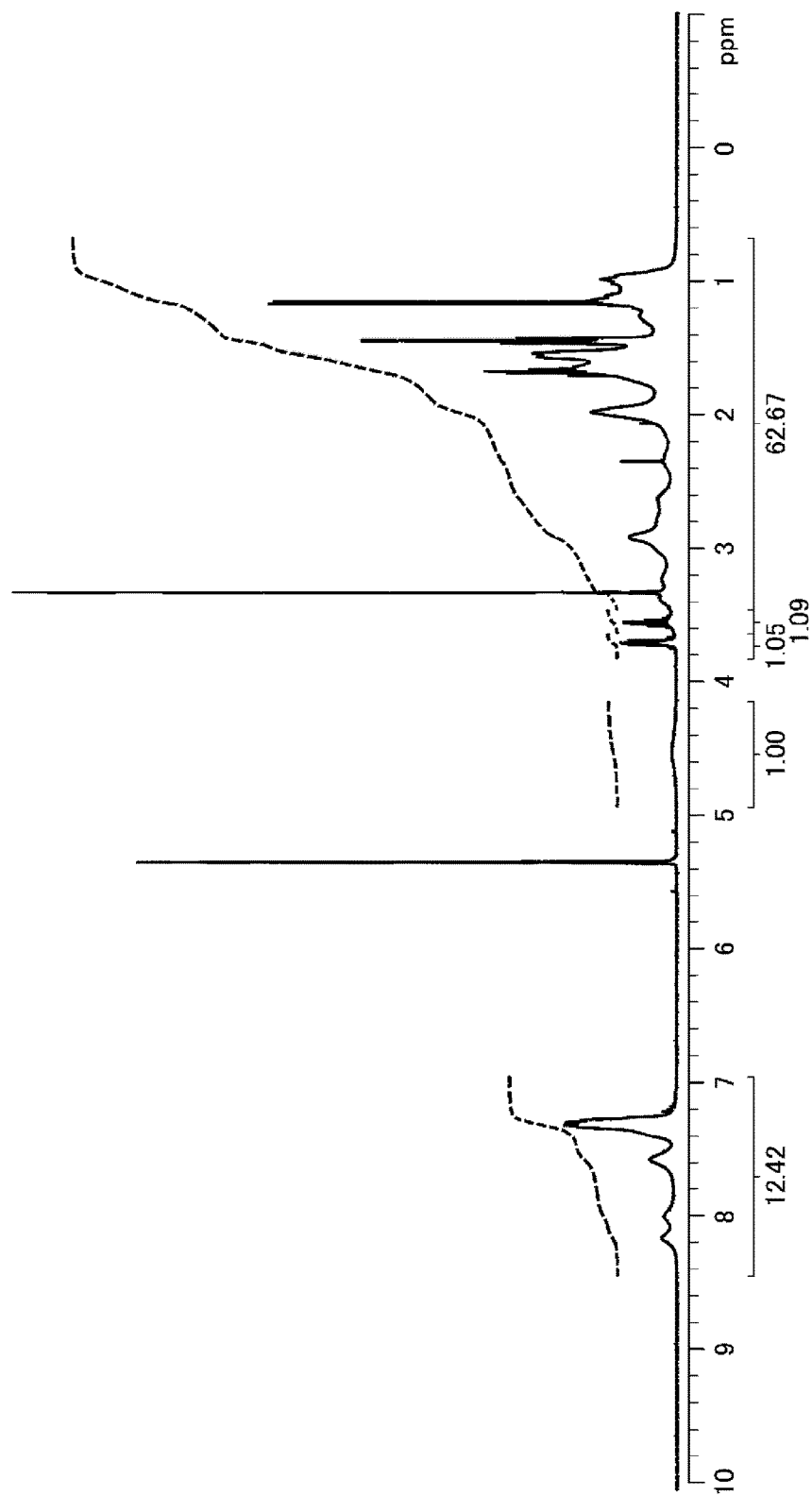
FIG. 9 is a $^1$H NMR chart of dichloro(tricyclohexylphosphine) {2-diphenylphosphino-N-[2-(ethylthio)ethyl] ethylamine}ruthenium(II) ($8^S$-9) (Example 19).

$^1$H NMR (400 MHz, CD$_2$Cl$_2$): See FIG. 9.

$^{33}$P NMR (161 MHz, CD$_2$Cl$_2$): δ=44.0-32.0 (m, 2P).

HRMS: [M-Cl]$^+$; Meas. m/z=734.244, Pred. m/z=734.242, M-Cl=C36H57NP2SC1Ru.

(Setup and Reaction)

To a 50 mL four-necked round-bottom flask, a magnetic stirrer bar, a Claisen distillation apparatus, a condenser, a thermometer, and a three-way stopcock were attached, and the inside was purged with nitrogen. Then, [RuCl$_2$(p-cymene)]$_2$ (459 mg, 0.75 mmol, 1.0 equivalents), tris(4-methoxyphenyl)phosphine (11-6) (581 mg, 1.65 mmol, 2.2 equivalents), and anhydrous THF (5 mL) were introduced sequentially, and the obtained dark red suspension was stirred at room temperature for 5 minutes. Subsequently, 2-diphenylphosphino-N-[2-(methylthio)ethyl]ethylamine ($1^D$-1) (500 mg, 1.65 mmol, 2.2 equivalents) obtained in Example 1/Example 2 and 3M1B (10 mL) were added, and THF was removed by distillation at normal pressure using the Claisen distillation apparatus, followed by stirring for 1 hour under reflux in 3M1B.

(Post Treatment, Isolation, and Purification)

The reaction liquid was cooled to 5° C., and MeOH (20 mL) was added to the obtained yellowish orange suspension, followed by filtration by suction. Then, the crystals obtained by filtration were washed with MeOH, and dried by heating under reduced pressure to obtain 922 mg of title compound ($8^S$-10) as a yellowish orange powder. Isolated yield: 73.5%, Purity: 99.0% by weight. Note that the major impurity was 3M1B.

Figure 10:
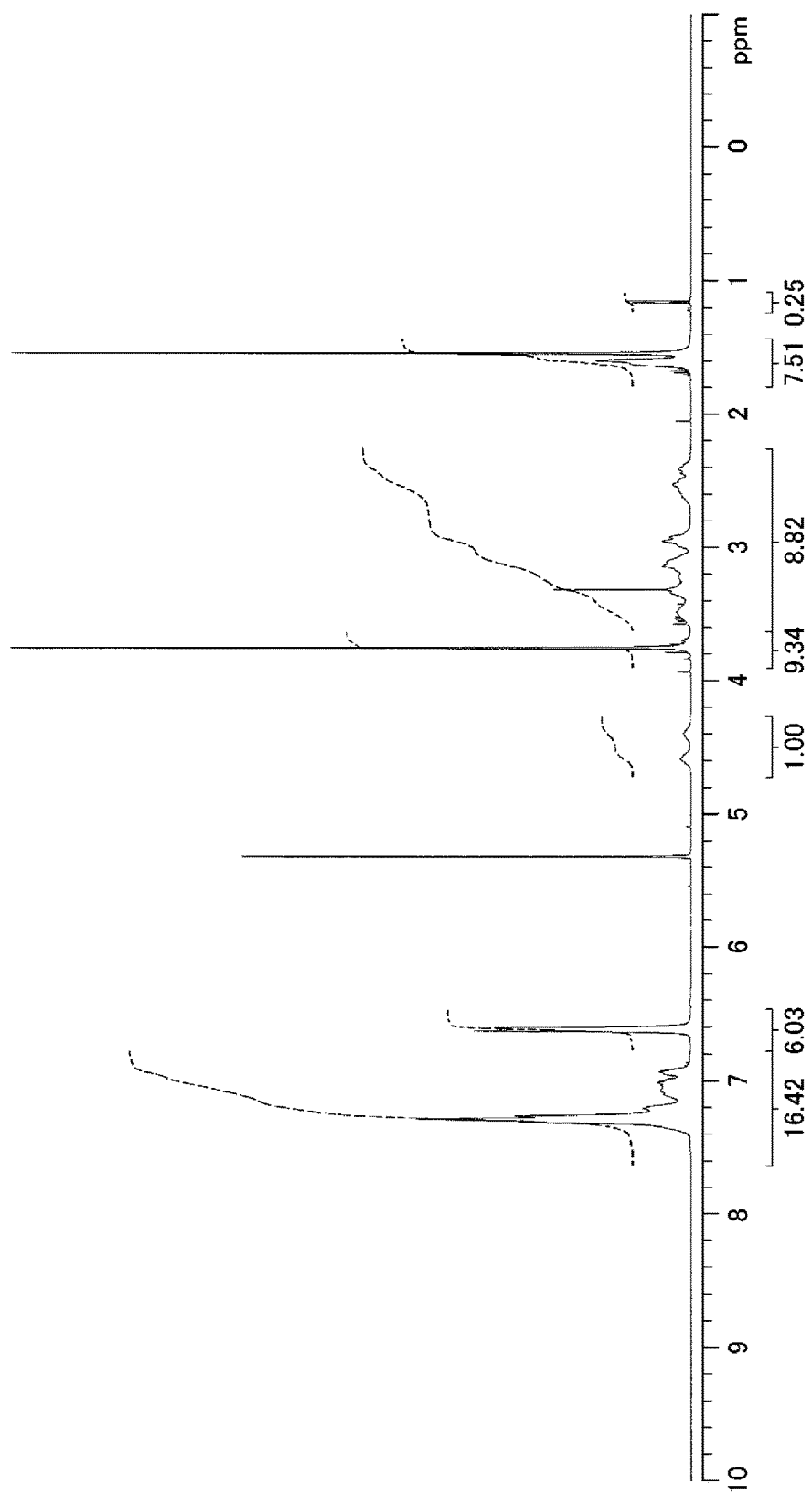
FIG. 10 is a $^1$H NMR chart of dichloro[tris(4-methoxyphenyl)phosphine]{2-diphenylphosphino-N-[2-(methylthio)ethyl]ethylamine}ruthenium(II) ($8^S$-10) (Example 20).

$^1$H NMR (400 MHz, CD$_2$Cl$_2$): See FIG. 10.
$^{31}$P NMR (161 MHz, CD$_2$Cl$_2$): δ=47.0-45.6 (m, 1P), 40.1-39.4 (m, 1P).

(Example 21) Synthesis of Dichloro[tris(4-methoxyphenyl)phosphine]{2-diphenylphosphino-N-[2-(ethylthio)ethyl]ethylamine}ruthenium(II) (Structural Compositional Formula ($8^S$-11)) (Eq. 27)

HRMS: M$^+$; Meas. m/z=841.0994, Pred. m/z=841.1015, M=C39H45NO3P2SCl2Ru.

(Example 22) Synthesis of Dichloro[tris(4-trifluoromethylphenyl)phosphine]{2-diphenyl phosphino-N-[2-(ethylthio)ethyl]ethylamine}ruthenium(II) (Structural Compositional Formula ($8^S$-12)) (Eq. 28)

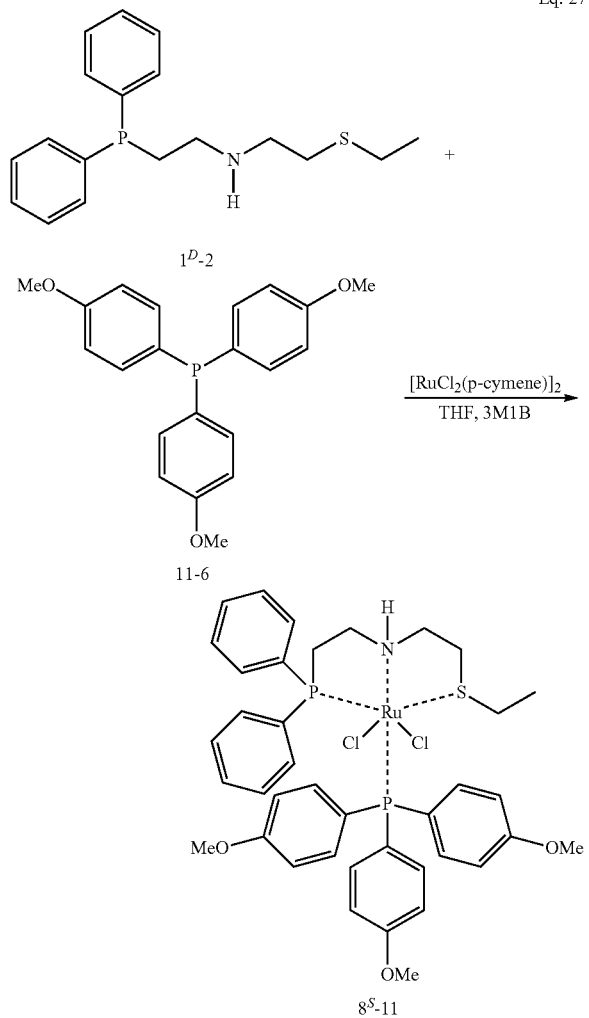

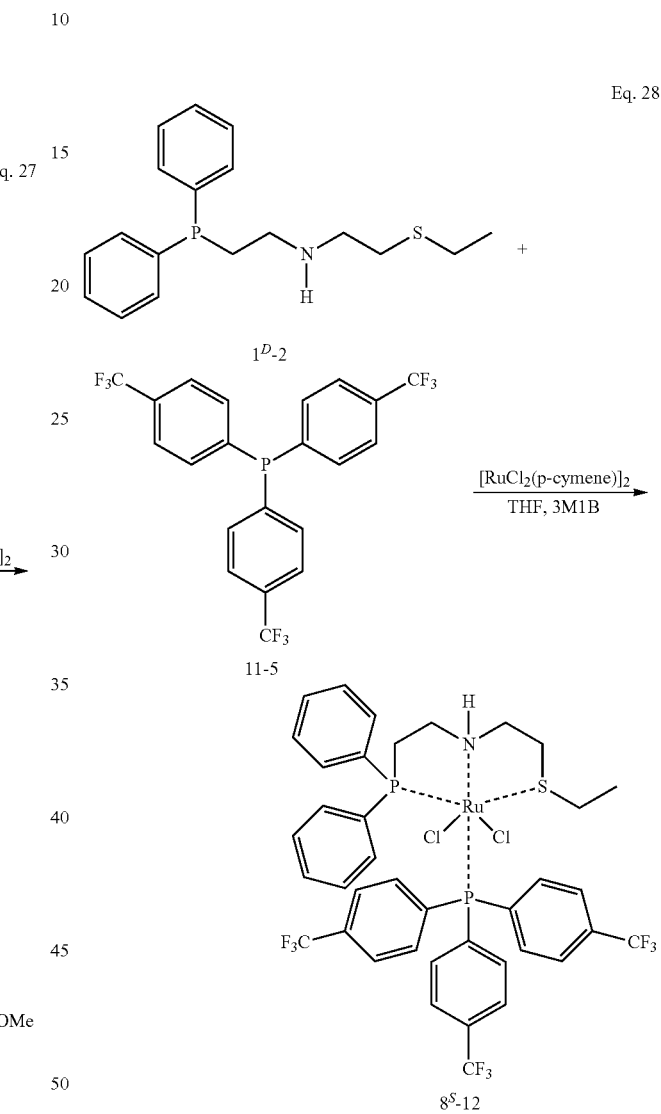

From [RuCl$_2$(p-cymene)]$_2$ (877 mg, 1.43 mmol, 1.0 equivalents), tris(4-methoxyphenyl)phosphine (11-6) (1.11 g, 3.15 mmol, 2.2 equivalents), anhydrous THF (10 mL), 2-diphenylphosphino-N-[2-(ethylthio)ethyl]ethylamine ($1^D$-2) (1.0 g, 3.15 mmol, 2.2 equivalents) obtained in Example 3/Example 4, and 3M1B (20 mL), 1.98 g of title compound ($8^S$-11) was obtained as a light brown powder in the same manner as in Example 20. Isolated yield: 81.1%, Purity: 98.7% by weight. Note that the major impurity was 3M1B.

Figure 11:
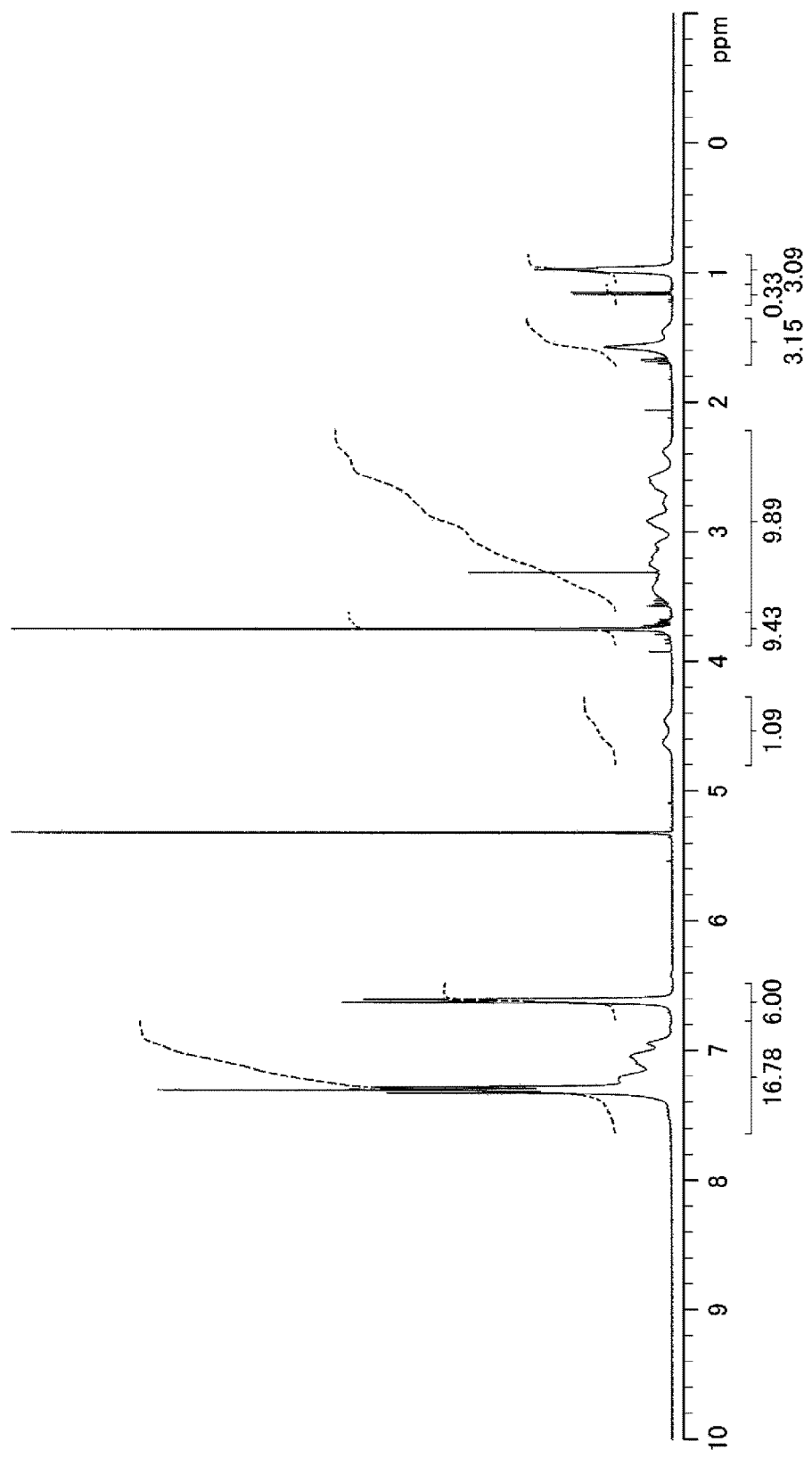
FIG. 11 is a $^1$H NMR chart of dichloro[tris(4-methoxyphenyl)phosphine]{2-diphenylphosphino-N-[2-(ethylthio) ethyl]ethylamine}ruthenium(II) ($8^S$-11) (Example 21).

$^1$H NMR (400 MHz, CD$_2$Cl$_2$): See FIG. 11.
$^{31}$P NMR (161 MHz, CD$_2$Cl$_2$): δ=46.5-44.8 (m, 1P), 40.4-38.8 (m, 1P).

From [RuCl$_2$ (p-cymene)]$_2$ (438 mg, 0.72 mmol, 1.0 equivalents), tris(4-trifluoromethylphenyl)phosphine (11-5) (737 mg, 1.58 mmol, 2.2 equivalents), anhydrous THF (5 mL), 2-diphenylphosphino-N-[2-(ethylthio)ethyl]ethylamine ($1^D$-2) (500 mg, 1.58 mmol, 2.2 equivalents) obtained in Example 3/Example 4, and 3M1B (10 mL), 1.09 g of title compound ($8^S$-12) was obtained as an orange powder in the same manner as in Example 20. Isolated yield: 79.6%.

Figure 12:
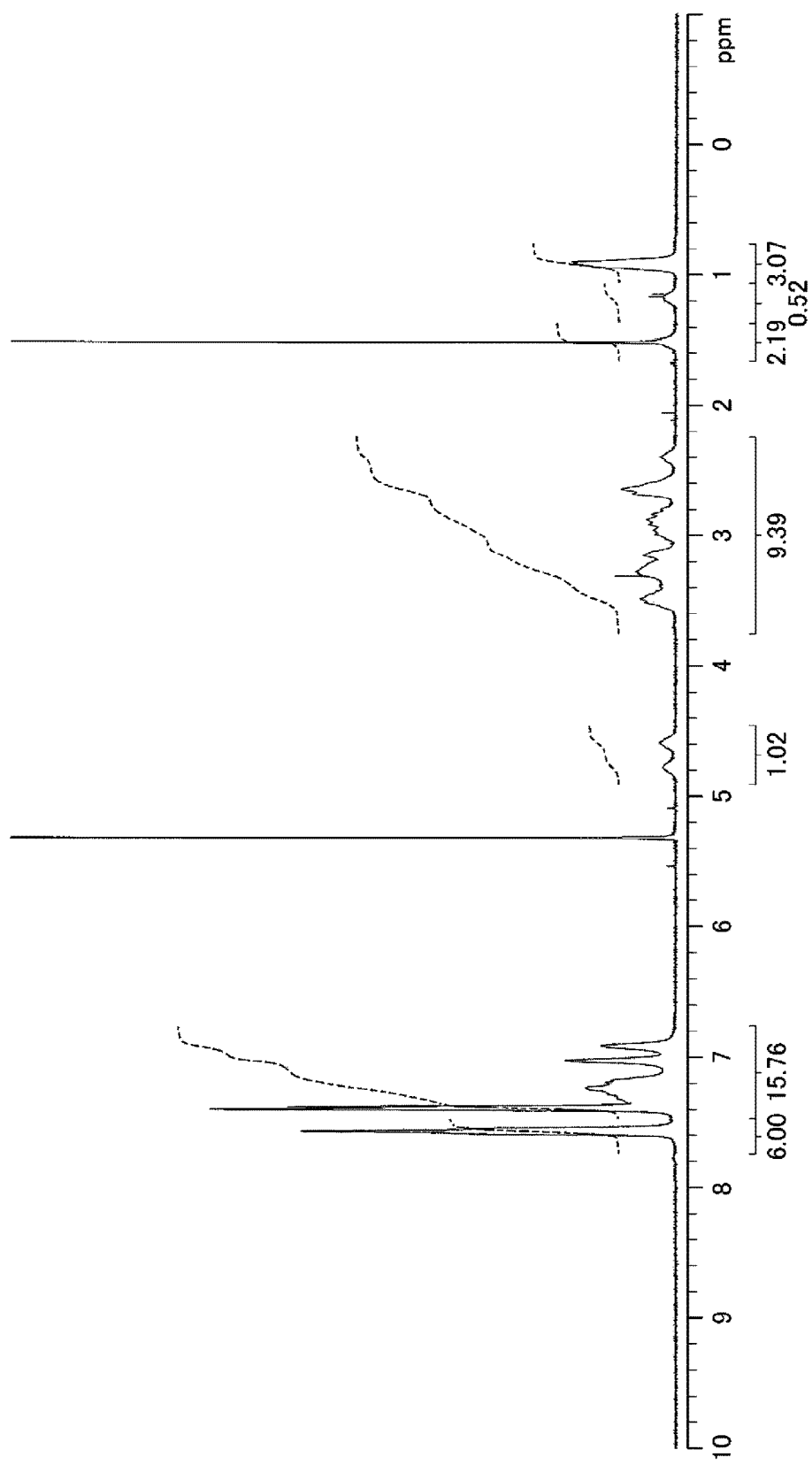
FIG. 12 is a $^1$H NMR chart of dichloro[tris(4-trifluoromethylphenyl)phosphine]{2-diphenylphosphino-N-[2-(ethylthio)ethyl]ethylamine}ruthenium(II) ($8^S$-12) (Example 22).

$^1$H NMR (400 MHz, CD$_2$Cl$_2$): See FIG. 12.
$^{31}$P NMR (161 MHz, CD$_2$Cl$_2$): δ=48.5-45.6 (m, 2P).
$^{19}$F NMR (376 MHz, CD$_2$Cl$_2$): δ=64.82 (s, 9F).

HRMS: M$^+$; Meas. m/z=920.0698, Pred. m/z=920.0633, M=C39H36NF9P2SCl2Ru.

(Example 23) Synthesis of Dichloro[tris(2-furyl)phosphine]{2-diphenylphosphino-N-[2-(ethylthio)ethyl]ethylamine}ruthenium(II) (Structural Compositional Formula ($8^S$-13)) (Eq. 29)

(Example 24) Synthesis of Dichloro{4-ethyl-2,6,7-trioxa-1-phosphabicyclo[2,2,2]octane}{2-diphenylphosphino-N-[2-(ethylthio)ethyl]ethylamine}ruthenium(II) (Structural Compositional Formula ($8^S$-14)) (Eq. 30)

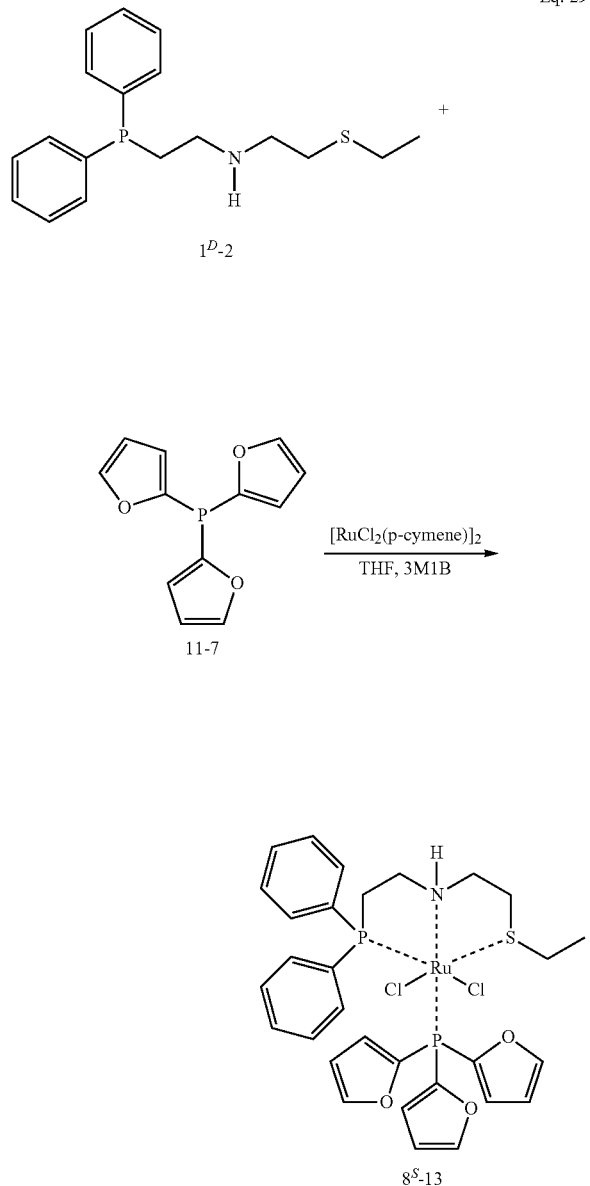

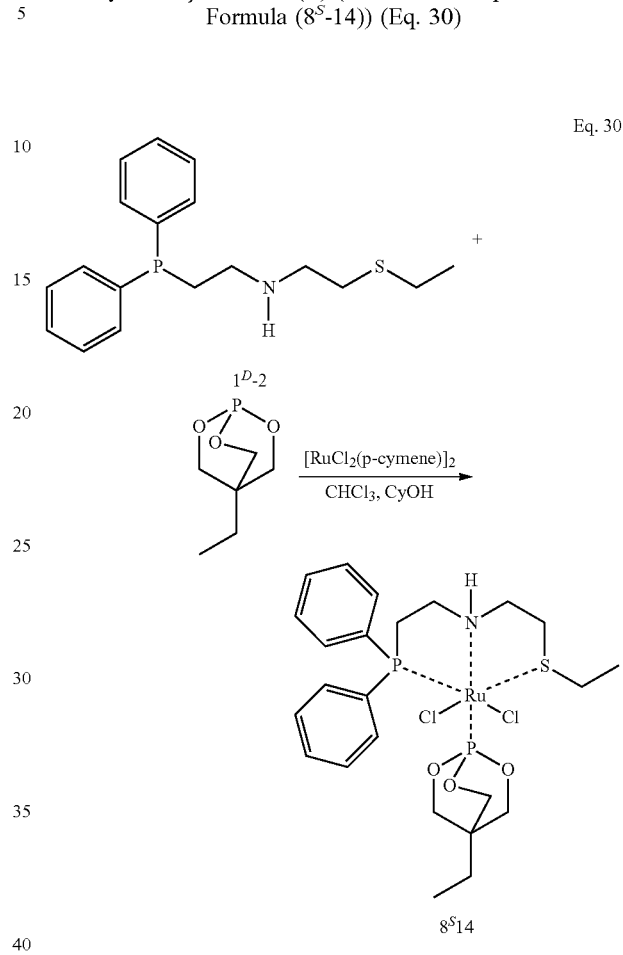

From [RuCl$_2$ (p-cymene)]$_2$ (438 mg, 0.72 mmol, 1.0 equivalents), tris(2-furyl)phosphine (11-7) (366 mg, 1.58 mmol, 2.2 equivalents), anhydrous THF (5 mL), 2-diphenylphosphino-N-[2-(ethylthio)ethyl]ethylamine ($1^D$-2) (500 mg, 1.58 mmol, 2.2 equivalents) obtained in Example 3/Example 4, and 3M1B (10 mL), 750 mg of title compound ($8^S$-13) was obtained as an orange powder in the same manner as in Example 20. Isolated yield: 72.4%.

Figure 13:
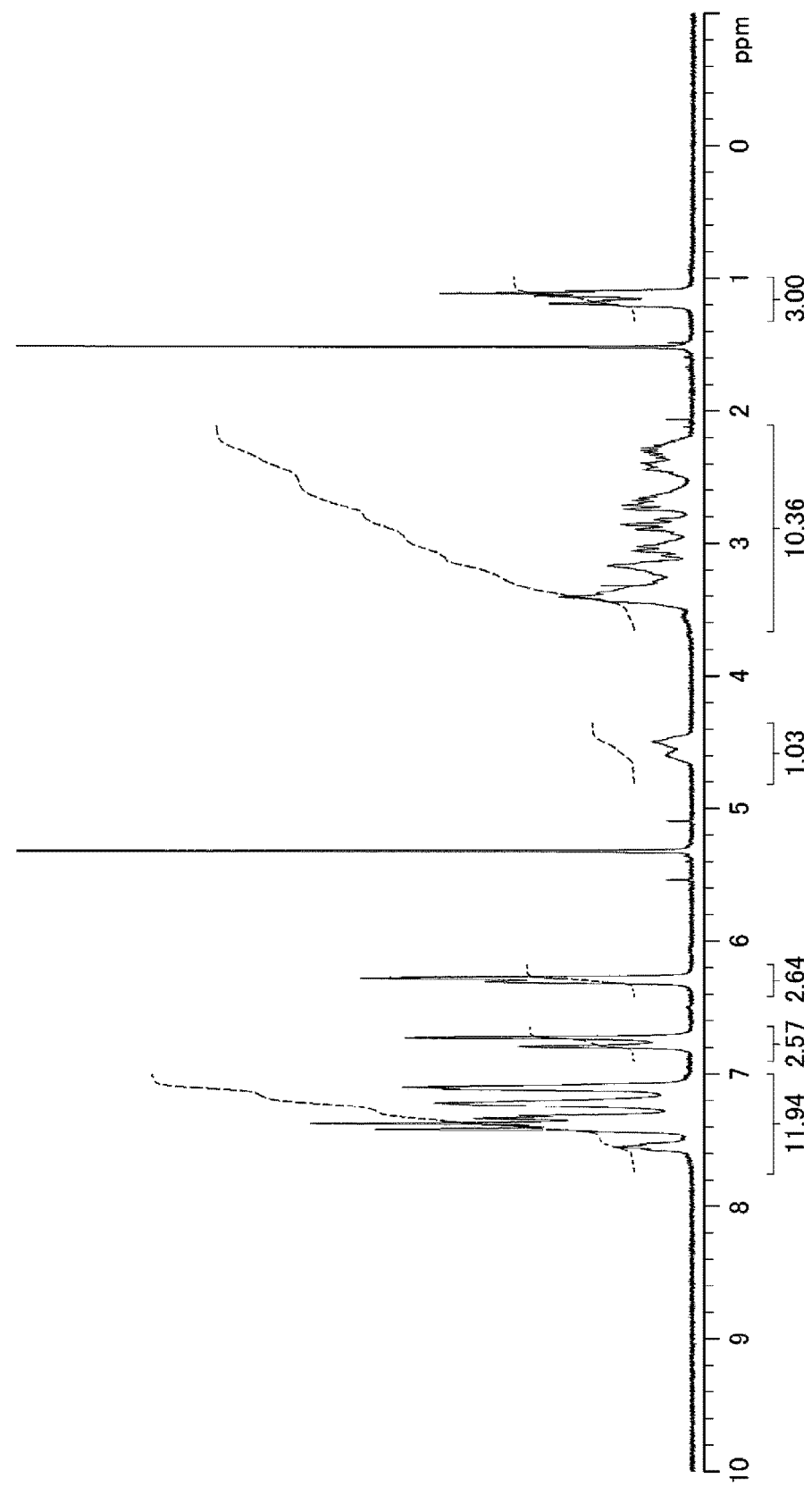
FIG. 13 is a $^1$H NMR chart of dichloro[tris(2-furyl) phosphine]{2-diphenylphosphino-N-[2-(ethylthio)ethyl] ethylamine}ruthenium(II) ($8^S$-13) (Example 23).

$^1$H NMR (400 MHz, CD$_2$Cl$_2$): See FIG. 13.

$^{31}$P NMR (161 MHz, CD$_2$Cl$_2$): δ=52.0-49.6 (m, 1P), 10.3 (d, J=34.0 Hz, 1P).

(Setup and Reaction)

To a 50 mL four-necked round-bottom flask, a magnetic stirrer bar, a Claisen distillation apparatus, a condenser, a thermometer, and a three-way stopcock were attached, and the inside was purged with nitrogen. Then, [RuCl$_2$(p-cymene)]$_2$ (438 mg, 0.72 mmol, 1.0 equivalents), 4-ethyl-2,6,7-trioxa-1-phosphabicyclo[2,2,2]octane (256 mg, 1.58 mmol, 2.2 equivalents), and chloroform (CHCl$_3$) (5 mL) were introduced sequentially, and the obtained deep red solution was stirred at room temperature for 5 minutes. Subsequently, 2-diphenylphosphino-N-[2-(ethylthio)ethyl]ethylamine ($1^D$-2) (500 mg, 1.58 mmol, 2.2 equivalents) obtained in Example 3/Example 4 and cyclohexanol (CyOH) (10 mL) were added, and CHCl$_3$ was removed by distillation at normal pressure using the Claisen distillation apparatus, followed by stirring for 1 hour under reflux in CyOH.

(Post Treatment, Isolation, and Purification)

The reaction liquid was cooled to 5° C., and MeOH (20 mL) was added to the obtained reddish orange suspension, followed by filtration by suction. The crystals obtained by filtration were washed with MeOH, and dried by heating under reduced pressure to obtain 273 mg of title compound ($8^S$-14) as a yellowish orange powder. Isolated yield: 29.3%.

Figure 14:
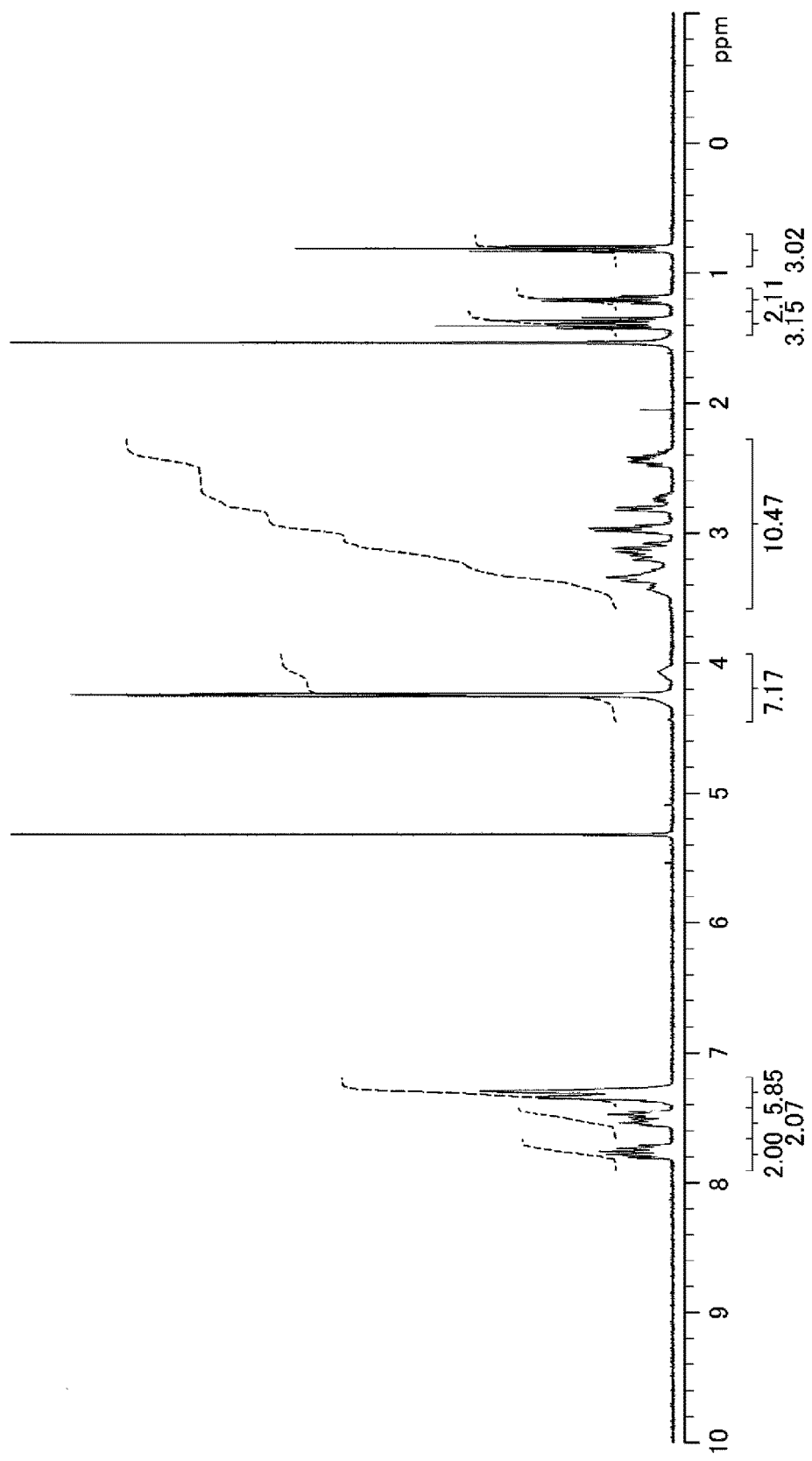
FIG. 14 is a $^1$H NMR chart of dichloro{4-ethyl-2,6,7-trioxa-1-phosphabicyclo[2,2,2]octane}{2-diphenylphosphino-N-[2-(ethylthio)ethyl]ethylamine}ruthenium(II) ($8^S$-14) (Example 24).

$^1$H NMR (400 MHz, CD$_2$Cl$_2$): See FIG. 14.

$^{31}$P NMR (161 MHz, CD$_2$Cl$_2$): δ=135.1-131.8 (m, 1P), 59.7-56.7 (m, 1P).

HRMS: M$^+$; Meas. m/z=651.0217, Pred. m/z=651.0228, M=C24H35NO3P2SC12Ru.

(Example 25) Synthesis of Carbonylchlorohydride{2-diphenylphosphino-N-[2-(methylthio) ethyl] ethylamine}ruthenium(II) (Structural Compositional Formula (8$^S$-15)) (Eq. 31)

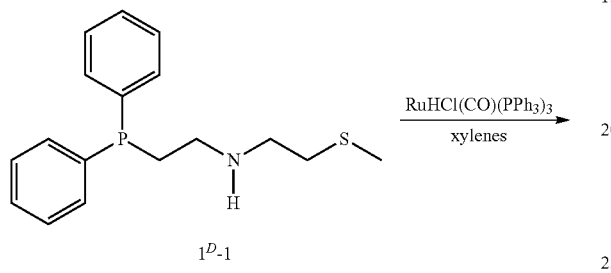

Eq. 31

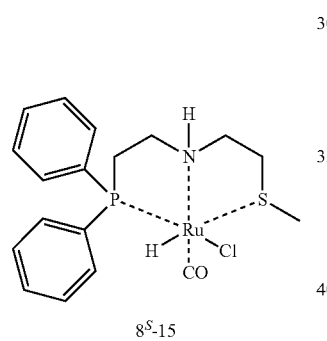

8$^S$-15

(Example 26) Synthesis of Hydride (tetrahydroborate) (triphenylphosphine) {2-diphenylphosphino-N-[2-(ethylthio)ethyl]ethylamine}ruthenium(II) (Structural Compositional Formula (8$^S$-16)) (Eq. 32)

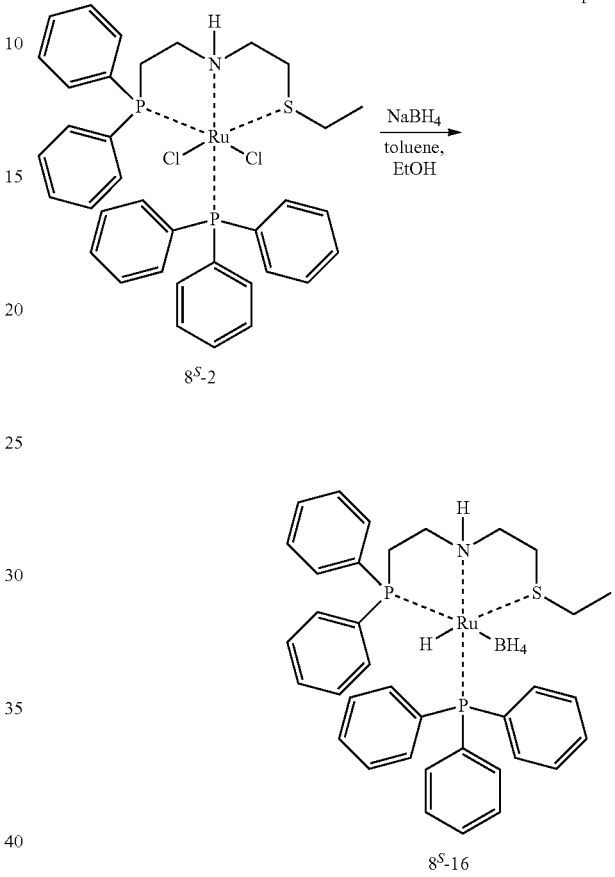

Eq. 32

(Setup and Reaction)

To a 50 mL four-necked round-bottom flask, a magnetic stirrer bar, a condenser, a thermometer, and a three-way stopcock were attached, and the inside was purged with nitrogen. Then, 2-diphenylphosphino-N-[2-(methylthio) ethyl]ethylamine (1$^D$-1) (1.0 g, 3.30 mmol, 2.2 equivalents) obtained in Example 1/Example 2, xylene (isomer mixture, 15 mL), and carbonylchlorohydridetris(triphenylphosphine) ruthenium(II) (RuHCl(CO) (PPh$_3$)$_3$) (2.86 g, 3.00 mmol, 1.0 equivalents) were introduced sequentially, and the obtained brown suspension was stirred for 30 minutes under reflux in xylene.

(Post Treatment, Isolation, and Purification)

The orange suspension obtained after the reaction was cooled to 5° C. and filtered by suction. Then, the crystals obtained by filtration were washed with toluene, and dried by heating under reduced pressure. Thus, 1.32 g of title compound (8$^S$-15) was obtained as a yellowish orange powder. Isolated yield: 93.8%.

Figure 15:
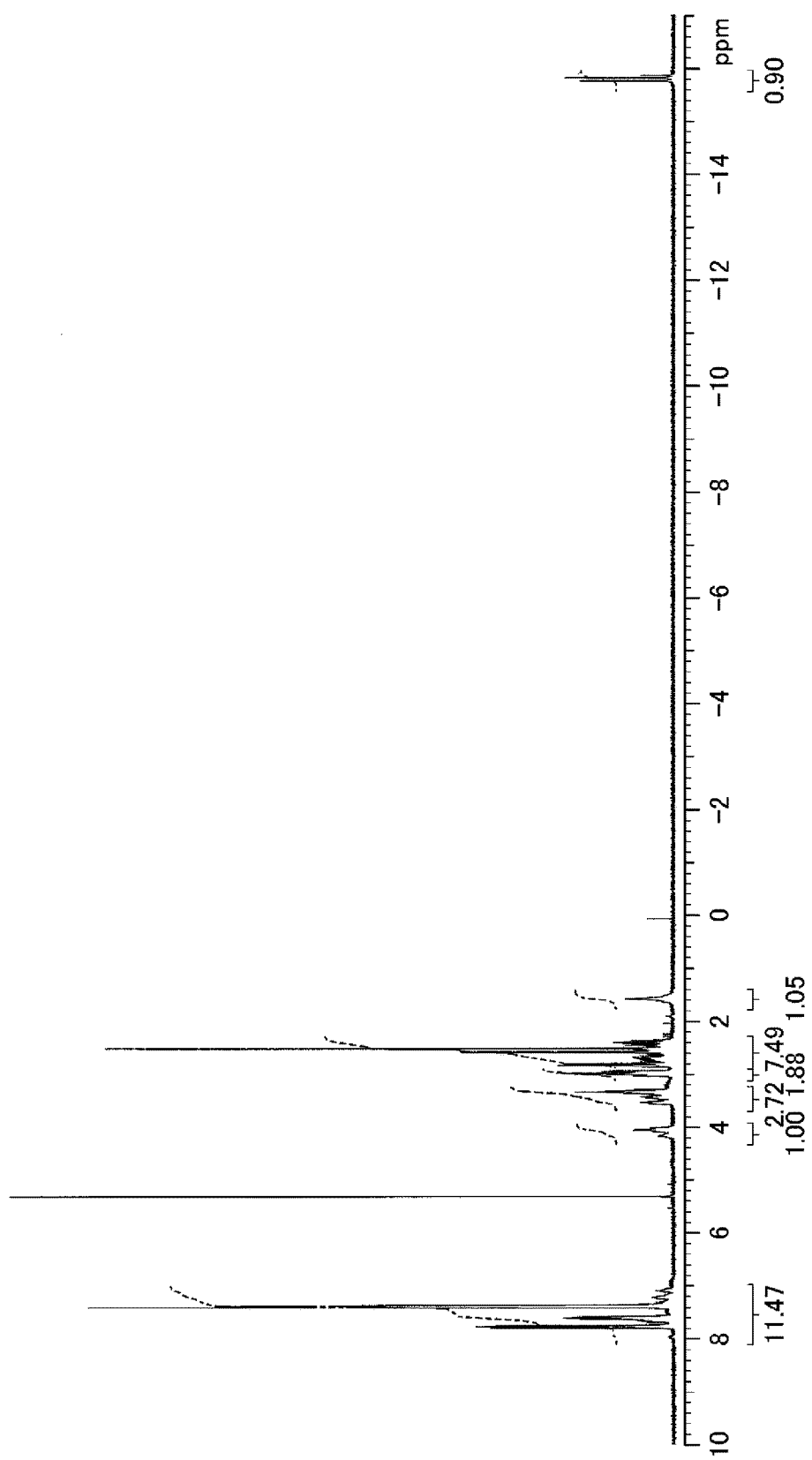
FIG. 15 is a $^1$H NMR chart of carbonylchlorohydride{2-diphenylphosphino-N-[2-(methylthio)ethyl]ethylamine}ruthenium(II) ($8^S$-15) (Example 25).

$^1$H NMR (400 MHz, CD$_2$Cl$_2$): See FIG. 15.

$^{31}$P NMR (161 MHz, CD$_2$Cl$_2$): δ=66.3-64.0 (m, 1P).

(Setup and Reaction)

To a 50 mL four-necked round-bottom flask, a magnetic stirrer bar, a condenser, a thermometer, and a three-way stopcock were attached, and the inside was purged with nitrogen. Then, dichloro(triphenylphosphine){2-diphenylphosphino-N-[2-(ethylthio)ethyl]ethylamine}ruthenium(II) (8$^S$-2) (99.4 mg, 0.132 mmol, 1.0 equivalents) obtained in Example 12, toluene (3 mL), ethanol (EtOH) (3 mL), and sodium tetrahydroborate (NaBH$_4$) (50.0 mg, 1.32 mmol, 10.0 equivalents) were sequentially added, and the obtained orange suspension was stirred at 65° C. for 1 hour.

(Post Treatment, Isolation, and Purification)

The light yellow suspension obtained after the reaction was cooled to room temperature, and filtered by suction. Then, the obtained crystals were washed sequentially with toluene and n-heptane, and then dried under reduced pressure. Thus, 108.0 mg of title compound (8$^S$-16) was obtained as a light yellow powder. Isolated yield: 98.5%, Purity: 83.9% by weight (determined by $^1$H NMR). Note that the major impurity was n-heptane.

Figure 16:
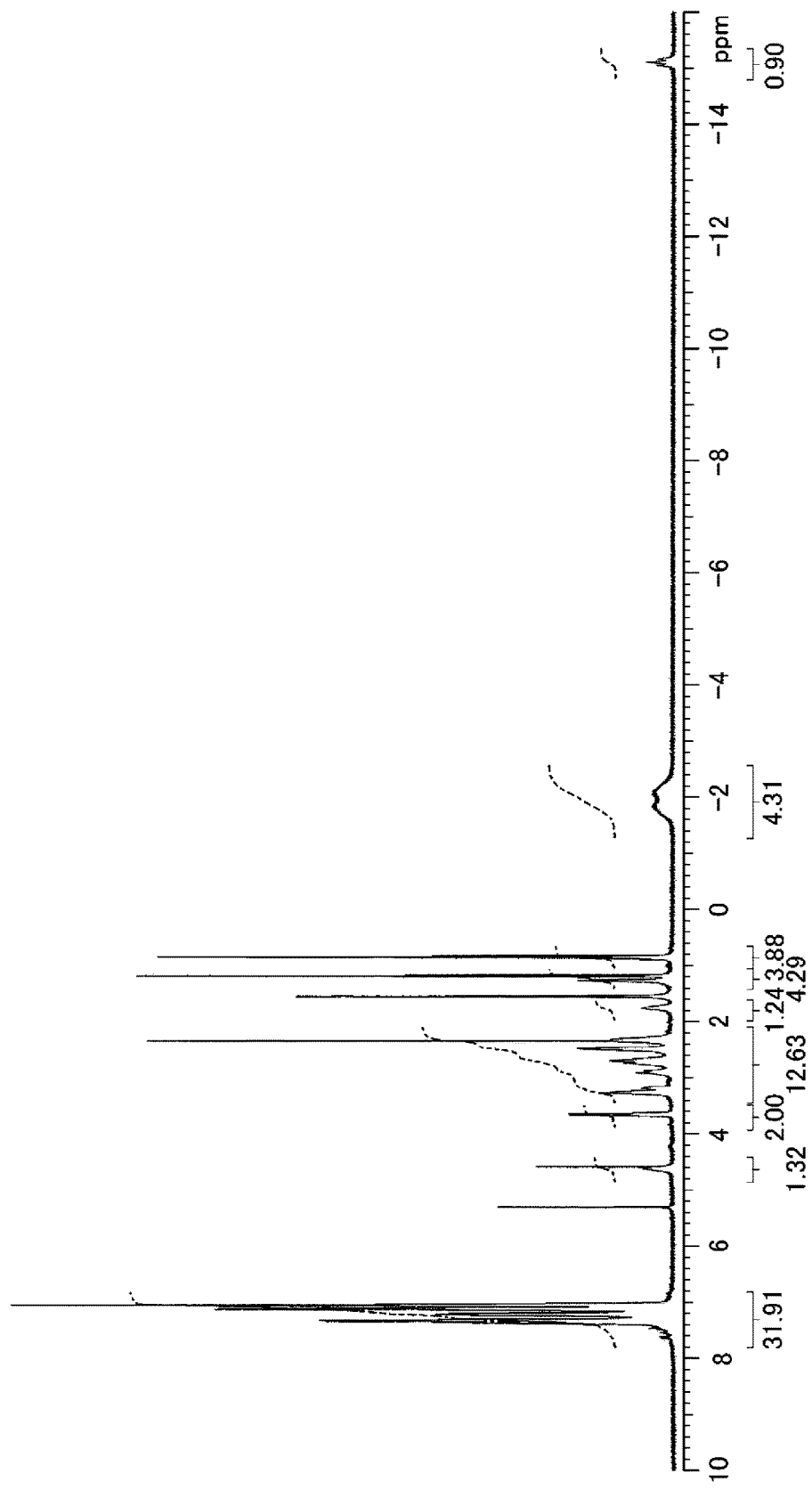
FIG. 16 is a $^1$H NMR chart of hydride(tetrahydroborate) (triphenylphosphine){2-diphenylphosphino-N-[2-(ethylthio)ethyl]ethylamine}ruthenium(II) ($8^S$-16) (Example 26).

$^1$H NMR (400 MHz, CD$_2$Cl$_2$): See FIG. 16.

$^{31}$P NMR (161 MHz, CD$_2$Cl$_2$): δ=68.4-65.0 (m, 2P)

(Example 27) Synthesis of Carbonylhydride(tetrahydroborate){2-diphenylphosphino-N-[2-(methylthio)ethyl]ethylamine}ruthenium(II) (Structural Compositional Formula ($8^S$-17)) (Eq. 33)

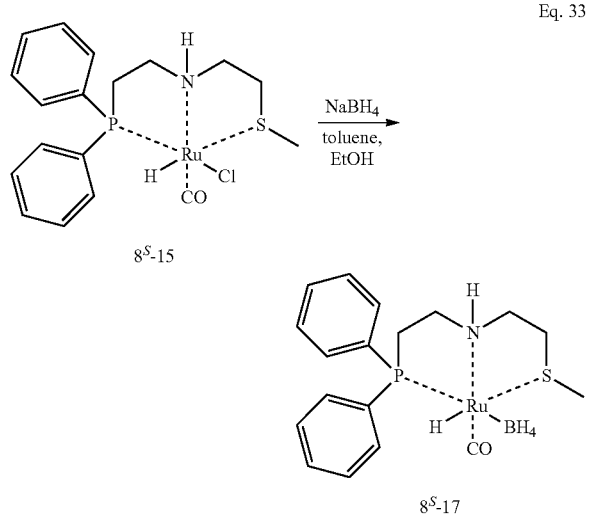

(Setup and Reaction)

To a 50 mL four-necked round-bottom flask, a magnetic stirrer bar, a condenser, a thermometer, and a three-way stopcock were attached, and the inside was purged with nitrogen. Then, carbonylchlorohydride{2-diphenylphosphino-N-[2-(methylthio)ethyl]ethylamine}ruthenium(II) ($8^S$-15) (61.9 mg, 0.132 mmol, 1.0 equivalents) obtained in Example 25, toluene (3 mL), EtOH (3 mL), and NaBH$_4$ (50.0 mg, 1.32 mmol, 10.0 equivalents) were added sequentially, and the obtained white suspension was stirred at 65° C. for 3 hours.

(Post Treatment, Isolation, and Purification)

The white suspension obtained after the reaction was concentrated under reduced pressure. Then, water and ethyl acetate were added, and the aqueous layer was separated. Then, the organic layer was concentrated. The obtained residue was recrystallized from toluene/ethyl acetate to obtain 30.1 mg of title compound ($8^S$-17) as a gray powder. Isolated yield: 50.9%.

Figure 17:
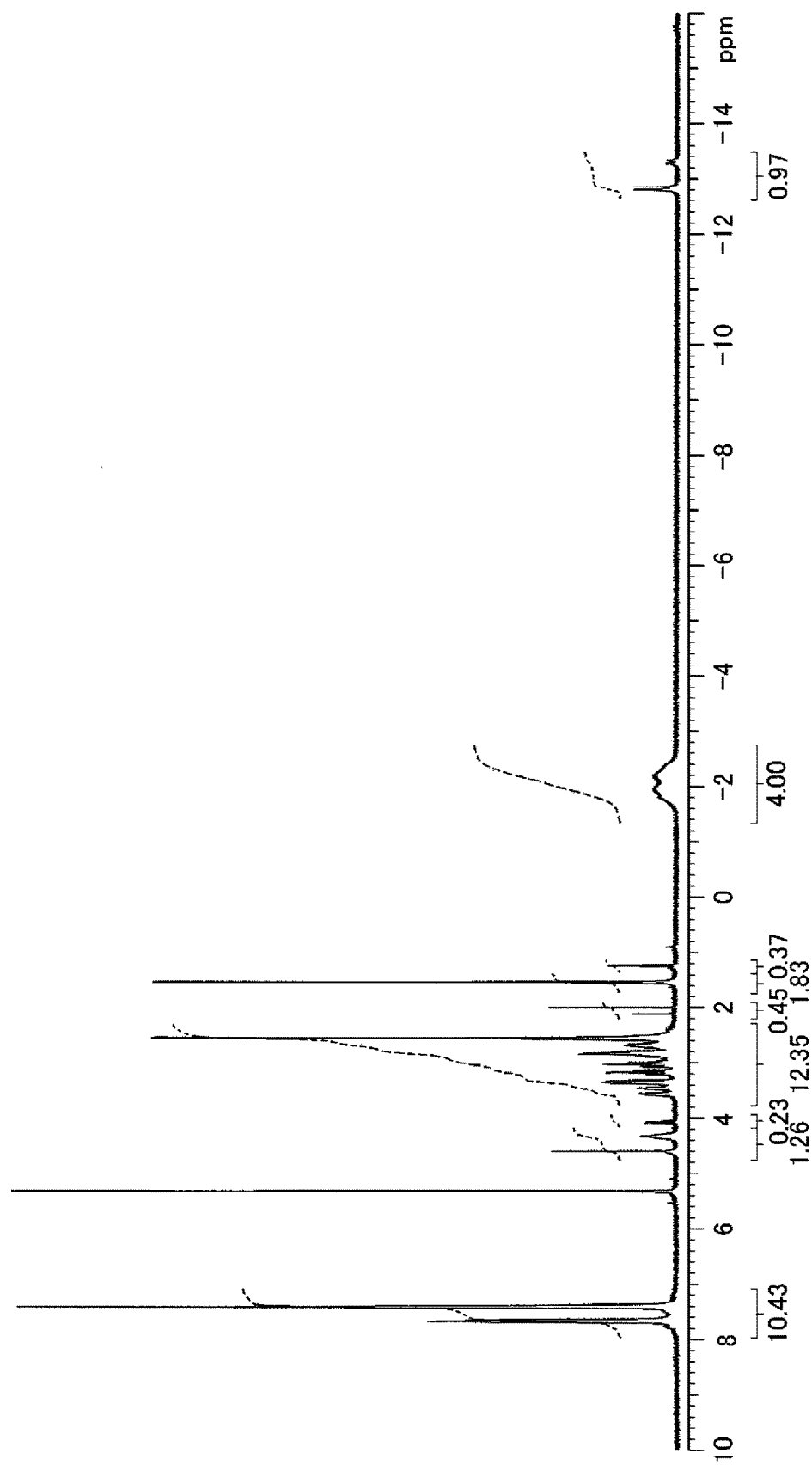
FIG. 17 is a $^1$H NMR chart of carbonylhydride (tetrahydroborate) {2-diphenylphosphino-N-[2-(methylthio)ethyl] ethylamine}ruthenium(II) ($8^S$-17) (Example 27).

$^1$H NMR (400 MHz, CD$_2$Cl$_2$): See FIG. 17.
$^{31}$P NMR (161 MHz, CD$_2$Cl$_2$): δ=67.6 (s, 1P).

(Example 28) Synthesis of Dichloro{2-diphenylphosphino-N-[2-(ethylthio)ethyl]ethylamine}ruthenium(II) Dimer (Structural Compositional Formula ($8^U$-1)) (Eq. 34)

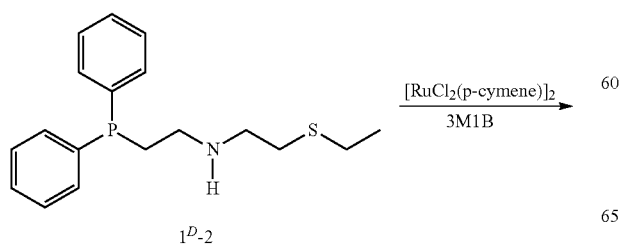

-continued

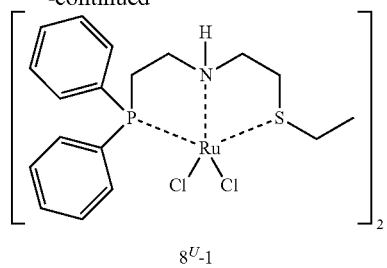

(Setup and Reaction)

To a 50 mL four-necked round-bottom flask, a magnetic stirrer bar, a condenser, a thermometer, and a three-way stopcock were attached, and the inside was purged with nitrogen. Then, 2-diphenylphosphino-N-[2-(ethylthio)ethyl]ethylamine ($1^D$-2) (1.0 g, 3.15 mmol, 2.1 equivalents) obtained in Example 3/Example 4, 3M1B (10 mL), and [RuCl$_2$(p-cymene)]2 (918 mg, 1.50 mmol, 1.0 equivalents) were introduced sequentially, and the obtained dark red suspension was stirred for 3 hours under reflux in 3M1B.

(Post treatment and Purification)

The orange suspension obtained after the reaction was cooled to room temperature and filtered by suction. Then, the crystals obtained by filtration were washed with MeOH, and dried by heating under reduced pressure. Thus, 1.24 g of title compound ($8^U$-1) was obtained as an orange powder. Isolated yield: 84.5%.

Figure 18:
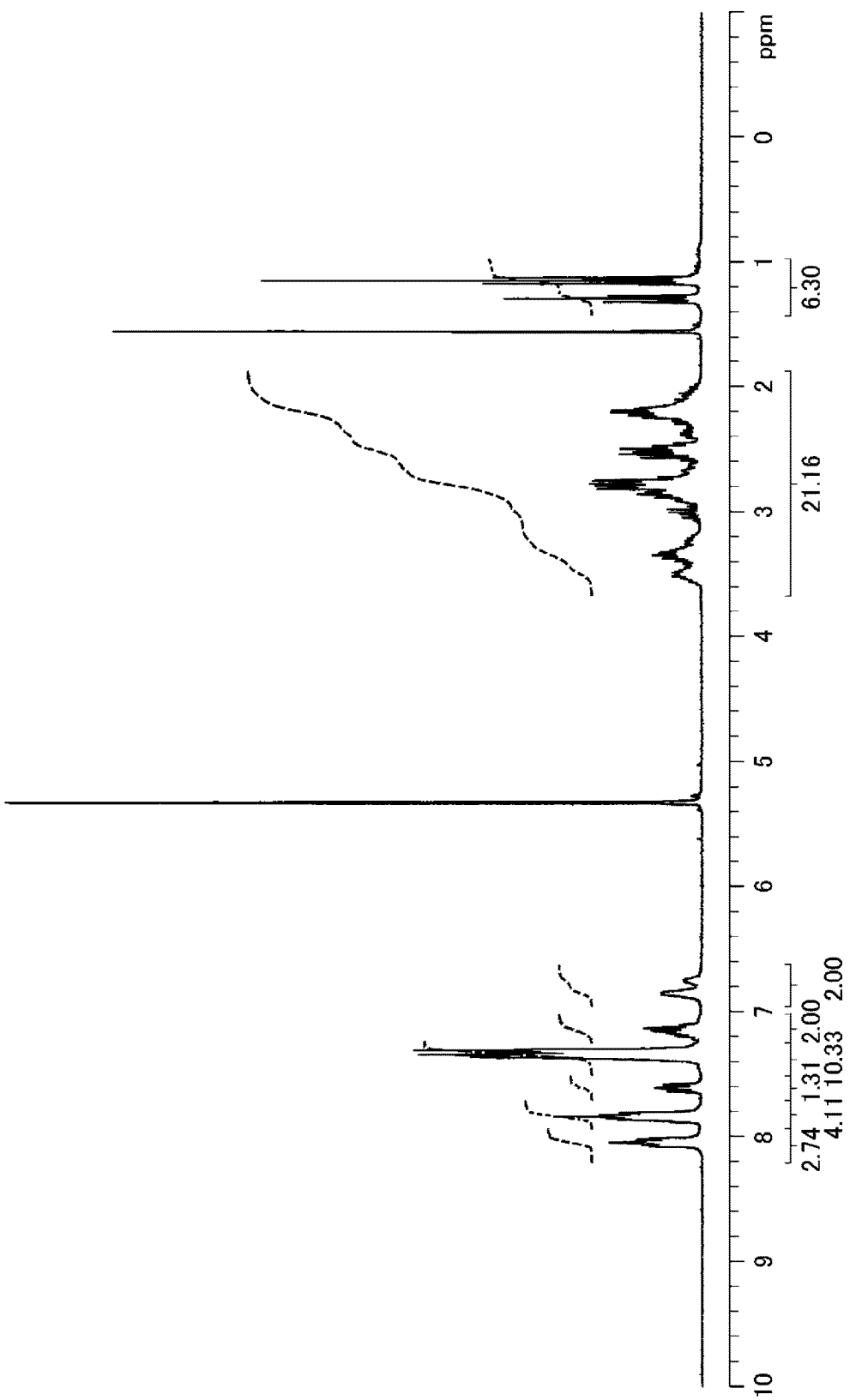
FIG. 18 is a $^1$H NMR chart of dichloro{2-diphenylphosphino-N-[2-(ethylthio)ethyl]ethylamine}ruthenium(II) dimer ($8^U$-1) (Example 28).

$^1$H NMR (300 MHz, CD$_2$Cl$_2$): See FIG. 18.
$^{31}$P NMR (121 MHz, CD$_2$Cl$_2$): δ=73.7 (s, 2P).
HRMS: [M-Cl]$^+$; Meas. m/z=942.9864, Pred. m/z=942.9884, M-Cl=C36H48N2P2S2Cl3Ru2.

(Example 29) Synthesis of Dichloro{2-diphenylphosphino-N-[2-(phenylthio)ethyl]ethylamine}ruthenium(II) Dimer (Structural Compositional Formula ($8^U$-2)) (Eq. 35)

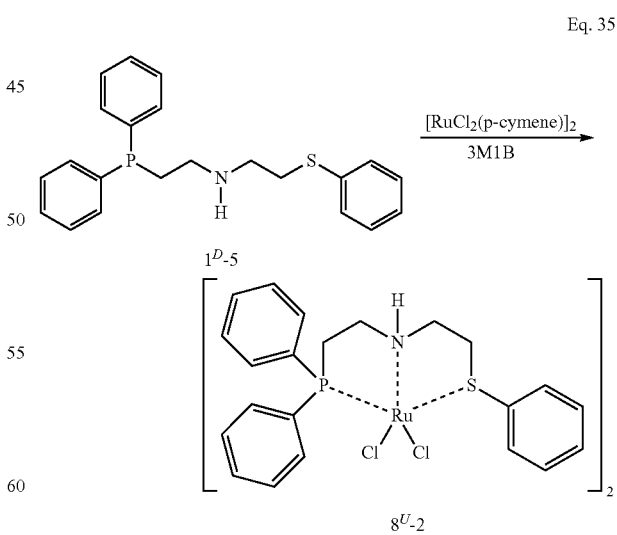

From 2-diphenylphosphino-N-[2-(phenylthio)ethyl]ethylamine ($1^D$-5) (1.0 g, 2.74 mmol, 2.1 equivalents) obtained in Example 8, 3M1B (10 mL), and [RuCl$_2$ (p-cymene)]$_2$ (798 mg, 1.30 mmol, 1.0 equivalents), 1.29 g of title compound ($8^U$-2) was obtained as an orange powder in the same manner as in Example 28. Isolated yield: 92.3%.

$^1$H NMR (300 MHz, CD$_2$Cl$_2$): Unmeasurable because of low solubility.

$^{31}$P NMR (121 MHz, CD$_2$Cl$_2$): Unmeasurable because of low solubility.

HRMS: [M-Cl]; Meas. m/z=1038.986, Pred. m/z=1038.989, M-Cl=C44H48N2P2S2Cl3Ru2.

(Example 30) Synthesis of Dichloro{2-diphenylphosphino-N-[2-(p-tolylthio)ethyl]ethylamine}ruthenium(II) Dimer (Structural Compositional Formula ($8^U$-3)) (Eq. 36)

Eq. 36

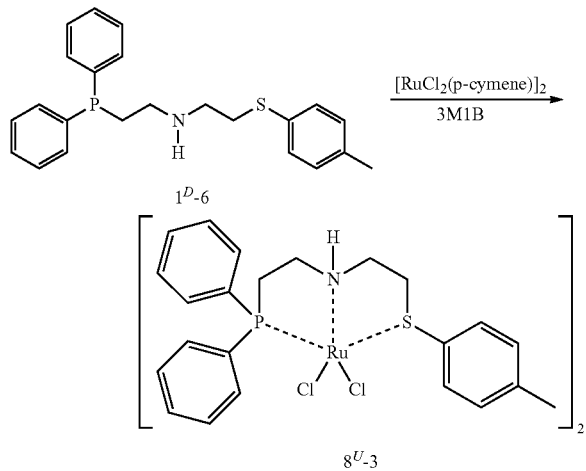

From 2-diphenylphosphino-N-[2-(p-tolylthio)ethyl]ethylamine ($1^D$-6) (2.0 g, 5.27 mmol, 2.1 equivalents) obtained in Example 9, 3M1B (15 mL), and [RuCl$_2$(p-cymene)]$_2$ (1.54 g, 2.51 mmol, 1.0 equivalents), 2.46 g of title compound ($8^U$-3) was obtained as an orange powder in the same manner as in Example 28. Isolated yield: 88.9%.

$^1$H NMR (300 MHz, CD$_2$Cl$_2$): Unmeasurable because of low solubility.

$^{31}$P NMR (121 MHz, CD$_2$Cl$_2$): Unmeasurable because of low solubility.

HRMS: [M-Cl]$^+$; Meas. m/z=1067.021, Pred. m/z=1067.020, M-Cl=C46H52N2P2S2Cl3Ru2.

(Example 31) Synthesis of [Chlorobis(4-methoxyphenylisocyanide) {2-diphenylphosphino-N-[2-(ethylthio)ethyl]ethylamine}ruthenium(II)] Chloride (Structural Compositional Formula ($8^R$-1)) (Eq. 37)

Eq. 37

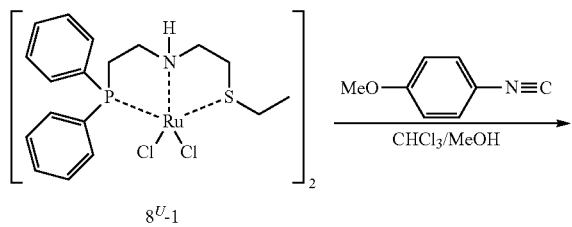

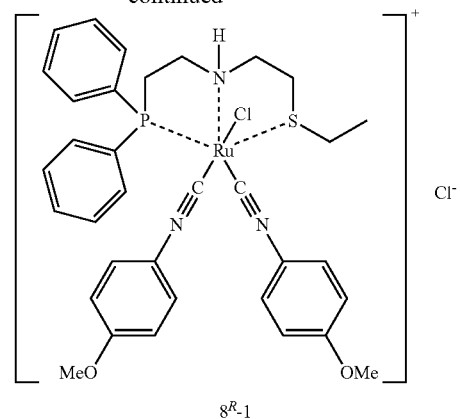

(Setup and Reaction)

To a 50 mL four-necked round-bottom flask, a magnetic stirrer bar, a condenser, a thermometer, and a three-way stopcock were attached, and the inside was purged with nitrogen. Then, dichloro{2-diphenylphosphino-N-[2-(ethylethyl)ethylamine}ruthenium(II) dimer ($8^U$-1) (160.1 mg, 0.163 mmol, 1.0 equivalents) obtained in Example 28, 4-methoxyphenyl isocyanide (87.1 mg, 0.650 mmol, 4.0 equivalents), CHCl$_3$ (20 mL), and MeOH (2 mL) were introduced sequentially, and the obtained green suspension was stirred at 60° C. for 4 hours.

(Post treatment and Purification)

The reaction liquid was concentrated under reduced pressure, and the obtained green residue was washed sequentially with MeOH, toluene, and n-heptane, and dried by heating under reduced pressure. Thus, 63.2 mg of title compound ($8^R$-1) was obtained as a light yellow powder. Isolated yield: 25.7%.

Figure 19:
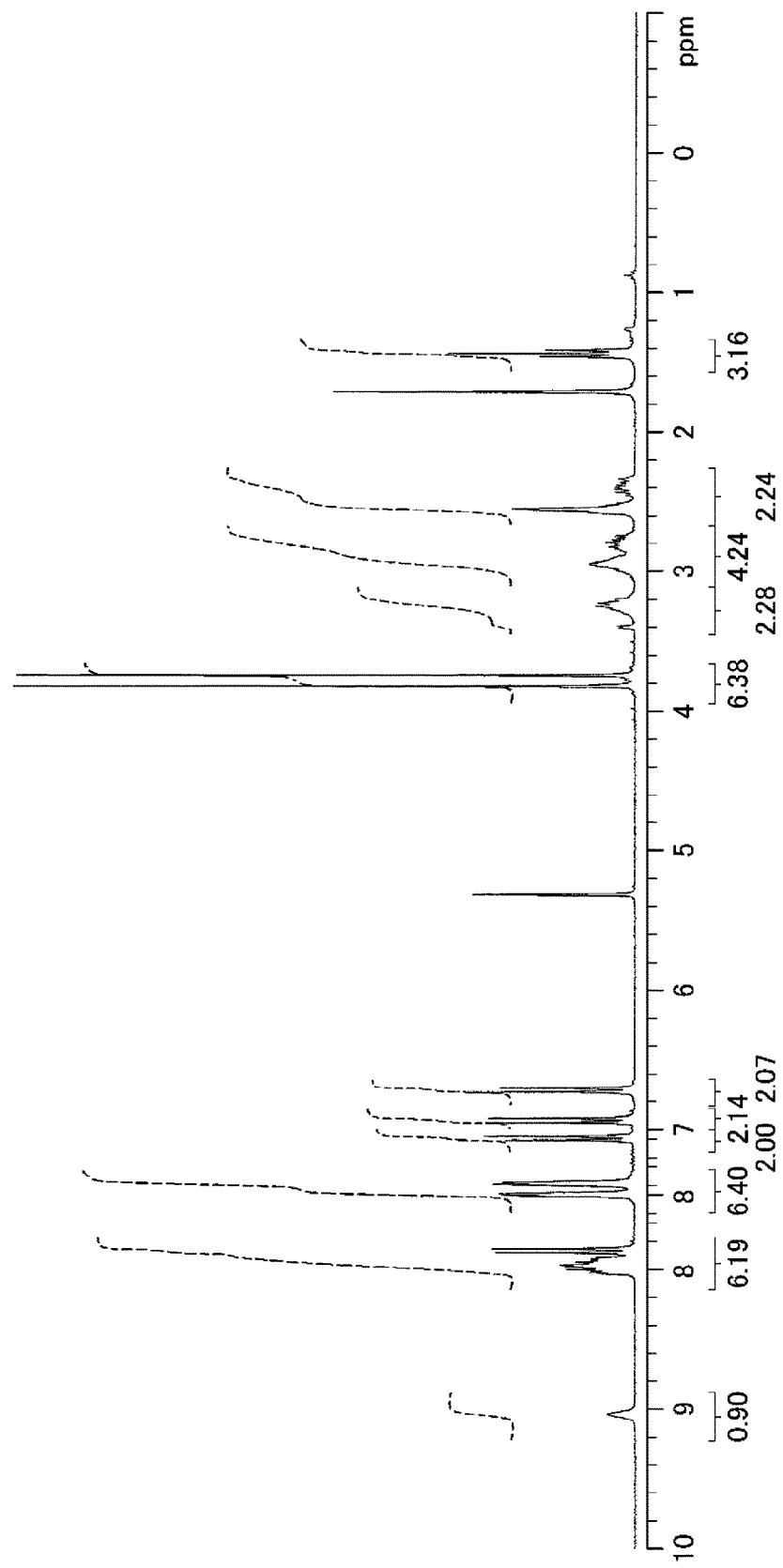
FIG. 19 is a $^1$H NMR chart of [chlorobis(4-methoxyphenylisocyanide){2-diphenylphosphino-N-[2-(ethylthio)ethyl] ethylamine}ruthenium(II)]chloride ($8^R$-1) (Example 31).

$^1$H NMR (300 MHz, CD$_2$Cl$_2$): See FIG. 19.

$^{31}$P NMR (121 MHz, CD$_2$Cl$_2$): δ=34.0 (s, 1P).

HRMS: [M-Cl]$^+$; Meas. m/z=720.1146, Pred. m/z=720.1154, M-Cl=C34H38N3O2PSClRu.

(Example 32) Synthesis of Benzyl Alcohol based on Hydrogenation Reaction of Methyl Benzoate Catalyzed by Dichloro(triphenylphosphine){2-diphenylphosphino-N-[2-(ethylthio)ethyl]ethylamine}ruthenium(II) ($8^S$-2) (Eq. 38)

Eq. 38

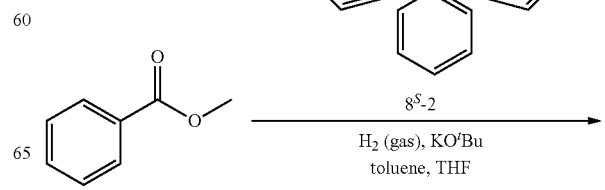

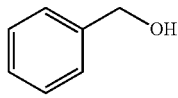

(Setup and Reaction)

In a 100 mL stainless steel autoclave apparatus, dichloro(triphenylphosphine){2-diphenylphosphino-N-[2-(ethylthio)ethyl]ethylamine}ruthenium(II) ($8^S$-2) (purity: 94.2% by weight, 2.0 mg, 0.1 mol %) obtained in Example 12 was placed, and the inside was purged with nitrogen. Then, toluene (2.0 mL), a solution of potassium tert-butoxide (KO$^t$Bu) in THF (concentration: 1.0 mol/L, 250 μL, 0.25 mmol, 0.1 equivalents), and methyl benzoate (312 μL, 2.50 mmol, 1.0 equivalents) were sequentially introduced, and then the inside was purged with hydrogen (H$_2$) and further pressurized with H$_2$ gas to 1 MPa, followed by stirring at 80° C. for 6 hours. Thus, the target benzyl alcohol was obtained. Conversion: 100%, Selectivity: 100% (determined by GC analysis).

GC retention times; methyl benzoate: 16.77 minutes, benzyl alcohol: 22.30 minutes.

(Comparative Example 1) Synthesis of Benzyl Alcohol based on Hydrogenation Reaction of Methyl Benzoate catalyzed by Dichloro(triphenylphosphine) {N,N-bis[2-(diphenylphosphino)ethyl]amine}ruthenium(II) (14-1) (Eq. 39)

Eq. 39

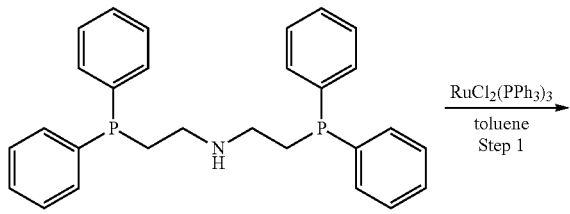

14-1

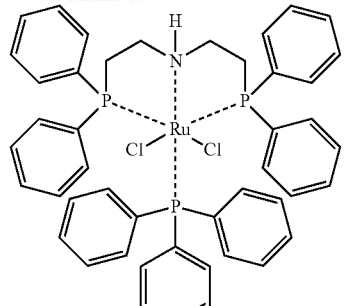

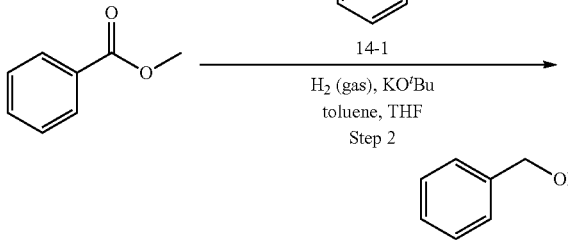

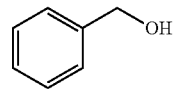

Step 1: Synthesis of Dichloro(triphenylphosphine) {N,N-bis[2-(diphenylphosphino)ethyl] amine}ruthenium(II)

(Reaction and Setup)

To a 50 mL four-necked round-bottom flask, a magnetic stirrer bar, a condenser, a thermometer, and a three-way stopcock were attached, and the inside was purged with nitrogen. Then, RuCl$_2$(PPh$_3$)$_3$ (2.00 g, 2.09 mmol, 1.0 equivalents), anhydrous toluene (20 mL), and N,N-bis[2-(diphenylphosphino)ethyl]amine (1.03 g, 2.34 mmol, 1.1 equivalents), which was already known, were introduced sequentially, and the obtained dark purple suspension was stirred for 1 hour under reflux in toluene.

(Post Treatment, Isolation, and Purification)

The ocher suspension obtained after the reaction was cooled to 5° C., and then filtered by suction. The crystals obtained by filtration were washed sequentially with toluene and n-hexane, and dried by heating under reduced pressure. Thus, 2.06 g of title compound (14-1) was obtained as a yellowish orange powder. Isolated yield: 91.9%, Purity: 98.9% by weight (determined by $^1$H NMR analysis). Note that the major impurity was toluene.

$^1$H NMR (300 MHz, CD$_2$Cl$_2$): δ=7.36-7.29 (m, 18H), 7.16-7.00 (m, 11H), 6.84-6.75 (m, 6H), 4.76-4.60 (m, 1H), 3.50-3.06 (m, 4H), 2.82-2.48 (M, 4H).

$^{31}$P NMR (121 MHz, CD$_2$Cl$_2$): δ=41.4 (d, J=29.5 Hz, 1P), 29.6 (d, J=28.1 Hz, 2P).

Step 2: Synthesis of Benzyl Alcohol

Benzyl alcohol was synthesized by a hydrogenation reaction of methyl benzoate in the same manner as in Example 32, except that dichloro(triphenylphosphine){N,N-bis[2-(diphenylphosphino)ethyl]amine}ruthenium(II) (14-1) (purity: 98.9% by weight, 2.2 mg, 0.1 mol %) obtained in Step 1 was used as the catalyst. Conversion: 7.9%, Selectivity: 79.8% (determined by GC analysis).

(Comparative Example 2) Synthesis of Benzyl Alcohol based on Hydrogenation Reaction of Methyl Benzoate catalyzed by Dichloro(triphenylphosphine){N,N-bis[2-(ethylthio)ethyl]amine}ruthenium(II) (14-2) (Eq. 40)

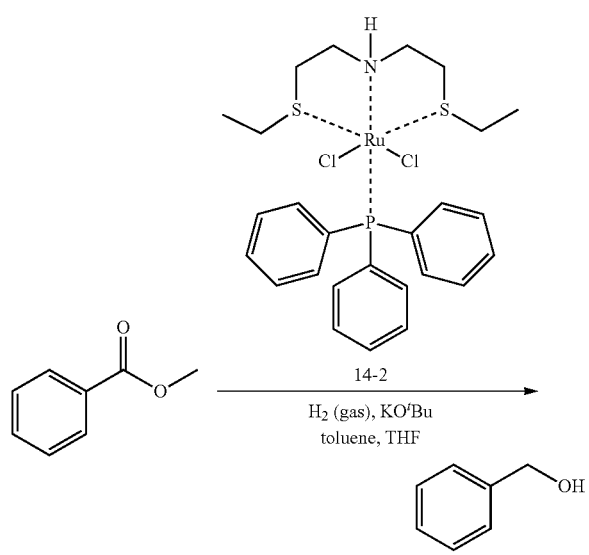

Eq. 40

Benzyl alcohol was synthesized by a hydrogenation reaction of methyl benzoate in exactly the same manner as in Example 32, except that commercially available dichloro(triphenylphosphine){N,N-bis[2-(ethylthio)ethyl]amine}ruthenium(II) (14-2) (1.6 mg, 0.1 mol %) was used as the catalyst. Conversion: 100%, Selectivity: 93.4% (determined by GC analysis).

(Example 33) Synthesis of 1,2-Propanediol based on Hydrogenation Reaction of Methyl Lactate catalyzed by Dichloro(triphenylphosphine) {2-diphenylphosphino-N-[2-(ethylthio)ethyl]ethylamine}ruthenium(II) ($8^S$-2) (Eq. 41)

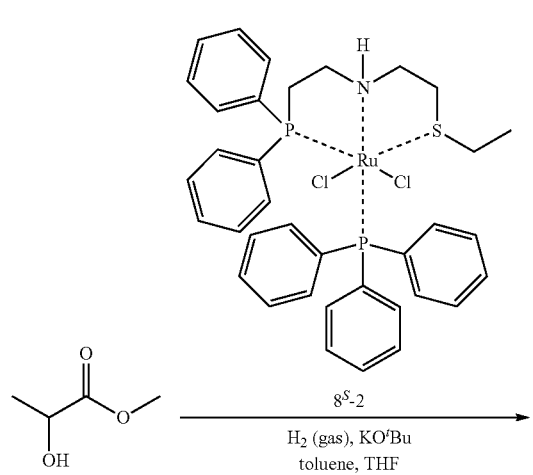

Eq. 41

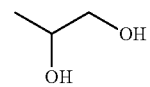

(Setup and Reaction)

In a 100 mL stainless steel autoclave apparatus, dichloro(triphenylphosphine){2-diphenylphosphino-N-[2-(ethylthio)ethyl]ethylamine}ruthenium(II) ($8^S$-2) (purity: 94.2% by weight, 2.0 mg, 0.1 mol %) obtained in Example 12 was placed, and the inside was purged with nitrogen. Then, toluene (2.0 mL), a solution of KO$^t$Bu in THF (concentration: 1.0 mol/L, 250 µL, 0.25 mmol, 0.1 equivalents), and methyl lactate (238 µL, 2.50 mmol, 1.0 equivalents) were sequentially introduced, and then the inside was purged with $H_2$ and further pressurized to 1 MPa with $H_2$ gas, followed by stirring at 80° C. for 6 hours. Thus, the target 1,2-propanediol was obtained. Conversion: 100%, Selectivity: 100% (determined by GC analysis). GC retention times; methyl lactate: 9.08 minutes, 1,2-propanediol: 15.84 minutes.

(Comparative Example 3) Synthesis of 1,2-Propanediol based on Hydrogenation Reaction of Methyl Lactate catalyzed by Dichloro(triphenylphosphine){N,N-bis[2-(diphenylphosphino)ethyl]amine}ruthenium(II) (14-1) (Eq. 42)

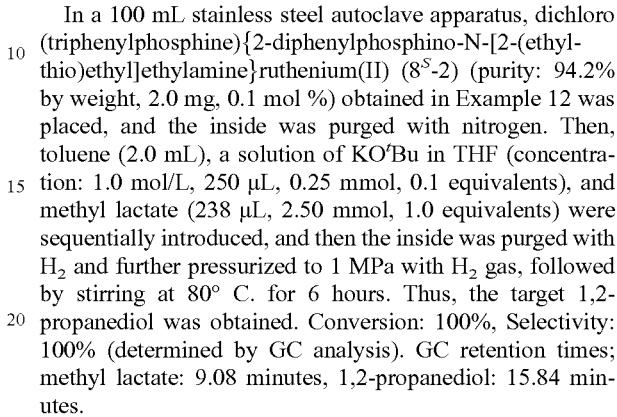

Eq. 42

1,2-Propanediol was synthesized by a hydrogenation reaction of methyl lactate in the same manner as in Example 33, except that dichloro(triphenylphosphine) {N,N-bis[2-(diphenylphosphino)ethyl]amine}ruthenium(II) (14-1) (purity: 98.9% by weight, 2.2 mg, 0.1 mol %) obtained in Step 1 of Comparative Example 1 was used as the catalyst. Conversion: 18.6%, Selectivity: 64.3% (determined by GC analysis).

(Comparative Example 4) Synthesis of 1,2-Propanediol based on Hydrogenation Reaction of Methyl Lactate catalyzed by Dichloro(triphenylphosphine){N,N-bis[2-(ethylthio)ethyl]amine}ruthenium(II) (14-2) (Eq. 43)

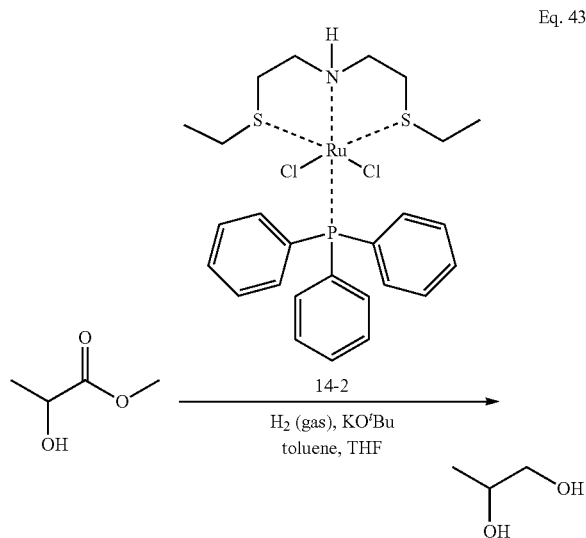

1,2-Propanediol was synthesized by a hydrogenation reaction of methyl lactate in exactly the same manner as in Example 33, except that commercially available dichloro(triphenylphosphine){N,N-bis[2-(ethylthio)ethyl]amine}ruthenium(II) (14-2) (1.6 mg, 0.1 mol %) was used as the catalyst. Conversion: 17.9%, Selectivity: 59.4% (determined by GC analysis).

The results of Example 32, Example 33, and Comparative Examples 1 to 4 are summarized in Table 1 below.

TABLE 1

| Example/Comparative Example | Catalyst | Product | Conversion | Selectivity |
| --- | --- | --- | --- | --- |
| Example 32 | $8^s$-2 | Benzyl alcohol | 100% | 100% |
| Comp. Ex. 1 | 14-1 | Benzyl alcohol | 7.9% | 79.8% |
| Comp. Ex. 2 | 14-2 | Benzyl alcohol | 100% | 93.4% |
| Example 33 | $8^s$-2 | 1,2-Propanediol | 100% | 100% |
| Comp. Ex. 3 | 14-1 | 1,2-Propanediol | 18.6% | 64.3% |
| Comp. Ex. 4 | 14-2 | 1,2-Propanediol | 17.9% | 59.4% |

As can be seen from these results, the ruthenium complex having the compound of the present invention as a tridentate ligand was apparently better in catalytic activity, reaction selectivity, and substrate generality in hydrogenation reactions of esters than conventional ruthenium complexes having N,N-bis(2-phosphinoethyl)amine or N,N-bis(2-thioethyl)amine as a tridentate ligand, and it was revealed that the product was obtained from each of methyl benzoate and methyl lactate at a complete conversion and with a complete selectivity.

For $^1$H NMR charts of the complexes of the present invention in Examples 11 to 28 and Example 31, see FIGS. 1 to 19.

INDUSTRIAL APPLICABILITY

The compound of the present invention can be easily produced by a reaction of the compound represented by general formula ($2^A$) with the compound represented by general formula (4), or a reaction of the compound represented by general formula ($3^A$) with the compound represented by general formula (5). Moreover, the compound of the present invention acts as an asymmetric tridentate ligand, and metal complexes of the present invention can be easily produced by coordinating the compound of the present invention to various metal species. Such a metal complex exhibits excellent catalytic activities in catalytic organic synthesis reactions, and, for example, a ruthenium complex comprising the compound of the present invention as a ligand exhibits better catalytic activities in hydrogenation reactions of esters than a ruthenium complex comprising any one of N,N-bis(2-phosphinoethyl)amine and N,N-bis(2-thioethyl)amine, which are conventional symmetrical tridentate ligands. These catalytic reactions make it possible to further efficiently produce alcohols.

The invention claimed is:

1. A compound of the following formula ($1^A$):

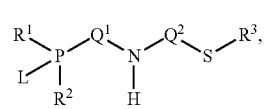

$1^A$ wherein H is a hydrogen atom, N is a nitrogen atom, P is a phosphorus atom, and S is a sulfur atom; L is lone pair electrons or boron trihydride; $R^1$, $R^2$, and $R^3$ each independently are a group selected from the group consisting of alkyl groups, optionally substituted alkenyl groups, optionally substituted aryl groups, optionally substituted heteroaryl groups, and optionally substituted aralkyl groups; $R^1$ and $R^2$ may be bonded to each other to form an optionally substituted ring; and each of $Q^1$ and $Q^2$ is a 1,2-ethanediyl group.

2. The compound according to claim 1, wherein the compound is an optically active compound.

3. A Bronsted acid salt of the compound according to claim 1, wherein
the Bronsted acid salt is formed from the compound according to claim 1 and a Bronsted acid selected from the group consisting of a hydrohalic acid, perchloric acid, nitric acid, sulfuric acid, sulfonic acid, carboxylic acid, phenol, phosphoric acid, hexafluorophosphoric acid, boric acid, and tetrafluoroboric acid.

4. A method for producing the compound according to claim 1, the method comprising reacting
a compound represented by general formula ($2^A$):

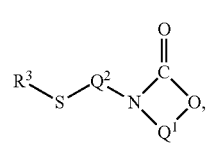

$2^A$ wherein C is a carbon atom, N is a nitrogen atom, O is an oxygen atom, and S is a sulfur atom; and $R^3$, $Q^1$, and $Q^2$ are the same groups as $R^3$, $Q^1$, and $Q^2$ defined in claim 1, with a compound represented by general formula (4):

wherein H is a hydrogen atom and P is a phosphorus atom; L is lone pair electrons or boron trihydride; and $R^1$ and $R^2$ are the same groups as $R^1$ and $R^2$ defined in claim 1.

5. A method for producing the compound according to claim 1, the method comprising reacting a compound represented by general formula ($3^A$):

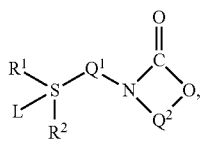

wherein C is a carbon atom, N is a nitrogen atom, O is an oxygen atom, and P is a phosphorus atom; L is lone pair electrons or boron trihydride; and $R^1$, $R^2$, $Q^1$ and $Q^2$ are the same groups as $R^1$, $R^2$, $Q^1$ and $Q^2$ defined in claim 1, with a compound represented by general formula (5):

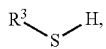

wherein H is a hydrogen atom and S is a sulfur atom; and $R^3$ is the same group as $R^3$ defined in claim 1.

6. A metal complex comprising the compound according to claim 1 as a ligand, wherein the metal species is selected from the group consisting of group 8 transition metals, group 9 transition metals, and group 10 transition metals.

7. The metal complex according to claim 6, wherein the metal complex is represented by compositional formula ($8^A$):

wherein $M^8$ is a divalent group 8 transition metal ion selected from the group consisting of a divalent iron ion, a divalent ruthenium ion, and a divalent osmium ion; $X^1$ and $X^2$ each independently are a monoanionic monodentate ligand, and $L^1$, $L^2$, and $L^3$ each independently are a neutral monodentate ligand; k, l, and m, which respectively are the coordination numbers of $L^1$, $L^2$, and $L^3$, each independently represent an integer of 0 or 1; PNS is the compound according to claim 1; and n, which is the degree of multimerization of the compositional formula: $[M^8X^1X^2(L^1)_k(L^2)_l(L^3)_m(PNS)]$, is an integer of 1 or 2, provided that n is 1 when the total of k, l, and m is an integer of 1 to 3, and is 1 or 2 when the total is 0.

8. The metal complex according to claim 6, wherein the metal complex is represented by compositional formula ($9^A$):

wherein $M^9$ is a trivalent group 9 transition metal ion selected from the group consisting of a trivalent cobalt ion, a trivalent rhodium ion, and a trivalent iridium ion; $X^1$, $X^2$, and $X^3$ each independently are a monoanionic monodentate ligand, and $L^1$, $L^2$, and $L^3$ each independently are a neutral monodentate ligand; k, l, and m, which respectively are the coordination numbers of $L^1$, $L^2$, and $L^3$, each independently are an integer of 0 or 1; and PNS is the compound according to claim 1.

9. The transition metal complex according to claim 6, wherein the transition metal complex is represented by compositional formula ($10^A$):

wherein $M^{10}$ is a divalent group 10 transition metal ion selected from the group consisting of a divalent nickel ion, a divalent palladium ion, and a divalent platinum ion; $X^1$ and $X^2$ each independently are a monoanionic monodentate ligand, and $L^1$ is a neutral monodentate ligand; k, which is the coordination number of $L^1$, is an integer of 0 or 1; and PNS is the compound according to claim 1.

* * * * *